US010596136B2

(12) United States Patent
Chakravarthy et al.

(10) Patent No.: US 10,596,136 B2
(45) Date of Patent: Mar. 24, 2020

(54) COMPOSITIONS AND METHODS FOR THE TREATMENT OF FAT INFILTRATION IN MUSCLE

(71) Applicant: AXCELLA HEALTH INC., Cambridge, MA (US)

(72) Inventors: Manu Chakravarthy, Newton, MA (US); William Comb, Melrose, MA (US); Michael Hamill, Wellesley, MA (US); Tony Tramontin, Brooklyn, NY (US)

(73) Assignee: AXCELLA HEALTH INC., Cambridge, MA (US)

( * ) Notice: Subject to any disclaimer, the term of this patent is extended or adjusted under 35 U.S.C. 154(b) by 0 days.

(21) Appl. No.: 16/446,328

(22) Filed: Jun. 19, 2019

(65) Prior Publication Data
US 2020/0016104 A1    Jan. 16, 2020

Related U.S. Application Data

(60) Provisional application No. 62/687,737, filed on Jun. 20, 2018.

(51) Int. Cl.
A61K 31/19       (2006.01)
A61K 31/4164     (2006.01)
A61K 31/198      (2006.01)
A61P 41/00       (2006.01)
A61P 21/00       (2006.01)
A61K 31/197      (2006.01)
A61K 31/4172     (2006.01)

(52) U.S. Cl.
CPC .......... A61K 31/198 (2013.01); A61K 31/197 (2013.01); A61K 31/4172 (2013.01); A61P 21/00 (2018.01); A61P 41/00 (2018.01)

(58) Field of Classification Search
CPC .......................... A61K 31/19; A61K 31/4164
USPC ........................ 514/561, 400, 562, 565, 567
See application file for complete search history.

(56) References Cited

U.S. PATENT DOCUMENTS

| 693,094 | A | 2/1902 | Wilson |
| 2,457,820 | A | 1/1949 | Howe et al. |
| 3,832,465 | A | 8/1974 | Ghadimi |
| 3,950,529 | A | 4/1976 | Fischer et al. |
| 3,988,466 | A | 10/1976 | Takagi et al. |
| 4,496,703 | A | 1/1985 | Steinmetzer |
| 4,871,550 | A | 10/1989 | Millman |
| 4,898,879 | A | 2/1990 | Madsen et al. |
| 4,908,214 | A | 3/1990 | Bobee et al. |
| 5,028,622 | A | 7/1991 | Plaitakis |
| 5,034,377 | A | 7/1991 | Adibi et al. |
| 5,106,836 | A | 4/1992 | Clemens et al. |
| 5,229,136 | A | 7/1993 | Mark et al. |
| 5,276,018 | A | 1/1994 | Wilmore |
| 5,356,873 | A | 10/1994 | Mark et al. |
| 5,405,835 | A | 4/1995 | Mendy |
| 5,438,042 | A | 8/1995 | Schmidl et al. |
| 5,504,072 | A | 4/1996 | Schmidl et al. |
| 5,520,948 | A | 5/1996 | Kvamme |
| 5,571,783 | A | 11/1996 | Montagne et al. |
| 5,576,351 | A | 11/1996 | Yoshimura et al. |
| 5,712,309 | A | 1/1998 | Finnin et al. |
| 5,719,133 | A | 2/1998 | Schmidl et al. |
| 5,719,134 | A | 2/1998 | Schmidl et al. |
| 5,723,446 | A | 3/1998 | Gray et al. |
| 5,728,678 | A | 3/1998 | Trimbo et al. |
| 5,731,290 | A | 3/1998 | Schneider |
| 5,733,884 | A | 3/1998 | Barbul et al. |
| 5,744,157 | A | 4/1998 | Droge |
| 5,756,481 | A | 5/1998 | Amal et al. |
| 5,780,039 | A | 7/1998 | Greenberg et al. |
| 5,817,329 | A | 10/1998 | Gardiner |
| 5,849,335 | A | 12/1998 | Ballevre et al. |
| 5,863,906 | A | 1/1999 | Arnal et al. |
| 5,866,537 | A | 2/1999 | Bianchi |
| 5,977,073 | A | 11/1999 | Khaled |
| 6,013,273 | A | 1/2000 | Schneider et al. |
| 6,031,000 | A | 2/2000 | Nissen et al. |
| 6,051,236 | A | 4/2000 | Portman |
| 6,087,398 | A | 7/2000 | Goodman |
| 6,096,785 | A | 8/2000 | Schneider |
| 6,143,786 | A | 11/2000 | Gohman et al. |
| 6,218,420 | B1 | 4/2001 | Dioguardi |
| 6,274,612 | B1 | 8/2001 | Bryan |
| 6,281,244 | B1 | 8/2001 | Schneider et al. |

(Continued)

FOREIGN PATENT DOCUMENTS

AU   2014212003    9/2015
CN   1582912 A     2/2005

(Continued)

OTHER PUBLICATIONS

Les et al., "Effects of Branched-Chain Amino Acids Supplementation in Patients with Cirrhosis and a Previous Episode of Hepatic Encephalopathy: A Randomized Study," Am J Gastroenterol (2011)vol. 106, pp. 1081-1088.

Li et al., "A Novel Dual Eigen-Analysis of Mouse Multi-Tissues' Expression Profiles Unveils New Perspectives into Type 2 Diabetes," Sci Rep (2017) vol. 7, Article 5044, 12 pp.

Li et al., "Leucine supplementation increases SIRT1 expression and prevents mitochondrial dysfunction and metabolic disorders in high-fat diet-induced obese mice," Am J Endocrinol Metab (2012) vol. 303, pp. E1234-E1244.

Li, T. et al., "Branched-Chain Amino Acids Alleviate Nonalcoholic Steatohepatitis in Rats," Appl Physiol Nutr Metab., Aug. 2013; 38(8):836-43. doi: 10.1139/apnm-2012-0496. Epub Mar. 8, 2013.

(Continued)

Primary Examiner — Raymond J Henley, III
(74) Attorney, Agent, or Firm — Lando & Anastasi, LLP

(57) ABSTRACT

This disclosure provides methods of using compositions comprising amino acid entities to reduce fat infiltration in muscle, particularly under conditions of muscle atrophy. The disclosure also provides methods for enhancing muscle function by reducing fat infiltration in the muscle comprising administering an effective amount of the compositions to a subject in need thereof.

21 Claims, 4 Drawing Sheets

(56) References Cited

U.S. PATENT DOCUMENTS

| | | |
|---|---|---|
| 6,328,998 B1 | 12/2001 | Cavazza |
| 6,346,264 B1 | 2/2002 | White |
| 6,376,544 B2 | 4/2002 | Lowry et al. |
| 6,391,332 B1 | 5/2002 | Somerville et al. |
| 6,458,338 B1 | 10/2002 | Adjei et al. |
| 6,521,591 B1 | 2/2003 | Smeets et al. |
| 6,833,350 B2 | 12/2004 | Ballevre et al. |
| 6,864,230 B2 | 3/2005 | Ostrom |
| 6,864,242 B2 | 3/2005 | Ernest |
| 7,300,665 B2 | 11/2007 | Mowrey et al. |
| 7,468,193 B2 | 12/2008 | Schiffrin et al. |
| 7,622,447 B2 | 11/2009 | Lautt et al. |
| 7,645,796 B2 | 1/2010 | Murakami et al. |
| 7,790,688 B2 | 9/2010 | Wolfe et al. |
| 7,794,744 B2 | 9/2010 | Ballevre et al. |
| 7,879,796 B2 | 2/2011 | Edens et al. |
| 7,973,077 B2 | 7/2011 | Dioguardi |
| 8,012,924 B2 | 9/2011 | Abe et al. |
| 8,012,926 B2 | 9/2011 | Abe et al. |
| 8,133,503 B2 | 3/2012 | Laflamme et al. |
| 8,148,356 B2 | 4/2012 | Pavliv |
| 8,173,706 B2 | 5/2012 | Anderson et al. |
| 8,211,944 B2 | 7/2012 | Dioguardi |
| 8,362,080 B2 | 1/2013 | Sekhar |
| 8,383,680 B2 | 2/2013 | Whippie et al. |
| 8,389,471 B2 | 3/2013 | Edens et al. |
| 8,389,576 B2 | 3/2013 | Jalan et al. |
| 8,399,445 B2 | 3/2013 | Pavliv |
| 8,409,592 B2 | 4/2013 | Vidal et al. |
| 8,455,531 B2 | 6/2013 | Kramer et al. |
| 8,466,187 B2 | 6/2013 | Kramer et al. |
| 8,492,439 B2 | 7/2013 | Anderson et al. |
| 8,501,676 B2 | 8/2013 | Hageman |
| 8,524,772 B2 | 9/2013 | Arad et al. |
| 8,536,216 B2 | 9/2013 | Dioguardi |
| 8,648,040 B2 | 2/2014 | Edens et al. |
| 8,653,061 B2 | 2/2014 | Pavliv |
| 8,697,630 B2 | 4/2014 | Hayes et al. |
| 8,703,719 B1 | 4/2014 | Abraham et al. |
| 8,703,725 B2 | 4/2014 | Troup et al. |
| 8,716,249 B2 | 5/2014 | Wolfe et al. |
| 8,722,738 B2 | 5/2014 | Pavliv et al. |
| 8,734,316 B2 | 5/2014 | Schmidt |
| 8,785,498 B2 | 7/2014 | Anderson et al. |
| 8,840,950 B2 | 9/2014 | Hibbert et al. |
| 8,846,759 B2 | 9/2014 | Luiking et al. |
| 8,895,059 B2 | 11/2014 | Vrana et al. |
| 8,946,473 B2 | 2/2015 | Anderson et al. |
| 8,952,045 B1 | 2/2015 | Kramer et al. |
| 8,952,046 B1 | 2/2015 | Kramer et al. |
| 8,952,065 B2 | 2/2015 | Pavliv |
| 8,957,101 B1 | 2/2015 | Kramer et al. |
| 9,017,727 B2 | 4/2015 | Buijsse |
| 9,034,925 B2 | 5/2015 | Anderson et al. |
| 9,066,537 B2 | 6/2015 | Hofman et al. |
| 9,066,953 B2 | 6/2015 | Heaton et al. |
| 9,192,593 B2 | 11/2015 | Hirabayashi et al. |
| 9,198,889 B2 | 12/2015 | Heaton et al. |
| 9,216,162 B2 | 12/2015 | Goldstein |
| 9,233,090 B2 | 1/2016 | Breuille et al. |
| 9,260,379 B2 | 2/2016 | Anderson et al. |
| 9,271,521 B2 | 3/2016 | Okita et al. |
| 9,314,444 B2 | 4/2016 | Szewczyk |
| 9,320,759 B2 | 4/2016 | Pan |
| 9,327,028 B2 | 5/2016 | Pavliv et al. |
| 9,364,463 B2 | 6/2016 | Ferrando et al. |
| 9,375,451 B2 | 6/2016 | Hibbert et al. |
| 9,408,410 B2 | 8/2016 | Zemel et al. |
| 9,408,834 B2 | 8/2016 | Zemel et al. |
| 9,410,963 B2 | 8/2016 | Martin et al. |
| 9,492,498 B2 | 11/2016 | Van Goudoever et al. |
| 9,539,226 B2 | 1/2017 | Lee et al. |
| 9,561,194 B2 | 2/2017 | Schiffrin et al. |
| 9,596,870 B2 | 3/2017 | Zanghi et al. |
| 9,604,909 B2 | 3/2017 | Anderson et al. |
| 9,867,391 B2 | 1/2018 | Dardevet et al. |
| 9,878,004 B2 | 1/2018 | Williams et al. |
| 9,913,818 B2 | 3/2018 | Moinard et al. |
| 10,039,735 B2 | 8/2018 | Jalan et al. |
| 10,045,999 B2 | 8/2018 | Jourdan et al. |
| 10,085,947 B2 | 10/2018 | Shah et al. |
| 10,123,985 B2 | 11/2018 | Sabatini et al. |
| 10,201,513 B2 | 2/2019 | Hamill et al. |
| 10,238,617 B2 | 3/2019 | Hamill et al. |
| 2001/0018066 A1 | 8/2001 | Hahn |
| 2001/0041187 A1 | 11/2001 | Hastings et al. |
| 2002/0006907 A1 | 1/2002 | Gardiner et al. |
| 2003/0187049 A1 | 10/2003 | Dioguardi |
| 2004/0023889 A1 | 2/2004 | Gardiner et al. |
| 2004/0067224 A1 | 4/2004 | Ernest |
| 2004/0082659 A1 | 4/2004 | Cooke et al. |
| 2004/0087490 A1 | 5/2004 | Troup et al. |
| 2004/0120983 A1 | 6/2004 | Connolly |
| 2004/0213838 A1 | 10/2004 | Mazer et al. |
| 2005/0020656 A1 | 1/2005 | Horie et al. |
| 2005/0032898 A1 | 2/2005 | Ohtani |
| 2005/0053679 A1 | 3/2005 | Lee et al. |
| 2005/0176827 A1 | 8/2005 | Lee et al. |
| 2005/0197398 A1 | 9/2005 | Sonaka et al. |
| 2006/0002913 A1 | 1/2006 | Gehlsen |
| 2006/0004101 A1 | 1/2006 | Okita et al. |
| 2006/0052455 A1 | 3/2006 | Koga et al. |
| 2006/0159746 A1 | 7/2006 | Troup et al. |
| 2006/0198899 A1 | 9/2006 | Gardiner et al. |
| 2006/0205633 A1 | 9/2006 | Nishitani et al. |
| 2007/0060651 A1 | 3/2007 | Larson et al. |
| 2007/0142469 A1 | 6/2007 | Thomas et al. |
| 2007/0197647 A1 | 8/2007 | Kumada et al. |
| 2007/0212447 A1 | 9/2007 | Nogata et al. |
| 2007/0243211 A1 | 10/2007 | Jaffe |
| 2007/0270355 A1 | 11/2007 | Garcia et al. |
| 2007/0286909 A1 | 12/2007 | Smith et al. |
| 2008/0038321 A1 | 2/2008 | Tsuji et al. |
| 2008/0102137 A1 | 5/2008 | Guffey |
| 2008/0114065 A1 | 5/2008 | Pacioretty et al. |
| 2008/0114067 A1 | 5/2008 | Yamamoto |
| 2008/0161398 A1 | 7/2008 | Verlaan et al. |
| 2008/0182811 A1 | 7/2008 | Ohsu et al. |
| 2008/0268038 A1 | 10/2008 | Wolfe |
| 2009/0011077 A1 | 1/2009 | Schiffrin et al. |
| 2009/0018196 A1 | 1/2009 | Bjork et al. |
| 2009/0048153 A1 | 2/2009 | Varma et al. |
| 2009/0105123 A1 | 4/2009 | Tisdale et al. |
| 2009/0170786 A1 | 7/2009 | Greenberg |
| 2009/0181903 A1 | 7/2009 | Wolfe et al. |
| 2009/0186098 A1 | 7/2009 | Briceno |
| 2009/0203606 A1 | 8/2009 | Wolfe et al. |
| 2009/0306209 A1 | 12/2009 | Daugherty et al. |
| 2010/0021573 A1 | 1/2010 | Gonzalez et al. |
| 2010/0092610 A1 | 4/2010 | Haschke et al. |
| 2010/0104548 A1 | 4/2010 | Rossetti et al. |
| 2010/0119692 A1 | 5/2010 | Hamman et al. |
| 2010/0152107 A1 | 6/2010 | Le-Henand et al. |
| 2010/0233304 A1 | 9/2010 | Pan |
| 2010/0267831 A1 | 10/2010 | Kobayashi et al. |
| 2010/0280119 A1 | 11/2010 | Anderson et al. |
| 2011/0077198 A1 | 3/2011 | Tisdale et al. |
| 2011/0081329 A1 | 4/2011 | Smith et al. |
| 2011/0229447 A1 | 9/2011 | Schiffrin et al. |
| 2011/0257236 A1 | 10/2011 | Koyama et al. |
| 2011/0269678 A1 | 11/2011 | Breuille et al. |
| 2011/0294727 A1 | 12/2011 | Hibbert et al. |
| 2012/0020947 A1 | 1/2012 | Shirazi et al. |
| 2012/0157526 A1 | 6/2012 | Jalan et al. |
| 2012/0178672 A1 | 7/2012 | Wolfe et al. |
| 2012/0195873 A1 | 8/2012 | Miller et al. |
| 2012/0208885 A1 | 8/2012 | Anderson et al. |
| 2012/0251512 A1 | 10/2012 | Farmer et al. |
| 2012/0270860 A1 | 10/2012 | Yoon et al. |
| 2012/0315354 A1 | 12/2012 | Palzer et al. |
| 2012/0329846 A1 | 12/2012 | Matsumoto et al. |
| 2013/0143836 A1 | 6/2013 | Yue et al. |
| 2013/0209433 A1 | 8/2013 | Rossetti et al. |
| 2013/0210715 A1 | 8/2013 | Greenberg et al. |

(56) References Cited

U.S. PATENT DOCUMENTS

| | | |
|---|---|---|
| 2013/0211135 A1 | 8/2013 | Anderson et al. |
| 2013/0225510 A1 | 8/2013 | Greenberg |
| 2013/0296429 A1 | 11/2013 | Anderson et al. |
| 2014/0004205 A1 | 1/2014 | Satyaraj |
| 2014/0037601 A1 | 2/2014 | Greenberg |
| 2014/0093609 A1 | 4/2014 | Roy et al. |
| 2014/0135396 A1 | 5/2014 | Goessling et al. |
| 2014/0147549 A1 | 5/2014 | Jeukendrup et al. |
| 2014/0155448 A1 | 6/2014 | Kato et al. |
| 2014/0249078 A1 | 9/2014 | Breuille et al. |
| 2014/0255511 A1 | 9/2014 | Dardevet et al. |
| 2014/0271984 A1 | 9/2014 | Pouteau et al. |
| 2014/0288327 A1 | 9/2014 | Anderson et al. |
| 2014/0294788 A1 | 10/2014 | Bailey et al. |
| 2014/0295002 A1 | 10/2014 | Heaton et al. |
| 2014/0303099 A1 | 10/2014 | Wolfe et al. |
| 2014/0342040 A1 | 11/2014 | Miller et al. |
| 2014/0343112 A1 | 11/2014 | Ferrando et al. |
| 2014/0356479 A1 | 12/2014 | Serrano |
| 2014/0357553 A1 | 12/2014 | Smola et al. |
| 2014/0357576 A1 | 12/2014 | Breuille et al. |
| 2015/0118351 A1 | 4/2015 | Haschke et al. |
| 2015/0133684 A1 | 5/2015 | Anderson et al. |
| 2015/0223501 A1 | 8/2015 | Huynh-Ba et al. |
| 2015/0246066 A1 | 9/2015 | Nelson |
| 2015/0251990 A1 | 9/2015 | Anderson et al. |
| 2015/0313262 A1 | 11/2015 | Zanghi et al. |
| 2016/0027657 A1 | 1/2016 | Shi et al. |
| 2016/0051814 A1 | 2/2016 | Arigoni et al. |
| 2016/0067201 A1 | 3/2016 | Zemel et al. |
| 2016/0128960 A1 | 5/2016 | Faure et al. |
| 2016/0158305 A1 | 6/2016 | Thomson |
| 2016/0243202 A1 | 8/2016 | Vincent |
| 2016/0302451 A1 | 10/2016 | Hudnall |
| 2016/0338982 A1 | 11/2016 | Ruettimann et al. |
| 2016/0339078 A1 | 11/2016 | Hamill et al. |
| 2016/0367509 A1 | 12/2016 | Pan |
| 2017/0027897 A1 | 2/2017 | Wang et al. |
| 2017/0042189 A1 | 2/2017 | Pibarot et al. |
| 2017/0079897 A1 | 3/2017 | Minus |
| 2017/0079935 A1 | 3/2017 | Schiffrin et al. |
| 2017/0135973 A1 | 5/2017 | Wang et al. |
| 2017/0196944 A1 | 7/2017 | Portman |
| 2017/0360734 A1 | 12/2017 | Blum |
| 2017/0368026 A1 | 12/2017 | Faure et al. |
| 2017/0368027 A1 | 12/2017 | Blum-Sperisen et al. |
| 2017/0370910 A1 | 12/2017 | Rezzi et al. |
| 2018/0015122 A1 | 1/2018 | Villamil Torres et al. |
| 2018/0021278 A1 | 1/2018 | Faure et al. |
| 2018/0036270 A1 | 2/2018 | Aw et al. |
| 2018/0044281 A1 | 2/2018 | Anderson et al. |
| 2018/0125926 A1 | 5/2018 | Williams et al. |
| 2018/0161293 A1 | 6/2018 | Jalan et al. |
| 2018/0169044 A1 | 6/2018 | Hamill et al. |
| 2018/0169045 A1 | 6/2018 | Hamill et al. |
| 2018/0169046 A1 | 6/2018 | Hamill et al. |
| 2018/0169047 A1 | 6/2018 | Hamill et al. |
| 2018/0200192 A1 | 7/2018 | Gammans |
| 2018/0207118 A1 | 7/2018 | Hamill et al. |
| 2018/0207119 A1 | 7/2018 | Hamill et al. |
| 2018/0221320 A1 | 8/2018 | Rose et al. |
| 2018/0296516 A1 | 10/2018 | Hamill et al. |
| 2019/0000866 A1 | 1/2019 | Siegel et al. |
| 2019/0046486 A1 | 2/2019 | De Rienzo et al. |
| 2019/0046487 A1 | 2/2019 | Comb et al. |
| 2019/0105294 A1 | 4/2019 | Hamill et al. |
| 2019/0388374 A1 | 12/2019 | Hanlon et al. |
| 2019/0388375 A1 | 12/2019 | Hanlon et al. |
| 2019/0388376 A1 | 12/2019 | Carroll et al. |
| 2019/0388377 A1 | 12/2019 | Hamill et al. |

FOREIGN PATENT DOCUMENTS

| | | |
|---|---|---|
| CN | 101049500 A | 10/2007 |
| CN | 101332209 B | 12/2010 |
| CN | 101214050 B | 8/2011 |
| CN | 101664384 | 9/2011 |
| CN | 102327259 A | 1/2012 |
| CN | 102961377 A | 3/2013 |
| CN | 105092753 A | 11/2015 |
| CN | 106632605 A | 5/2017 |
| CN | 107242552 A | 10/2017 |
| CN | 108041501 A | 5/2018 |
| CN | 108524453 A | 9/2018 |
| EP | 0147699 A2 | 7/1985 |
| EP | 0656178 | 7/1995 |
| EP | 0827744 A2 | 3/1998 |
| EP | 0882451 A1 | 12/1998 |
| EP | 0891719 A1 | 1/1999 |
| EP | 1004302 A2 | 5/2000 |
| EP | 1025844 A1 | 8/2000 |
| EP | 1083915 B1 | 3/2001 |
| EP | 1108429 A2 | 6/2001 |
| EP | 0764405 B1 | 11/2002 |
| EP | 1399139 A2 | 3/2004 |
| EP | 1541141 A1 | 6/2005 |
| EP | 1552826 A1 | 7/2005 |
| EP | 1637163 A1 | 3/2006 |
| EP | 0983726 B1 | 10/2006 |
| EP | 0674902 B1 | 4/2007 |
| EP | 1774966 A1 | 4/2007 |
| EP | 1774973 A1 | 4/2007 |
| EP | 1938813 A1 | 7/2008 |
| EP | 2060914 A2 | 5/2009 |
| EP | 1374863 B1 | 9/2009 |
| EP | 2095728 A2 | 9/2009 |
| EP | 2196203 A2 | 6/2010 |
| EP | 1085862 B1 | 1/2011 |
| EP | 2091526 B1 | 5/2011 |
| EP | 2340725 A1 | 7/2011 |
| EP | 2413924 B1 | 2/2012 |
| EP | 2440200 B1 | 4/2012 |
| EP | 2196203 B1 | 8/2012 |
| EP | 2601951 A1 | 6/2013 |
| EP | 2327315 B1 | 10/2013 |
| EP | 1549299 B1 | 8/2014 |
| EP | 2792354 A2 | 10/2014 |
| EP | 2799067 A1 | 11/2014 |
| EP | 2865382 A1 | 4/2015 |
| EP | 2968241 B1 | 1/2016 |
| EP | 2977418 A1 | 1/2016 |
| EP | 2786750 B1 | 6/2016 |
| EP | 2327316 B1 | 11/2016 |
| EP | 2574333 B1 | 1/2017 |
| EP | 2440217 B1 | 12/2017 |
| EP | 3263100 A1 | 1/2018 |
| EP | 3298908 A2 | 3/2018 |
| GB | 1034358 A | 6/1966 |
| GB | 2029220 B | 3/1983 |
| GB | 2113524 B | 7/1985 |
| JP | 2003238401 A | 8/2003 |
| JP | 2007055992 A | 3/2007 |
| JP | 2011116775 A | 6/2011 |
| JP | 2011132174 A | 7/2011 |
| JP | 5067160 B2 | 11/2012 |
| JP | 5100033 B2 | 12/2012 |
| JP | 5516654 B2 | 6/2014 |
| JP | 6110444 B2 | 4/2017 |
| KR | 20060124732 A | 12/2006 |
| KR | 100970664 B1 | 7/2010 |
| WO | 1983000085 A1 | 1/1983 |
| WO | 9414458 A1 | 7/1994 |
| WO | 9804254 A1 | 2/1998 |
| WO | 9854985 A1 | 12/1998 |
| WO | 2001026642 A2 | 4/2001 |
| WO | 2001056402 A2 | 8/2001 |
| WO | 2002002092 A2 | 1/2002 |
| WO | 2003103582 A2 | 12/2003 |
| WO | 2004058242 A1 | 7/2004 |
| WO | 2005017094 A2 | 2/2005 |
| WO | 2005021596 A2 | 3/2005 |
| WO | 2005084323 A2 | 9/2005 |
| WO | 2005102301 A2 | 11/2005 |
| WO | 2005110124 A1 | 11/2005 |

(56) References Cited

FOREIGN PATENT DOCUMENTS

| | | | |
|---|---|---|---|
| WO | 2006083381 | A2 | 8/2006 |
| WO | 2006105112 | A2 | 10/2006 |
| WO | 2007002365 | A2 | 1/2007 |
| WO | 2007056176 | A2 | 5/2007 |
| WO | 2007064618 | A1 | 6/2007 |
| WO | 2009109460 | A1 | 9/2009 |
| WO | 2010115055 | A1 | 10/2010 |
| WO | 2010144498 | A2 | 12/2010 |
| WO | 2011030104 | A1 | 3/2011 |
| WO | 2011044230 | A9 | 8/2011 |
| WO | 2011097273 | A1 | 8/2011 |
| WO | 2012005582 | A1 | 1/2012 |
| WO | 2012048043 | A1 | 4/2012 |
| WO | 2012088075 | A1 | 6/2012 |
| WO | 2012092035 | A1 | 7/2012 |
| WO | 2012097061 | A1 | 7/2012 |
| WO | 2012143402 | A1 | 10/2012 |
| WO | 2013006658 | A1 | 1/2013 |
| WO | 2013028547 | A1 | 2/2013 |
| WO | 2013108871 | A1 | 7/2013 |
| WO | 2013188258 | A1 | 12/2013 |
| WO | 2014172341 | A1 | 10/2014 |
| WO | 2015015149 | A1 | 2/2015 |
| WO | 2015048333 | A2 | 4/2015 |
| WO | 2015048340 | A2 | 4/2015 |
| WO | 2015048342 | A2 | 4/2015 |
| WO | 2015048345 | A2 | 4/2015 |
| WO | 2015048346 | A2 | 4/2015 |
| WO | 2015048348 | A2 | 4/2015 |
| WO | 2015061607 | A1 | 4/2015 |
| WO | 2015131152 | A1 | 9/2015 |
| WO | 2015161448 | A1 | 10/2015 |
| WO | 2016003263 | A1 | 1/2016 |
| WO | 2016058919 | A1 | 4/2016 |
| WO | 2016088078 | A1 | 6/2016 |
| WO | 2016094316 | A1 | 6/2016 |
| WO | 2016097299 | A1 | 6/2016 |
| WO | 2016116580 | A1 | 7/2016 |
| WO | 2016121829 | A1 | 8/2016 |
| WO | 2016128576 | A1 | 8/2016 |
| WO | 2016172112 | A1 | 10/2016 |
| WO | 2017001590 | A1 | 1/2017 |
| WO | 2017031131 | A1 | 2/2017 |
| WO | 2017033272 | A1 | 3/2017 |
| WO | 2017053613 | A1 | 3/2017 |
| WO | 2017083758 | A1 | 5/2017 |
| WO | 2017085138 | A1 | 5/2017 |
| WO | 2017107863 | A1 | 6/2017 |
| WO | 2017127333 | A1 | 7/2017 |
| WO | 2017193154 | A1 | 11/2017 |
| WO | 2017202939 | A1 | 11/2017 |
| WO | 2018013873 | A1 | 1/2018 |
| WO | 2018117954 | A1 | 6/2018 |
| WO | 2018118941 | A1 | 6/2018 |
| WO | 2018118957 | A1 | 6/2018 |
| WO | 2019036442 | A1 | 2/2019 |
| WO | 2019036471 | A1 | 2/2019 |

OTHER PUBLICATIONS

Liu et al., "Gene-metabolite network analysis in different nonalcoholic fatty liver disease phernotypes," Experimental & Molecular Medicine (2017) vol. 49, e283, 9 pp.

Liu et al., "Leucine Supplementation Differently Modulates Branched-Chain Amino Acid Catabolism, Mitochondrial Function and Metabolic Profiles at the Different Stages of Insulin Resistance in Rats on High-Fat Diet," Nutrients (2017) vol. 9, Article 565, 20 pp.

Liu, B. et al., "Glutamine Attenuates Obstructive Cholestasis in Rats Via farnesoid X Receptor-Mediated Regulation of Bsep and Mrp2," Can J Physiol Pharmacol, Feb. 2017; 95(2):215-223. doi: 10.1139/cjpp-2016-0389. Epub Oct. 5, 2016.

Lucotti, P. et al., "Beneficial Effects of a Long-Term Oral L-Arginine Treatment Added to a Hypocaloric Diet and Exercise Training Program in Obese, Insulin-Resistant Type 2 Diabetic Patients," (2006) Am J Physiol Endocrinol Metab, 291: E906-E912.

Luiking et al., "Arginine de novo and nitric oxide production in disease states," Am J Physiol Endocrinol Metab (2012) vol. 303, pp. E1177-E1189.

Lynch et al., "Branched-chain amino acids in metabolic signalling and insulin resistance," Nat Rev Endocrinol (2014) vol. 10, No. 12, pp. 723-736.

Lynch et al., "Tissue-specific effects of chronic dietary leucine and norleucine supplementation on protein synthesis in rats," Am J Physiol Endocrinol Metab (2002) vol. 283, pp. E824-E835.

Macotela et al., "Dietary Leucine—An Environmental Modifier of Insulin Resistance Acting on Multiple Levels of Metabolism," PLoS ONE (2011) vol. 6, e21187, 13 pp.

Madden et al., "Ten Amino Acids Essential for Plasma Protein Production Effective Orally or Intravenously," J Exper Med (1943) vol. 77, No. 3, pp. 277-295.

Maddrey, W.C., "Branched Chain Amino Acid Therapy in Liver Disease (abstract only)," J Am Coll Nutr. 1985;4 (6):639-50.

Mager, D.R. et al., "Branched-Chain Amino Acid Needs in Children with Mild-to-Moderate Chronic Cholestatic Liver Disease," J. Nutr, 136: 133-139, 2006.

Malaguarnera et al., "Branched chain amino acids supplemented with L-acetylcarnitine versus BCAA treatmentin hepatic coma: a randomized and controlled double blind study," Eur J Gastroenterol Hepatol (2009) vol. 21, No. 7, pp. 762-770, Abstract Only.

Mansoor et al., "Effect of an enteral diet supplemented with a specific protein blend of amino acid on plasma and muscle protein synthesis in ICU patients," Clinical Nutrition (2007) vol. 26, pp. 30-40.

Marchesini et al., "Branched-Chain Amino Acid Supplementation in Patients with Liver Diseases," J Nutr (2005) vol. 135, pp. 1596S-1601S.

Marchesini et al., "Long-term oral branched-chain amino acid treatment in chronic hepatic encephalopathy," Journal of Hepatology (1990) vol. 11, pp. 92-101.

Marchesini et al., "Nutritional Supplementation With Branched-Chain Amino Acids in Advanced Cirrhosis: A Double-Blind, Randomized Tial," Gastroenterology (2003) vol. 124, No. 7, pp. 1792-1801.

Mardinoglu et al., "Personal model-assisted identification of NAD+ and glutathione metabolism as intervention target in NAFLD," Mol Sys Biol (2017) vol. 13, Article 916, 17 pages.

Marra et al., "Lipotoxicity and the gut-liver axis in NASH pathogenesis," Journal of Hepatology (2017), doi: 10.1016/j.jhep.2017.11.014, 44 pp.

Marra et al., "Roles for Chemokines in Liver Disease," Gastroenterology (2014) vol. 147, pp. 577-594.

Martin et al., "Leucine elicits myotube hypertrophy and enhances maximal contractile force in tissue engineered skeletal muscle in vitro," J Cell Physiol (2017) vol. 232, pp. 2788-2797.

Martin et al., "Whey Proteins Are More Efficient than casein in the Recovery of Muscle Functional Properties following a Casting Induced Muscle Atrophy," PLOS One (2013) vol. 8, No. 9, Article e75408, 8 pp.

Massafra et al., "Farnesoid X Receptor Activation Promotes Hepatic Amino Acid Catabolism and Ammonium Clearance in Mice," Gastroenterology (2017) doi: 10.1053/j.gastro.2017.01.014, 48 pp.

Matoori et al., "Recent advances in the treatment of hyperammonemia," Adv Drug Deliv Rev (2015) doi: 10.1016/j.addr.2015.04.009, 14 pages.

McCarty et al., "The cardiometabolic benefits of glycine: Is glycine an 'antidote' to dietary fructose," Open Heart (2014) vol. 1, Article e000103, 9 pp.

McCarty, "Supplementation with Phycocyanobilin, Citrulline, Taurine, and Supranutritional Doses of Folic Acid and Biotin-Potential for Preventing or Slowing the Progression of Diabetic Complications," Healthcare (2017) vol. 5, Article 15, 28 pp.

McCormack et al., "Circulating Branched-chain Amino Acid Concentrations Are Associated with Obesity and Future Insulin Resistance in Children and Adolescents," Pediatr Obes (2013) vol. 8, No. 1, pp. 52-61.

(56) References Cited

OTHER PUBLICATIONS

McCullough et al., "Stable isotope-based flux studies in nonalcoholic fatty liver disease," Pharmacology & Therapeutics (2017) doi: 10.1016/j.pharmthera.2017.07.008, 12 pp.

McKnight et al., "Beneficial effects of L-arginine on reducing obesity: potential mechanisms and important implications for human health," Amino Acids (2010) vol. 39, pp. 349-357.

Meex et al., "Hepatokines: linking nonalcoholic fatty liver disease and insulin resistance," Nat Rev Endocrinol (2017) doi: 10.1038/nrendo.2017.56, 12 pp.

Miczke, A. et al., "Effect of L-Arginine Supplementation on Insulin Resistance and Serum Adiponectin Concentration in Rats with Fat Diet," (2015) Int J Clin Exp Med, 2015; 8(7); 10358-66.

Mikulski et al., "Effects of supplementation with branched chain amino acids and ornithine aspartate on plasma ammonia and central fatigue during exercise in healthy men," Folia Neuropathol (2015) vol. 53, No. 4, pp. 377-386.

Mirmiran, P. et al., "The Association of Dietary L-Arginine Intake and Serum Nitric Oxide Metabolites in Adults: A Population-Based Study," Nutrients, May 20, 2016; 8(5). pii: E311.

Mittal et al., "A randomized controlled trial comparing lactulose, probiotics, and L-ornithine L-aspartate in treatment of minimal hepatic encephalopathy," Eur J Gastroenterol Hepatol (2011) vol. 23, pp. 725-732.

Moinard et al., "Arginine behaviour after arginine or citrulline administration in older subjects," Br J Nutr (2016) vol. 115, pp. 399-404.

Moinard et al., "Dose-ranging effects of citrulline administration on plasma amino acids and hormonal patterns in healthy subjects: the Citrudose pharmacokinetic study," Br J Nutr (2007) vol. 99, pp. 855-862.

Monti, L.D. et al., "Beneficial Role of L-Arginine in Cardiac Matrix Remodelling in Insulin Resistant Rats," (2008)—European Journal of Clinical Investigation, vol. 38(11):849-56.

Monti, L.D. et al., "Effect of a Long-Term Oral L-Arginine Supplementation on Glucose Metabolism: a Randomized, Double-Blind, Placebo-Controlled Trial," (2012) Diabetes, Obesity and Metabolism 14: 893-900, 2012.

Mordier et al., "Leucine limitation induces autophagy and activation of lysosome-dependent proteolysis in C2C12 myotubes through a mammalian target of rapamycin-independent signaling pathway," J Biol Chem (2000) vol. 275, pp. 29900-29906.

Morgan et al., "Plasma amino-acid patterns in liver disease," Gut (1982) vol. 23, pp. 362-370.

Moriwaki et al., Branched-chain amino acids as a protein- and energy-source in liver cirrhosis, Biochemical and Biophysical Research Communications (2004) vol. 313, pp. 405-409.

Murgas Torrazza et al., "Leucine supplementation of a low-protein meal increases skeletal muscle and visceral tissue protein synthesis in neonatal pigs by stimulating mTOR-dependent translation initiation," J Nutr (2010) vol. 140, pp. 2145-2152.

Murphy et al., "Leucine supplemmentation enhances integrative myofibrillar protein syntesis in free-living older men consuming lower- and higher-protein diets: a parallel-group crossover study," Am J Clin Nutr (2016) vol. 104, pp. 1594-1606.

Musso et al., "Non-alcoholic steatohepatitis: emerging molecular targets and therapeutic strategies," Nat Rev Drug Discovery (2016) vol. 15, pp. 249-274.

Muto et al., "Overweight and obesity increase the risk for liver cancer in patients with liver cirrhosis and long-term oral supplementation with branched-chain amino acid granules inhibits liver carcinogenesis in heavier patients with liver cirrhosis," Hepatology Research (2006) vol. 35, pp. 204-214.

Muto, Y, et al., "Effect of Oral Branched-Chain Amino Acid Granules on Event-Free Survival in Patients with Liver Cirrhosis," Clin Gastroenterol Hepatol., Jul. 2005; 3(7):705-13.

Naganuma et al., "Effect of the Medical Walking and Leucine Enriced Amino acid Containing Food for Female Non-Alcoholic Fatty Liver Disease: Randomized Controlled Trial," Clinical Nutrition (2016) vol. 35, p. S62, Poster SUN-P050.

Eley et al., "Effect of branched-chain amino acids on muscle atrophy in cancer cachexia," Biochem J (2007) vol. 407, pp. 113-120.

English et al., "Leucine partially protects muscle mass and function during bed rest in middle-aged adults," Am J Clin Nutr (2016) vol. 103, pp. 465-473.

Escobar et al., "Regulation of cardiac and skeletal muscle protein synthesis by individual branched-chain amino acids in neonatal pigs," Am J Physiol Endocrinol Metab (2006) vol. 290, pp. E612-E621.

Estes et al., "Modeling the Epidemic of Nonalcoholic Fatty Liver Disease Demonstrates an Exponential Increase in Burden of Disease," Presented at the American Association for Study of Liver Disease in Boston (2016), doi: 10.1002/hep.29466, 26 pp.

Evans et al., "Efficacy of a novel formulation of L-Carnitine, creatine, and leucine on lean body mass and functional muscle strength in healthy older adults: a randomized, double-blind placebo-controlled study," Nutrition & Metabolism (2017) vol. 14, No. 7, 15 pp.

Falach-Malik et al., "N-Acetyl-L-Cysteine inhibits the development of glucose intolerance and hepatic steatosis in diabetes-prone mice," Am J Transl Res (2016) vol. 8, No. 9, pp. 3744-3756.

Farghaly et al., "L-arginine and aminoguanidine reduce colonic damage of acetic acid-induced colitis in rats: potential modulation of nuclear factor-KB/p65," Clin Exp Pharmacol Physiol (2014) vol. 41, No. 10, pp. 769-779, Abstract Only.

Farid et al., "Effects of dietary curcumin or N-acetylcysteine on NF-KB activity and contractile performane in ambulatory and unloaded murine soleus," Nutrition & Metabolism (2005) vol. 2, No. 20, 8 pages.

Fazelian, S et al., "Effects of L-Arginine Supplementation on Antioxidant Status and Body Composition in Obese Patients with Pre-diabetes: A Randomized Controlled Clinical Trial," (2014) Adv Pharm Bull, 4(Suppl 1), 449-454.

Feher et al., "Effect of ornithine-aspartate infusion on elevated serum ammonia concentration in cirrhotic patients—results of a randomized, placebo-controlled double-blind multicentre trial," Med Sci Monit (1997) vol. 3, No. 5, pp. 669-673.

Ferrando et al., "EAA supplementation to increase nitrogen intake improves muscle function during bed rest in the elderly," Clinical Nutrition (2010) vol. 29, pp. 18-23.

Francaux et al., "Aging Reduces the Activation of the mTORC1 Pathway after Resistance Exercise and Protein Intake in Human Skeletal Muscle: Potential Role of REDD1 and Impaired Anabolic Sensitivity," Nutrients (2016) vol. 8, Article 47, 16 pp.

Frank et al., "Dietary protein and lactose increase translation initiation factor activation and tissue protein synthesis in neonatal pigs," Am J Physiol Endocrinol Metab (2006) vol. 290, pp. E225-E233.

Fresenius Kabi, Kabiven® Product Information revised 2016, 24 pages.

Fresenius Kabi, Perikabiven® Product Information revised 2016, 24 pages.

Freudenberg, A et al., "Comparison of High-Protein Diets and Leucine Supplementation in the Prevention of Metabolic Syndrome and Related Disorders in Mice," J Nutr Biochem, Nov. 2012; 23(11):1524-30.

Freudenberg, A. et al., "Dietary L-Leucine and L-Alanine Supplementation Have Similar Acute Effects in the Prevention of High-Fat Diet-Induced Obesity," (2012) Amino Acids, 44:519-528.

Frontiers in Hepatology: NASH and Nutritional Therapy pp. 92-114 (Kiwamu Okita, Ed., 2005) Springer-Verlag, Toyko, Japan.

Fu et al., "Leucine amplifies the effects of metformin on insulin sensitivity and glycemic control in diet-induced obese mice," Metabolism Clinical and Experimental (2015), dx.doi.org/10.1016/j.metabol. 2015.03.007, 12 pp.

Fujita et al., "Essential amino acid and carbohydrate ingestion before resistance exercise does not enhance postexercise muscle protein synthesis," J Appl Physiol (2009) vol. 106, pp. 1730-1739.

Fujita et al., "Nutrient signalling in the regulation of human muscle protein synthesis," The Journal of Physiology (2007) vol. 582, pp. 813-823.

(56) References Cited

OTHER PUBLICATIONS

Fujita, S. et al., "Amino Acids and Muscle Loss with Aging," J Nutr, Jan. 2006; 136(1 Suppl): 277S-280S.

Fukuda et al., "L-Ornithine affects peripheral clock gene expression in mice," Sci Rep (2016) vol. 6, Article 34665, 11 pp.

Gaggini et al., "Altered amino acid concentrations in NAFLD: impact of obesity and insulin resistance," Hepatology, doi: 10.1002/hep.29465, published online Nov. 2017.

Garcia Caraballo et al., "A high-protein diet is anti-steatotic and has no pro-inflammatory side effects in dyslipidaemic APOE2 knock-in mice," Br J Nutr (2014) vol. 112, pp. 1251-1265.

Garcia-Caraballo, S. et al., "Prevention and Reversal of Hepatic Steatosis with a High-Protein Diet in Mice," Biochim Biophys Acta, May 2013; 1832(5):685-95. doi: 10.1016/j.bbadis.2013.02.003. Epub Feb. 11, 2013.

Garg et al., "Therapeutic strategies for preventing skeletal muscle fibrosis after injury," Frontiers in Pharmacology (2015) vol. 6, Article 87, 9 pages.

Gebhardt et al., "Treatment of Cirrhotic Rats with L-Ornithine-L-Aspartate Enhances Urea Synthesis and Lowers Serum Ammonia Levels," J Pharmacol Exp Therapeutics (1997) vol. 283, No. 1, pp. 1-6.

Giam et al., "Effects of Dietary L-Arginine on Nitric Oxide Bioavailability in Obese Normotensive and Obese Hypertensive Subjects," Nutrients (2016) vol. 8, Article 364, 3 pp.

Glover et al., "Immobilization induces anabolic resistance in human myofibrillar protein synthesis with low and high dose amino acid infusion," J Physiol (2008) vol. 586, No. 24, pp. 6049-6061.

Gluchowski et al., "Lipid droplets and liver disease: from basic biology to clinical implications," Nat Rev Gastroenterol Hepatol (2017) doi:10.1038/nrgastro.2017.32, 13 pp.

Gluud et al., "Branched-chain amino acids for people with hepatic encephalopathy," The Cochrane Review (2015) Issue 9, 89 pages.

Gluud et al., "Oral Branched-chain Amino Acids Have a Beneficial Effect on Manifestations of Hepatic Encephaolpathy in a Systematic Review with Meta-Analyses of Randomized Controlled Trials," J Nutr (2013) doi: 10.3945/jn.113.174375, 6 pages.

Goh et al., "L-ornithine L-aspartate for prevention and treatment of hepatic encephalopathy in people with cirrhosis," Cochrane Database of Systematic Reviews (2018) Issue 5, Art No. CD012410, 4 pages.

Goldberg et al., "Oxidation of amino acids by diaphragms from fed and fasted rats," Am J Physiol (1972) vol. 223, pp. 1384-1391.

Goldberg, "Protein synthesis during work-induced growth of skeletal muscle," J Cell Biol (1968) vol. 36, pp. 653-658.

Goldberg, "Protein turnover in skeletal muscle. I. Protein catabolism during work-induced hypertrophy and growth induced with growth hormone," J Biol Chem (1969) vol. 244, No. 12, pp. 3217-3222.

Gomes et al., "Hepatic injury and disturbed amino acid metabolism in mice following prolonged exposure to organophosphorus pesticides," Human and Experimental Toxicology (1999) vol. 18, No. 1, pp. 33-37.

Gomes-Marcondes et al., "A leucine-supplemented diet improved protein content of skeletal muscle in young tumor-bearing rats," Braz J Med Biol Res (2003) vol. 36, pp. 1589-1594.

Gornik et al., "Arginine and Endothelial and Vascular Health," J Nutr (2004) vol. 134, pp. 2880S-2887S.

Graf et al., "Effects of whey protein supplements on metabolism: evidence from human intervention studies," Curr Opin Clin Nutr Metab Care (2011) vol. 14, pp. 569-580.

Guillet et al., "Mitochondrial and sarcoplasmic proteins, but not myosin heavy chain, are sensitive to leucine supplementation in old rat skeletal muscle," Exp Gerontol (2004) vol. 39, pp. 745-751.

Gumucio et al., "Aging-associated exacerbation in fatty degeneration and infiltration after rotator cuff tear," J Shoulder Elbow Surg (2014) vol. 23, pp. 99-108.

Guo et al., "Chronic leucine supplementation improves glycemic control in etiologically distinct mouse models of obesity and diabetes mellitus," Nutrition & Metabolism (2010) vol. 7, Article 57, 10 pp.

Habu et al., "Effect of oral supplementation with branched-chain amino acid granules on serum albumin level in the early stage of cirrhosis: a randomized pilot trial," Hepatology Research (2003) vol. 25, Issue 3, pp. 312-318, Abstract Only.

Haegens et al., "Leucine induces myofibrillar protein accretion in cultured skeletal muscle through mTOR dependent and-independent control of myosin heavy chain mRNA levels," Mol Nutr Food Res (2012) vol. 56, pp. 741-752.

Hagström et al., "Fibrosis stage but not NASH predicts mortality and time to development of severe liver disease in biopsy-proven NAFLD," Journal of Hepatology (2017), doi: 10.1016/j.jhep.2017.07.027, 37 pp.

Ham et al., "Arginine protects muscle cells from wasting in vitro in a an mTORC1-dependent and NO-independent manner," Amino Acids (2014) vol. 46, Issue 12, pp. 2643-2652.

Harris, L-A. et al., "Alterations in 3-Hydroxyisobutyrate and FGF21 Metabolism are Associated with Protein Ingestion-Induced Insulin Resistance," Diabetes (Publish Ahead of Print), published online May 4, 2017, 34 pages.

Harrison et al., "Vitamin E and Vitamin C Treatment Improves Fibrosis in Patients With Nonalcoholic Steatohepatitis," Am J Gastroenterol (2003) vol. 98, pp. 2485-2490.

Najmi et al., "Effect of l-ornithine l-aspartate against thioacetamide-induced hepatic damage in rats," Indian J Pharmacol (2010) vol. 42, No. 6, pp. 384-387.

Nakanishi et al., "Treatment with L-Valine Ameliorates Liver Fibrosis and Restores Thrombopoiesis in Rats Exposed to Carbon Tetrachloride," Tohoku J Exp Med (2010) vol. 221, pp. 151-159.

Nakaya et al., "BCAA-enriched snack improves nutritional state of cirrhosis," Nutrition (2007) vol. 23, pp. 113-120.

Nakaya et al., "Severe catabolic state after prolonged fasting in cirrhotic patients: effect of oral branched-chain amino-acid-enriched nutrient mixture," J Gastroenterol (2002) vol. 37, pp. 531-536.

Nanji et al., "Arginine Reverses Ethanol-Induced Inflammatory and Fibrotic Changes in Liver Despite Continued Ethanol Administration," J Pharmacol Exp Ther (2010) vol. 299, No. 3, pp. 832-839.

Ndraha et al., "The Effect of L-ornithine L-aspartate and Branch Chain Amino Acids on Encephalopathy and Nutritional Status in Liver Cirrhosis with Malnutrition," Acta Med Indones—Indones J Intern Med (2011) vol. 43, No. 1, pp. 18-22.

Newgard, C.B. et al., "A Branched-Chain Amino Acid-Related Metabolic Signature that Differentiates Obese and Lean Humans and Contributes to Insulin Resistance," Cell Metab., Apr. 2009; 9(4):311-26. doi: 10.1016/j.cmet.2009.02.002.

Nicastro et al., "An overview of the therapeutic effects of leucine supplementation on skeletal muscle under atrophic conditions," Amino Acids (2011) vol. 40, pp. 287-300.

Nielsen, "Systems Biology of Metabolism: A Driver for Developing Personalized and Precision Medicine," Cell Metabolism (2017) vol. 25, pp. 572-579.

Nilsson et al., "Metabolic effects of amino acid mixtures and whey protein in healthy subjects: studies using glucose-equivalent drinks," Am J Clin Nutr (2007) vol. 85, pp. 996-1004.

Nishiguchi et al., "Effect of oral supplementation with branched-chain amino acid granules in the early stage of cirrhosis," Hepatology Research (2004) vol. 30, Supplement, pp. 36-41, Abstract Only.

Nishikata et al., "Dietary lipid-dependent regulation of de novo lipogenesis and lipid partitioning by ketogenic essential amino acids in mice," Nutrition and Diabetes (2011) vol. 1, e5, 12 pp.

Nishitani et al., "Pharmacological activities of branched-chain amino acids: augmentation of albumin synthesis in liver and improvement of glucose metabolism in skeletal muscle," Hepatology Research (2004) vol. 30, Supplement, pp. 19-24, Abstract Only.

Nissen et al., "Effect of leucine metabolite b-hydroxy-b-methylbutyrate on muscle metabolism during resistance-exercise training," J Applied Physiology (1996) vol. 81, pp. 2095-2104.

(56) References Cited

OTHER PUBLICATIONS

Nissim et al., "Agmatine Stimulates Hepatic Fatty Acid Oxidation: A Possible Mechanism For Up-Regulation of Ureagenesis," J Biol Chem (2006) vol. 281, No. 13, pp. 8486-8496.
Nissim, I et al., "The Molecular and Metabolic Influence of Long Term Agmatine Consumption," (2014)—The Journal of Biological Chemistry, vol. 289, No. 14, pp. 9710-9729.
Noguchi et al., "Effect of Anaplerotic Fluxes and Amino Acid Availability on Hepatic Lipoapoptosis," J Biol Chem (2009) vol. 284, No. 48, pp. 33425-33436.
Noguchi et al., "Ketogenic Essential Amino Acids Modulate Lipid Synthetic Pathways and Prevent Hepatic Steatosis in Mice," PLOS One (2010) vol. 5, Issue 8, Article e12057, 14 pp.
Norton et al., "Leucine content of dietary proteins is a determinant of postprandial skeletal muscle protein synthesis in adult rats," Nutr Metab vol. 9, 67 (2012).
Norton et al., "The leucine content of a complete meal directs peak activation but not duration of skeletal muscle protein synthesis and mammalian target of rapamycin signaling in rats," J Nutr (2009) vol. 139, pp. 1103-1109.
Ohara et al., "L-Carnitine Suppresses Loss of Skeletal Muscle Mass in Patients With Liver Cirrhosis," Hepatology Communications (2018) vol. 2, No. 8, pp. 906-918.
Okita et al., "Nutritional Treatment of Liver Cirrhosis by Branched-Chain Amino Acid-Enriched Nutrient Mixture," J Nutr Sci Vitaminol (1985) vol. 31, No. 3, pp. 291-303.
Ortiz de Montellano et al., "A New Step in the Treatment of Sickle Cell Disease," Biochemistry (2018) vol. 57, No. 5, pp. 470-471, Abstract.
Pacana, T. et al., "Dysregulated Hepatic Methionine Metabolism Drives Homocysteine Elevation in Diet-Induced Nonalcoholic Fatty Liver Disease," PLoS One, Aug. 31, 2015; 10(8):e0136822. doi: 10.1371/journal.pone.0136822. eCollection 2015.
Pace et al., "Effect of N-acetylcysteine on Dense Cell Formation in Sickle Cell Disease," American Journal of Hematology (2003) vol. 73, No. 1, pp. 26-32.
Paddon-Jones et al., "Essential Amino Acid and Carbohydrate Supplementation Ameliorates Muscle Protein Loss in Humans during 28 Days Bedrest," J Clin Endocrinol Metab (2004) vol. 89, pp. 4351-4358.
Palacio et al., "Anti-inflammatory properties of N-acetylcysteine on lipopolysaccharide-activated macrophages," Inflamm Res (2011) vol. 60, pp. 695-704.
Pennings et al., "Whey protein stimulates postprandial muscle protein accretion more effectively than do casein hydrolysate in older men," Am J Clin Nutr (2011) vol. 93 pp. 997-1005.
Peters et al., "Dose-dependent effects of leucine supplementation on preservation of muscle mass in cancer cachectic mice," Oncol Rep (2011) vol. 26, pp. 247-254.
Petrat et al., "Glycine, a simple physiological compund protecting by yet puzzling mechanism(s) against ischaemia-reperfusion injury: current knowledge," Br J Pharmacol (2011) vol. 165, pp. 2059-2072.
Piatti, P.M. et al., "Long-Term Oral L-Arginine Administration Improves Peripheral and Hepatic Insulin Sensitivity in Type 2 Diabetic Patients," (2001) Diabetes Care, vol. 24, No. 5, May 2001; 24(5):875-80.
Piccolo, B.D. et al., "Plasma Amino Acid and Metabolite Signatures Tracking Diabetes Progression in the UCD-T2DM Rat Model," Am J Physiol Endocrinol Metab, Jun. 1, 2016; 310(11):E958-69. doi: 10.1152/ajpendo.00052.2016. Epub Apr. 19, 2016.
Pilar et al., "L-Ornithine Aspartate Among Cirrhotic Patients with Hepatic Encephalopathy: Does it make a difference?" Phil J of Gastroenterology (2006) vol. 2, pp. 87-94.
Pinheiro et al., "Metabolic and functional effects of beta-hydroxy-beta-methylbutyrate (HMB) supplementation in skeletal muscle," Eur J Appl Physiol (2012) vol. 112, pp. 2531-2537, first published online Nov. 2011, doi: 10.1007/s00421-011-2224-5.
Pintilie, D.G. et al., "Hepatic Stellate Cells' Involvement in Progenitor Mediated Liver Regeneration," Lab Invest, Aug. 2010; 90(8):1199-208. doi: 10.1038/labinvest.2010.88. Epub May 3, 2010.
Plauth et al., "Long-term treatment of latent portosystemic encephalopathy with branched-chain amino acids," Journal of Heaptology (1993) vol. 73, pp. 308-314.
Poo et al., "Efficacy of oral L-ornithine-L-aspartate in cirrhotic patients with hyperammonemic hepatic encephalopathy. Results of a randomized, lactulose-controlled study," Annals of Hepatology (2006) vol. 5, No. 4, pp. 281-288.
Prod'Homme et al., "Insulin and amino acids both strongly participate to the regulation of protein metabolism," Curr Opin Clin Nutr Metab Care (2004) vol. 7, pp. 71-77.
Qiu et al., "Hyperammonemia-mediated autophagy in skeletal muscle contributes to sarcopenia of cirrhosis," Am J Physiol Endocrinol Metab (2012) vol. 303, pp. E983-E993.
Rathmacher et al., "Supplementation with a combination of beta-hydroxy-beta-methylbutyrate (HMB), arginine, and glutamine is safe and could improve hematological parameters," J Parenter Enteral Nutr (2004) vol. 28, No. 2, pp. 65-75.
Reccia et al., "Non-alcoholic fatty liver disease: A sign of systemic disease," Metabolism Clinical and Experimental (2017) vol. 72, pp. 94-108.
Rees et al., "Effect of L-ornithine-L-aspartate on patients with and without TIPS undergoing glutamine challenge: a double-blind, placebo controlled trial," Gut (2000) vol. 47, pp. 571-574.
Ren et al., "Serum Amino Acids Profile and the Beneficial Effects of L-Arginine or L-Glutamine Supplementation in Dextran Sulfate Sodium Colitis," PLOS One (2014) vol. 9, Issue 2, Article e88335, 13 pages.
Ritze et al., "Effect of tryptophan supplementation on diet-induced non-alcoholic fatty liver disease in mice," Br J Nutr (2014) vol. 112, pp. 1-7.
Roederer et al., "N-Acetylcysteine: A New Approach to Anti-HIV Therapy," AIDS Research and Human Retroviruses (1992) vol. 8, No. 2, pp. 209-217.
Rombouts et al., "Targeting the muscle for the treatment and prevention of hepatic encephalopathy," Journal of Hepatology (2016) vol. 65, pp. 876-878.
Romero-Gómez et al., "Altered resonse to oral glutamine challenge as prognostic factor for overt episodes in patientswith minimal hepatic encephalopathy," Journal of Heaptology (2002) vol. 37, pp. 781-787.
Romero-Gómez et al., "Prognostic Value of Altered Oral Glutamine Challenge in Patients With Minimal Hepatic Encephalopathy," Hepatology (2004) vol. 39, No. 4, pp. 939-943.
Rose et al., "L-Ornithine-L-Aspartate in Experimental Portal-Systemic Encephalopathy: Therapeutic Efficacy and Mechanism of Action," Metab Brain Dis (1998) vol. 13, No. 2, pp. 147-157.
Rose et al., "L-Ornithine-L-Aspartate Lowers Plasma and Cerebrospinal Fluid Ammonia and Prevents Brain Edema in Rats with Acute Liver Failure," Hepatology (1999) vol. 30, No. 3, pp. 636-640.
Ullrich et al., "Intragastric administration of leucine or isoleucine lowers the blood glucose response to a mixed-nutrient drink by different mechanisms in healthy, lean volunteers," Am J Clin Nutr (2016) vol. 104, pp. 1274-1284.
Van De Poll et al., "Intestinal and hepatic metabolism of glutamine and citrulline in humans," J Physiol (2007) vol. 581, No. 2, pp. 819-827.
Van Vliet et al., "The Skeletal Muscle Anabolic Response to Plant-versus Animal-Based Protein Consumption," J Nutr (2015) vol. 14, No. 5, pp. 1981-1991.
Varakanahalli et al., "Secondary prophylaxis of hepatic encephalopathy in cirrhosis of liver: a double-blind randomized controlled trial of L-ornithine L-aspartate versus placebo," Eur J Gastroenterol Hepatol (2018) vol. 30, pp. 951-958.
Vela et al., "Efficacy of oral L-orinthine L-aspartate in cirrhotic patients with hyperammonemic hepatic encephalopathy," Annals of Hepatology (2011) vol. 10, Supp. 2, pp. S55-S59.
Ventura et al., "Evidence for a role of the ileum in the control of nitrogen homeostasis via the regulation of arginine metabolism," Br J Nutr (2011) vol. 106, pp. 227-236.

(56) References Cited

OTHER PUBLICATIONS

Ventura-Cots et al., "Impact of ornithine phenylacetate (OCR-002) in lowering plasma ammonia after upper gastrointestinal bleeding in cirrhotic patients," Ther Adv Gastroenterol (2016) vol. 9, No. 6, pp. 823-836.
Wahren, J. et al., "Is Intravenous Administration of Branched Chain Amino Acids Effective in the Treatment of Hepatic Encephalopathy? A Multicenter Study. (abstract only)," Hepatology, Jul.-Aug. 1983; 3(4):475-80.
Watanabe et al., Beneficial Effect of Food Substitute Containing L-Arginine, w-3 Poly Unsaturated Fatty Acid, and Ribonucleic Acid in Preventing or Improving Metabolic Syndrome: A Study in 15 Overweight Patients and a Study of Fatty Acid Metabolism in Animals, J Clin Biochem Nutr (2009) vol. 44, pp. 266-274.
Waugh et al., "Evidence that L-Arginine is a Key Amino Acid in Sickle Cell Anemia—A Preliminary Report," Nutrition Research (1999) vol. 19, No. 4, pp. 501-518.
Wilkinson et al., "Effects of leucine and its metabolite b-hydroxy-b-methylbutyrate on human skeletal muscle protein metabolism," J Physiol (2013) vol. 591, No. 11, pp. 2911-2923.
Wilson et al., "Differential effects of long-term leucine infusion on tissue protein synthesis in neonatal pigs," Amino Acids (2011) vol. 40, pp. 157-165.
Xu et al., "Ketogenic essential amino acids replacement diet ameliorated hepatosteatosis with altering autophagy-associated molecules," Biochimica et Biophysica Acta (2013) vol. 1832, pp. 1605-1612.
Yamada et al., Association between insulin resistance and plasma amino acid profile in non-diabetic Japanese subjects, J Diabetes Invest (2015) vol. 6, pp. 408-415.
Yamamoto et al., "Branched-chain amino acids protect against dexamethasone-induced soleus muscle atrophy in rats," Muscle Nerve (2010) vol. 41, pp. 819-827.
Yang et al., "Resistance exercise enhances myofibrillar protein synthesis with graded intakes of whey protein in older men," Br J Nutr (2012) vol. 108, pp. 1780-1788.
Yao et al., "Dietary Arginine Supplementation Increases mTOR Signaling Activity in Skeletal Muscle of Neonatal Pigs," J Nutr (2008) vol. 138, pp. 867-872.
Yi et al., N-Acetylcysteine improves intestinal function in lipopolysaccharides challenged piglets through multiple signaling pathways, Amino Acids (2017) doi: 10.1007/s00726-017-2389-2, 15 pp.
Yin et al., "Supplementing L-leucine to a low-protein diet increases tissue protein synthesis in weanling pigs," Amino Acids (2010) vol. 39, pp. 1477-1486.
Yokota et al., "Leucine restores murine hepatic triglyceride accumulation induced by a low-protein diet by suppressing autophagy and excessive endoplasmic reticulum stress," Amino Acids (2016) vol. 48, pp. 1013-1021.
Yoshiji et al., "Branched-chain amino acids suppress the cumulative recurrence of hepatocellular carcinoma under condititions of insulin-resistance," Oncology Reports (2013) vol. 30, pp. 545-552.
Younossi et al., "Global burden of NAFLD and NASH: trends, predictions, risk factors and prevention," Nat Rev (2017) doi:10.1038/nrgastro.2017.109, 10 pp.
Yuan et al., "Leucine supplementation improves leptin sensitivity in high-fat diet fed rats," Food & Nutrition Research (2015) vol. 59, Article 27373, 6 pp.
Zarfeshani et al., "Leucine alters hepatic glucose/lipid homeostasis via the myostatin-AMP-activated protein kinase pathway—potential implications for nonalcoholic fatty liver disease," Clinical Epigenetics (2014) vol. 6, Article 27, 12 pages.
Zeanandin et al., "Differential effect of long-term leucine supplementation on skeletal muscle and adipose tissue in old rats: an insulin signaling pathway approach," Age (2012) vol. 34, pp. 371-387.
Zhang et al., "Branched Chain Amino Acids Cause Liver Injury in Obese/Diabetic Mice by Promoting Adipocyte Lipolysis and Inhibiting Hepatic Autophagy," EBioMedicine (2016) vol. 13, pp. 157-167.
Zhang et al., Supporting Materials for "Branched Chain Amino Acids Cause Liver Injury in Diabetic Mice by Promoting Adipocyte Lipolysis and Inhibiting Hepatic Autophagy," EBioMedicine (2016) doi.org/10.1016/j.ebiom.2016.10.013, 15 pp.
Zhang, Y. et al., "Increasing Dietary Leucine Intake Reduces Diet-Induced Obesity and Improves Glucose and Cholesterol Metabolism in Mice via Multimechanisms," Diabetes. Jun. 2007; 56(6):1647-54. Epub Mar. 14, 2007.
Zhou et al., "Glycine protects against high sucrose and high fat-induced non-alcoholic steatohepatitis in rats," Oncotarget (2016) vol. 7, No. 49, pp. 80223-88237.
Roseguini et al., "Effects of N-Acetylcysteine on skeletal muscle structure and function in a mouse model of peripheral arterial insufficiency," J Vasc Surg (2015) vol. 61, pp. 777-786.
Rui, "Energy Metabolism in the Liver," Compr Physiol (2014) vol. 4, No. 1, pp. 177-197.
Saad et al., "Attenuation of carbon tetrachloride induced hepatic fibrosis by glycine, vitamin E, and vitamin C," J Exp Integr Med (2014) vol. 4, Issue 3, pp. 180-186.
Sabater et al., "Altered Nitrogen Balance and Decreased Urea Excretion in Male Rats Fed Cafeteria Diet Are Related to Arginine Availability," BioMed Research International (2014) vol. 2014, Article 959420, 9 pp.
Sakai, H. et al., "Chemoprevention of Obesity-Related Liver Carcinogenesis by Using Pharmaceutical and Nutraceutical Agents," World J Gastroenterol,Jan. 7, 2016; 22(1): 394-406.
Salvatore et al., "Prevention of Ammonia Toxicity by Amino-acids concerned in the Biosynthesis of Urea," Nature (1961) vol. 191, No. 4789, pp. 705-706.
Samuel et al., "Nonalcoholic Fatty Liver Disease as a Nexus of Metabolic and Hepatic Diseases," Cell Metabolism (2017) vol. 27, doi: 10.1016/j.cmet.2017.08.002, 20 pp.
Sansbury, B.E. et al., "Regulation of Obesity and Insulin Resistance by Nitric Oxide," (2014)—Free Radical Biology and Medicine, 73: 383-399.
Schiffrin, "Enteral nutrition in the ICU. The Nestle Modulis innovation. Physiopathology of the traumatized patient in the ICU," Nutrition clinique et metabolisme (2007) vol. 21, p. S6-S10. Abstract Only.
Schmid et al., "A double-blind, randomized, placebo-controlled trial of intravenous L-ornithine-L-aspartate on postural control in patients with cirrhosis," Liver International (2010) doi: 10.1111/j.1478-3231.2010.02213.x, pp. 574-582.
Schuppan et al., "Determinants of Fibrosis Progression and Regression in NASH," Journal of Hepatology (2017), doi: 10.1016/j.jhep.2017.11.012, 39 pp.
Schwarz et al., "Dietary Protein Affects Gene Expression and Prevents Lipid Accumulation in the Liver in Mice," PLOS One (2012) vol. 7, Issue 10, Article e47303, 9 pp.
Schwimmer, J.B. et al., "In Children With Nonalcoholic Fatty Liver Disease, Cysteamine Bitartrate Delayed Release Improves Liver Enzymes but Does Not Reduce Disease Activity Scores," Gastroenterology, 2016; 151:1141-1154.
Sellmann et al., "Oral arginine supplementation protects female mice from the onset of non-alcoholic steatohepatitis," Amino Acids (2016) vol. 49, No. 7, pp. 1215-1225.
Sellmann et al., "Oral Supplementation of Glutamine Attenuates the Progression of Nonalcoholic Steatohepatitis in C57BL/6J Mice," J Nutr (2017) doi: 10.3945/jn.117.253815, 9 pp.
Sellmann, C. et al., "Oral Glutamine Supplementation Protects Female Mice from Nonalcoholic Steatohepatitis," J Nutr, Oct. 2015; 145(10):2280-6. doi: 10.3945/jn.115.215517. Epub Aug. 5, 2015.
Sen et al., "Oxidative stress after human exercise: effect of N-acetylcysteine supplementation," J Appl Physiol (1994) vol. 76, No. 6, pp. 2570-2577.
Sen et al., "Thiol homeostasis and supplements in physical exercise," Am J Clin Nutr (2000) vol. 72, Supp., pp. 653S-659S.
Setshedi et al., "N-Acetylcysteine Improves Hepatic Insulin Resistance Associated with High-Fat Diet and Alcohol-Induced Steatohepatitis," Gastroenterology (2010) vol. 138, No. 5, p. S801, Abstract S1846.

(56) References Cited

OTHER PUBLICATIONS

Sharawy et al., "Attenuation of insulin resistance in rats by agmatine: role of SREBP-1c, mTOR and GLUT-2," Naunyn-Schmiedeberg's Arch Pharmacol (2016) vol. 389, pp. 45-56.
Sharawy et al., "The ergogenic suplement β-hydroxy-β-methylbutyrate (HMB) attenuates insulin resistance through suppressinf GLUT-2 in rat liver," Can J Physiol Pharmacol (2016) vol. 94, pp. 488-497.
Sharma et al., "Effect of Rifazimin, Probiotics, and l-Ornithine l-Aspartate on Minimal Hepatic Encephalopathy: A Randomized Controlled Trial," Saudi J Gastroenterol (2014) vol. 20, pp. 225-232.
Shimizu, M. et al., "Nutraceutical Approach for Preventing Obesity-Related Colorectal and Liver Carcinogenesis," Int. J. Mol. Sci., 2012, 13, 579-595.
Shrestha et al., "Glutamine inhibits CCl4 induced liver fibrosis in mice and TGF-β1 mediated epithelial-mesenchymal transition in mouse hepatocytes," Food and Chemical Toxicology (2016) vol. 93, pp. 129-137.
Sidhu et al., "L-Ornithine L-Aspartate in Bouts of Overt Hepatic Encephalopathy," Hepatology (2018) vol. 67, No. 2, pp. 700-710.
Sidransky et al., "Skeletal muscle protein metabolism changes in rats force-fed a diet inducing an experimental Kwashiorkor-like model," Am J Clin Nutr (1970) vol. 23, pp. 1154-1159.
Sim et al., "L-Serine Supplementation Attenuates Alcoholic Fatty Liver by Enhancing Homocysteine Metabolism in Mice and Rats," J Nutr (2014) vol. 145, pp. 260-267.
Simpson et al., "The nutritional geometry of liver disease including non-alcoholic fatty liver disease (NAFLD)," J Hepatol (2017), doi: 10.1016/;j.jhep.2017.10.005, 10 pp.
Smith et al., "Dietary omega-3 fatty acid supplementation increases the rate of muscle protein synthesis in older adults: a randomized controlled trial," American Journal of Clinical Nutrition (2011) vol. 93, pp. 402-412.
Smith et al., "Treatment of Non-Alcoholic Fatty Liver Disease (NAFLD): Role of AMPK," Am J Physiol Endocrinol Metab (2016) doi:10.1152/ajpendo.00225.2016, 25 pp.
Soomro et al., "Role of Branched Chain Amino Acids in the Management of Hepatic Encephalopathy," World J Med Sci (2008) vol. 3, No. 2, pp. 60-64.
Squires et al., "A Prospective Clinical Trial Shows That Intravenous N-Aceytlcysteine (NAC) Does Not Improve Survival in Pediatric Patients With Non-Acetaminophen Acute Liver Failure," Gastroenterology (2011) vol. 140, Issue 5, Supplement 1, p. S-897.
Staedt et al., "Effects of ornithine aspartate on plasma ammonia and plasma amino acids in patients with cirrhosis. A double-blind, randomized study using a four-fold crossover design," Journal of Hepatology (1993) vol. 19, pp. 424-430.
Stauch et al., "Oral L-ornithine-L-aspartate therapy of chronic heaptic encephalopathy: results of a placebo-controlled double-blind study," Journal of Hepatology (1998) vol. 28, pp. 856-864.
Stokes et al., "L-ornithine L-aspartate for people with cirrhosis and hepatic encephalopathy," Cochrane Database of Systematic Reviews (2016) Issue 10, Art No. CD012410, 14 pages.
Sun et al., "Melatonin improves non-alcoholic fatty liver disease via MAPK-JNK/P38 signaling in high-fat-diet-induced obese mice," Lipids in Health and Disease (2016) vol. 15, Article 202, 8 pp.
Sunny et al., "Cross-talk between branched-chain amino acids and hepatic mitochondria is compromised in nonalcoholic fatty liver disease," Am J Physiol Endocrinol Metab (2015) vol. 309, pp. E311-E319.
Suryawan et al., "Leucine stimulates protein synthesis in skeletal muscle of neonatal pigs by enhancing mTORC1 activation," Am J Physiol Endocrinol Metab (2008) vol. 295, pp. E868-E875.
Tachibana et al., "Intake of Mung Bean Protein Isolate Reduces Plasma Triglyceride Level in Rats," Functional Foods in Health and Disease (2013) vol. 3, No. 9, pp. 365-376.
Tajiri et al., "Branched-chain amino acids in liver diseases," World J Gastroenterol (2013) vol. 19, Issue 43, pp. 7620-7629.

Takaguchi et al., "Effects of branched-chain amino acid granules on serum albumin level and prognosis are dependent on treatment adherence in patients with liver cirrhosis," Hepatology Research (2013) vol. 43, pp. 459-466.
Takashi et al., "Branched-chain amino acids alleviate hepatic steatosis and liver injury in choline-deficient high-fat diet induced NASH mice," Metabolism (2017) doi: 10.1016/j.metabol.2016.12.013, 45 pp.
Takegoshi, K. et al., "Branched-Chain Amino Acids Prevent Hepatic Fibrosis and Development of Hepatocellular Carcinoma in a Non-Alcoholic Steatohepatitis Mouse Model," Oncotarget, Mar. 14, 2017; 8(11):18191-18205. doi:10.18632/oncotarget.15304.
Talvas et al., "Regulation of protein synthesis by leucine starvation involves distinct mechanisms in mouse C2C12 myoblasts and myotubes," J Nutr (2006) vol. 136, pp. 1466-1471.
Tan, B et al., "Regulatory Roles for L-Arginine in Reducing White Adipose Tissue," (2012) Frontiers in Bioscience, 17, 2237-2246, Jun. 1.
Tanaka et al., "Branched-chain Amino Acid-Rich Supplements Containing Microelements Have Antioxidant Effects on Nonalcoholic Steatohepatitis in Mice," J Parenteral and Enteral Nutrition (2016) vol. 40, No. 4, pp. 519-528.
Theytaz et al., "Effects of supplementation with essential amino acids on intrahepatic lipid concentrations during frutose overfeeding in mice," Am J Clin Nutr (2012) vol. 96, pp. 1008-1016.
Thomsen et al., "Experimental nonalcoholic steatohepatitis compromises ureagenesis, an essential hepatic metabolic function," Am J Physiol Gastrointest Liver Physiol (2014) vol. 307, pp. G295-G301.
Thong-Ngam et al., "N-acetylcysteine attenuates oxidative stress and liver pathoogy in rats with non-alcoholic steatohepatitis," World J Gastroenterol (2007) vol. 13, No. 38, pp. 5127-5132.
Tsien et al., "Metabolic and Molecular Responses to Leucine-Enriched Branched Chain Amino Acid Supplementation in the Skeletal Muscle of Alcoholic Cirrhosis," Hepatology (2015) vol. 61, No. 6, pp. 2018-2029.
[No Author Listed] MediKAL Nutrience Hepatosol-LOLA product information, retrieved from www.medikalnutrience.com/EN/Product/By-Brand/Hepatosol-LOLA, last accessed Sep. 13, 2018, 9 pages.
[No Author Listed] New Drug Application 18-676 and Approval Letter for HepatAmine (1982), 73 pages.
[No Author Listed] NUTRIHEP product information, retrieved from www.nestlehealthscience-me.com/en/brands/nutrihep/nutrihep, last accessed Sep. 12, 2013.
[No Author Listed] Twinlab "Anti-catabolic HMB Fuel Plus: HMB, NAC, Glutamine & Creatine," Product Label, 1996.
Abid et al., "Efficacy of L-ornithine-L-aspartate as an Adjuvant Therapy in Cirrhotic Patients with Hepatic Encephalopathy," Journal of the College of Physicians and Surgeons Pakistan (2011) vol. 21, No. 11, pp. 666-671.
Abu-Serie, M.M. et al., "Investigation into the Antioxidant Role of Arginine in the Treatment and the Protection for Intralipid-Induced NASH," (2015), Lipids in Health and Disease, 14:128.
Achamrah et al., "Glutamine and the regulation of intestinal permeability: from bench to bedside," Curr Opin Clin Nutr Metab Care (2017) vol. 20, pp. 86-91.
Acharya et al., "Efficacy of L-Ornithine L-Aspartate in Acute Liver Failure: A Double-Blind, Randomized, Placebo-Controlled Study," Gastroenterology (2009) vol. 136, pp. 2159-2168.
Adeva et al., "Insulin resistance and the metabolism of branched-chain amino acids in humans," Amino Acids (2012) vol. 43, pp. 171-181.
Adibi et al., "Metabolism of branched-chain amino acids in altered nutrition," Metab Clin Exp (1976) vol. 25, pp. 1287-1302.
Agarwal et al., "Supplemental Citrulline Is More Efficient than Arginine in Increasing Systemic Arginine Availability in Mice," J Nutr (2017) doi: 10.3945/jn.116.240382, 7 pp.
Agli et al., "Erythrocytes participate significantly in blood transport of amino acids during the post absorptive state in normal humans," Eur J Appl Physiol (1998) vol. 78, pp. 502-508.
Agten et al., "N-Acetylcysteine protects the rat diaphragm from the decreased contractility associated with controlled mechanical ventilation," Crit Care Med (2011) vol. 39, No. 4, pp. 777-782.

(56) References Cited

OTHER PUBLICATIONS

Ahmad et al., "L-Ornithine-L-Aspartate Infusion Efficacy in Hepatic Encephalopathy," Journal of the College of Physicians and Surgeons Pakistan (2008) vol. 18, No. 11, pp. 684-687.

Alvares-da-Silva et al., "Oral l-ornithine-l-aspartate in minimal hepatic encephalopathy: A randomized, double-blind, placebo-controlled trial," Hepatology Research (2014) vol. 44, pp. 956-963.

Amodio et al., "Nutritional Management of Hepatic Encephalopathy in Patients With Cirrhosis: International Society for Hepatic Encephalopathy and Nitrogen Metabolism Consensus," Hepatology (2013) vol. 58, pp. 325-336.

Anthony et al., "Leucine stimulates translation initiation in skeletal muscle of postabsorptive rats via a rapamycin-sensitive pathway," J Nutr (2000) vol. 130, pp. 2413-2419.

Apostol et al., "A Decrease in Glucose Production Is Associated With an Increase in Plasma Citrulline Response to Oral Arginine in Normal Volunteers," Metabolism (2003) vol. 52, No. 11, pp. 1512-1516.

Araujo et al., "Benefits of L-alanine or L-arginine supplementation against adiposity and glucose intolerance in monosodium glutamate-induced obesity," Eur J Nutr (2016) doi: 10.1007/s00394-016-1245-6, 12 pp.

Argilés et al., "Branched-chain amino acid catabolism and cancer cachexia (Review)," Oncol Rep (1996) vol. 3, No. 4, pp. 687-690.

Aversa et al., "β-hydroxy-β-methylbutyrate (HMB) attenuates muscle and body weight loss in experimental cancer cachexia," International J of Oncology (2011) vol. 38, pp. 713-720.

B. Braun Medical Inc., Package Insert for HepatAmine, NDA 18-676/S-022 pp. 5-15, Revised May 2003.

B. Braun Medical Inc., Product Catalog for HepatAmine (8% Amino Acid Injection), 2012, retrieved from www.bbraunusa.com/content/dam/catalog/bbraun/bbraunProductCatalog/CW_US/en-us/b0/hepatamine-8-aminoacidinjectionbrochure.pdf.bb-.38324315/hepatamine-8-aminoacidinjectionbrochure.pdf.

B. Braun Medical Inc., Product Catalog, retrieved from www.bbraunusa.com/en/products-and-therapies/product-catalog.html, last accessed Sep. 13, 2018.

Backx et al., "Leucine Supplementation Does Not Attenuate Skeletal Muscle Loss during Leg Immobilization in Healthy, Young Men," Nutrients (2018) vol. 10, Article 635, 12 pages.

Bahadoran et al., "Dietary L-arginine intake and the incidence of coronary heart disease: Tehran lipid and glucose study," Nutrition & Metabolism (2016) vol. 13, No. 23, 9 pp.

Bai et al., "Randomised clinical trial: L-ornithine-L-aspartate reduces significantly the increase of venous ammonia concentration after TIPSS," Ailment Pharmacol Ther (2014) vol. 40, pp. 63-71.

Balage et al., "Leucine supplementation in rats induced a delay in muscle IR/PI3K signaling pathway associated with overall impaired glucose tolerance," The Journal of Nutritional Biochemistry (2011) vol. 22, pp. 219-226 (Abstract Only).

Balage et al., "Long-term effects of leucine supplementation on body composition," Curr Opin Clin Nutr Metab Care (2010) vol. 13, pp. 265-270.

Baptista et al., "Leucine attenuates skeletal muscle wasting via inhibition of ubiquitin ligases," Muscle Nerve (2010) vol. 41, pp. 800-808.

Bauchart-Thevret et al., "Arginine-induced stimulation of protein synthesis and survival in IPEC-J2 cells is mediated by mTOR but not nitric oxide," Am J Physiol Endocrinol Metab (2010) vol. 299, pp. E899-E909.

Baum et al., "Docosahexaenoic Acid (DHA), not Leucine, May Protect HepG2 Cells from Palmitate-Induced Non-Alcoholic Fatty Liver Disease," FASEB J (2017) Abstract No. 1036.7.

Baum et al., "Leucine reduces the duration of insulin-induced PI 3-kinase activity in rat skeletal muscle," Am J Physiol Endocrinol Metab (2005) vol. 288, pp. E86-E91.

Baumgardner, J.N. et al., "N-Acetylcysteine Attenuates Progression of Liver Pathology in a Rat Model of Nonalcoholic Steatohepatitis," J Nutr, Oct. 2008; 138(10):1872-9.

Bernard et al., "An amino acid mixture is essential to optimize insulin-stimulated glucose uptake and GLUT4 translocation in perfused rodent hindlimb muscle," J Appl Physiol (2012) vol. 113, pp. 97-104.

Binder et al., "Leucine Supplementation Protects from Insulin Resistance by Regulating Adiposity Levels," PLOS One (2013) vol. 8, No. 9, Article e74705, 12 pp.

Bos et al., "Postprandial Kinetics of Dietary Amino Acids Are the Main Determinant of Their Metabolism after Soy or Milk Protein Ingestion in Humans," J Nutr (2003) vol. 133, pp. 1308-1315.

Bostock et al., "Effects of Essential Amino Acid Supplementation on Muscular Adaptations to 3 Weeks of Combined Unilateral Glenohumeral & Radiohumeral Joints Immobilisation," J Athl Enhancemnet (2013) vol. 2, No. 3, Article 1000116, 9 pp.

Breen et al., "Skeletal muscle protein metabolism in the elderly: Interventions to counteract the 'anabolic resistance' of ageing," Nutr Metab (2011) vol. 8: 68, 11 pp.

Breuillard et al., "Citrulline and nitrogen homeostasis: an overview," Amino Acids (2015) vol. 47, pp. 685-691.

Breuille et al., "Beneficial effect of amino acid supplementation especially cysteine, on body nitrogen economy in septic rats," Clinical Nutrition (2006) vol. 25, pp. 634-642.

Brioche et al., "Muscle wasting and aging: Experimental models, fatty infiltrations, and prevention," Molecular Aspects of Medicine (2016) vol. 50, pp. 56-87.

Butterworth et al., "Hepatoprotection by L-Ornithine L-Aspartate in Non-Alcoholic Fatty Liver Disease," Dig Dis (2018) DOI: 10.1159/000491429, 6 pages.

Bémeur et al., "Nutrition in the Management of Cirrhosis and its Neurological Complications," J Clin Exp Hepatol (2014) vol. 4, No. 2, pp. 141-150.

Børsheim et al., "Amino acid supplementation decreases plasma and liver triglycerides in elderly," Nutrition (2009) vol. 25, No. 3, pp. 281-288.

Børsheim et al., "Effect of amino acid supplementation on muscle mass, strength and physical function in elderly," Clin Nutr (2008) vol. 27, pp. 189-195.

Calvey et al., "Controlled Trial of Nutritional Supplementation With and Without Branched Chain Amino Acid Enrichment, in Treatment of Acute Alcoholic Hepatitis," Journal of Hepatology (1985) vol. 1, pp. 141-151.

Campollo et al., "Protein tolerance to standard and high protein meals in patients with liver cirrhosis," World J Hepatol (2017) vol. 9, Issue 14, pp. 667-676.

Campos-Ferraz et al., "An overview of amine as nutritional supplements to counteract cancer cachexia," J Cachexia Sarcopenia Muscle (2014) vol. 5, No. 2, pp. 105-110.

Campos-Ferraz et al., "Distinct effects of leucine or a mixture of the branched-chain amino acids (leucine, isoleucine, and valine) supplementation on resistance to fatigue, and muscle and liver-glycogen degradation, in trained rats," Nutrition (2013) vol. 29, pp. 1388-1394.

Hassan, A. et al., "Effects of Oral L-Carnitine on Liver Functions after Transarterial Chemoembolization in Intermediate-Stage HCC Patients," Mediators Inflamm, 2015; 2015:608216. doi: 10.1155/2015/608216. Epub Nov. 19, 2015.

Hayashi et al., "A Randomized Controlled Trial of Branched-Chain Amino Acid (BCAA)-Enriched Elemental Diet (ED-H) for Hepatic Encephalopathy," J Gastroenterol Hepatol (1991) vol. 6, p. 191, Abstract Only.

Herlong et al., "The Use of Ornithine Salts of Branched-Chain Ketoacids in Portal-Systemic Encephalopathy," Annals of Internal Medicine (1980) vol. 93, pp. 545-550.

Hermier et al., "NO synthesis from arginine is favored by a-linolenic acid in mice fed a high-fat diet," Amino Acids (2016) vol. 48, pp. 2157-2168.

Higuera-De-La-Tijera et al., Primary Prophylaxis to Preventthe Development of Hepatic Enchephalopathy in Cirrhotic Patients with Acute Variceal Bleeding, Candian Journal of Gastroenterology and Hepatology (2018) Article 3015891, 10 pages.

Holdsworth et al., "Body protein metabolism and plasma amino acits in cirrhosis of the liver. The effect of varying the branched

(56) References Cited

OTHER PUBLICATIONS chain amino acid content of intravenous amino acid solutions," Clinical Nutrition (1984) vol. 3, pp. 153-162.
Holecek, "Branched-chain amino acid supplementation in treatment of liver cirrhosis: Updated views on how to attenuate their harmful effects on cataplerosis and ammonia formation," Nutrition (2017) vol. 41, pp. 80-85.
Holecek, "Branched-chain amino acids and ammonia metabolism in liver disease," Nutrition (2013) vol. 29, pp. 1186-1191.
Holecek, "Evidence of a vicious cycle in glutamine synthesis and breakdown in pathogenesis of hepatic encephalopathy-therapeutic perspectives," Metab Brain Dis (2014) vol. 29, pp. 9-17.
Holecek, "Three targets of branched-chain amino acid supplementation in the treatment of liver disease," Nutrition (2010) vol. 26, pp. 482-490.
Horst et al., "Comparison of Dietary Protein with an Oral, Branched Chain-Enriched Amino Acid Supplement in Chronic Portal-Systemic Encephalopathy: A Randomized Controlled Trial," Hepatology (1984) vol. 4, No. 2, pp. 279-287.
International Search Report and Written Opinion issued in PCT/US2017/067345, dated Mar. 9, 2018, 13 pages.
International Search Report and Written Opinion issued in PCT/US2017/067368, dated Apr. 18, 2018, 12 pages.
International Search Report and Written Opinion issued in PCT/US2018/046705, dated Nov. 23, 2018, 13 pages.
Ishikawa, "Early administration of branched-chain amino acid granules," World J Gastroenterol (2012) vol. 18, Issue 33, pp. 4486-4490.
Iwakiri et al., "Nitric oxide in liver diseases," Trends in Pharmacological Sciences (2015) vol. 36, No. 8, pp. 524-536.
Iwasa et al., "Branched-Chain Amino Acid Supplementation Reduces Oxidative Stress and Prolongs Survival in Rats with Advanced Liver Cirrhosis," PLOS One (2013) vol. 8, Issue 7, Article e70309, 11 pages.
Jackman et al., "Branched-Chain Amino Acid Ingestion Stimulates Muscle Myofibrillar Protein Synthesis following Resistance Exercise in Humans," Frontiers in Physiology (2017) vol. 8, Article 390, 12 pages.
Jalan et al., "L-Ornithine phenylacetate (OP): A novel treatment for hyperammonemia and hepatic encephalopathy," Medical Hypotheses (2007) vol. 69, pp. 1064-1069.
Jang, C. et al., "A Branched-Chain Amino Acid Metabolite Drives Vascular Fatty Acid Transport and Causes Insulin Resistance," Nat Med., Apr. 2016; 22(4):421-6. doi: 10.1038/nm.4057. Epub Mar. 7, 2016.
Jegatheesan et al., "Hepatic steatosis: a role for citrulline," Curr Opin Clin Nutr Metab Care (2016) vol. 19, No. 5, pp. 360-365.
Jegatheesan et al., "Preventive effects of citrulline on Western diet-induced non-alcoholic fatty liver disease in rats," Br J Nutr (2016) vol. 1161, pp. 191-203.
Jegatheesan, P. et al., "Citrulline and Nonessential Amino Acids Prevent Fructose-Induced Nonalcoholic Fatty Liver Disease in Rats," Nutr, Oct. 2015; 145(10):2273-9.
Jegatheesan, P. et al., "Effect of Specific Amino Acids on Hepatic Lipid Metabolism in Fructose-Induced Non-Alcoholic Fatty Liver Disease," (2016) Clinical Nutrition, 35: 175-182.
Jennings et al., "Associations between branched chain amino acid intake and biomarkers of adiposity and mardiometabolic health independent of genetic factors: A twin study," Intl J Cardiology (2016) vol. 223, pp. 992-998.
Jha et al., "Network Integration of Parallel Metabolic and Transcriptional Data Reveals Metabolic Modules that Regulate Macrophage Polarization," Immunity (2015) vol. 42, pp. 419-430.
Jiao, J. et al., "Chronic leucine Supplementation Improves Lipid Metabolism in C57BL/6J Mice Fed with a High-Fat/Cholesterol Diet," Food Nutr Res., Sep. 9, 2016; 60:31304. doi: 10.3402/fnr. v60.31304. eCollection 2016.

Jobgen, W. et al., "Dietary L-Arginine Supplementation Reduces White Fat Gain and Enhances Skeletal Muscle and Brown Fat Masses in Diet-Induced Obese Rats," J Nutr, Feb. 2009; 139(2):230-7.
Kakazu et al., "Plasma amino acids imbalance in cirrhotic patients disturbs the tricarboxylic acid cycle of dendritic cell," Sci Rep (2013) vol. 3, Article 3459, 8 pages.
Kakumitsu, S. et al., "Effects of L-Arginine on the Systemic, Mesenteric, and Hepatic Circulation in Patients With Cirrhosis," Hepatology, Feb. 1998; 27(2):377-82.
Kanda et al., "Post-exercise whey protein hydrolysate supplementation induces a greater increase in muscle protein synthesis than its constituent amino acid content," Br J Nutr (2013) vol. 110, pp. 981-987.
Katsanos et al., "Whey protein ingestion in elderly results in greater muscle protein accrual than ingestion of its constituent essential amino acid content," Nutr Res (2008) vol. 28, No. 10, pp. 651-658.
Kawaguchi et al., "Branched-Chain Amino Acids Prevent Hepatocarcinogenesis and Prolong Survival of Patients With Cirrhosis," Clinical Gastroenterology and Hepatology (2014) vol. 12, pp. 1012-1018.e1.
Kawaguchi et al., "Effects of Oral Branched-Chain Amino Acids on Hepatic Encephalopathy and Outcome in Patients With Liver Cirrhosis," Nutr Clin Pract (2013) vol. 28, No. 5, pp. 580-588.
Kawaguchi et al., "Wheat-bran autolytic peptides containing a branched-chain amino acid attenuate non-alcoholic steatohepatitis via the suppression of oxidative stress and the upregulation of AMPJ/ACC in high-fat diet-fed mice," International J Molecular Medicine (2017) vol. 39, pp. 407-414.
Kelleher et al., "The mTORC1 signaling repressors REDD1/2 are rapidly induced and activation of p70S6K1 by leucine is defective in skeletal muscle of an immobilized rat hindlimb," Am J Physiol Endocrinol Metab (2013) vol. 304, pp. E229-E236.
Kerksick et al., "The Antioxidant Role of Glutathione and N-Acetyl-Cysteine Supplements and Exercise-Induced Oxidative Stress," Journal of the International Society of Sports Nutrition (2005), vol. 2, No. 2, pp. 38-44.
Khoshbaten, M. et al., "N-Acetylcysteine Improves Liver Function in Patients with Non-Alcoholic Fatty Liver Disease," Hepat Mon, 2010 Winter; 10(1):12-6. Epub Mar. 1, 2010.
Kim et al., "Acetyl CoA Carboxylase Inhibition Reduces Hepatic Steatosis but Elevates Plasma Triglycerides in Mice and Humas: A Bedside to Bench Investigation," Cell Metabolism (2017) vol. 26, pp. 394-406.
Kim et al., "Quantity of dietary protein intake, but not pattern of intake, affects net protein balance primarily through differences in protein synthesis in older adults," Am J Physiol Endocrinol Metab (2015) vol. 308, No. 1, pp. E21-E28.
Kinny-Köster et al., "Plasma Amino Acid Concentrations Predct Mortality in Patients with End-Stage Liver Disease," PLOS One (2016) vol. 11, No. 7, Article e0159205, 13 pages.
Kircheis et al., "Assessment of low-grade hepatic encephalopathy: a critical analysis," Journal of Hepatology (2007) vol. 47, pp. 642-650.
Kircheis et al., "Therapeutic Efficacy of L-Ornithine-L-Aspartate Infusions in Patients With Cirrhosis and Hepatic Encephalopathy: Results of a Placebo-Controlled, Double-Blind Study," Hepatology (1997) vol. 25, pp. 1351-1360.
Kitajima et al., "Supplementation with branched-chain amino acids ameliorates hypoalbuminemia, prevents sarcopenia, and reduces fat accumulation in the skeletal muscles of patients with liver cirrhosis," J Gastroenterol (2017) doi 10.1007/s00535-017-1370-x, 11 pages.
Knudsen et al., "L-leucine methyl ester stimulates insulin secretion and islet glutamate dehydrogenase," Am J Physiol (1983) vol. 245, pp. E338-E346.
Krenitsky, "Nutrition Update in Hepatic Failure," Practical Gastroenterology (2014) pp. 47-55.
Kumar et al., "Ammonia lowering reverses sarcopenia or cirrhosis by restoring skeletal muscle proteostasis," Hepatol (2017) vol. 65, No. 6, pp. 2045-2058.

(56) References Cited

OTHER PUBLICATIONS

Kuwahata et al., "Supplementation with branched-chain amino acids attenuates hepatic apoptosis in rats with chronic liver disease," Nutrition Research (2012) vol. 32, pp. 522-529.
Kwanten et al., "Role of autophagy in the pathophysiology of nonalcoholic fatty liver disease: A controversial issue," World J Gastroenterol (2014) vol. 20, Issue 23, pp. 7325-7338.
Le Plénier et al., "Citrulline directly modulates muscle protein syntheses via the PI3K/MAPK/4E-BP1 pathway in a malnourished state: evidence from in vivo, ex vivo, and in vitro studies," Am J Physiol Endocrinol Metab (2017) vol. 312, pp. E27-E36.
Capel et al., "Combining citrulline with atorvastatin preserves glucose homeostasis in a murine model of diet-induced obesity," Br J Pharmacol (2015) vol. 172, pp. 4996-5008.
Capel et al., "Lysosomal and proteasome-dependent proteolysis are differentially regulated by insulin and/or amino acids following feeding in young, mature and old rats," J Nutr Biochem (2009) vol. 20, pp. 570-576.
Carraro et al., "Whole body and plasma protein synthesis in exercise and recorvery in human subjects," Am J Physiol Endocinol Metab (1990) vol. 258, pp. E821-E831.
Chang et al., "Leucine inhibits oxidation of glucose and pyruvate in skeletal muscles during fasting," J Biol Chem (1978) vol. 253, pp. 3696-3701.
Charlton, M., "Branched-Chain Amino Acid Enriched Supplements as Therapy for Liver Disease," 2006 J. Nutrition, 136: 295S-298S.
Chartrand et al., "Influence of Amino Acids in Dairy Products on Glucose Homeostasis: The Clinical Evidence," Can J Diabetes (2017), 9 pp.
Chen et al., "Therapeutic effect of L-ornithine-L-aspartate on liver cirrhosis complicated by hepatic encephalopathy," J First Mil Med Univ (2005) vol. 25,No. 6, pp. 718-722. Abstract Only.
Cheng et al., "Adipose Tissue Dysfunction and Altered Systemic Amino Acid Metabolism Are Associated with Non-Alcoholic Fatty Liver Disease," PLOS One (2015) doi:10.1371/journal.pone. 0138889, 17 pp.
Cholewa et al., "Dietary preoteins and amino acids in the control of the muscle mass during immobilization and aging: role of the MPS response," Amino Acids (2017) vol. 49, No. 5, pp. 811-820.
Churchward-Venne et al., "Leucine supplementation of a low-protein mixed macronutrient beverage enhances myofibrillar protein synthesis in young men: a double-blind, randomized trial," Am J Clin Nutr (2014) vol. 99, pp. 276-286.
Churchward-Venne et al., "Supplementation of a suboptimal protein dose with leucine or essential amino acids: effects on myofibrillar protein syntheses at rest and following resistance exercise in men," J Physiol (2012) vol. 590, No. 11, pp. 2751-2765.
Clemmensen et al., "Oral L-Arginine Stimulates GLP-1 Secretion to Improve Glucose Tolerance in Male Mice," Endocrinology (2013) vol. 154, No. 11, pp. 3978-3983.
ClincalTrials.gov Identifier: NCT01434108 "Effects of the Administration of Ornithine Phenylacetate in Patients with Cirrhosis and Upper Gastrointestinal Bleeding," Clinicaltrials.gov, last updated Mar. 24, 2015, 7 pages.
ClincalTrials.gov Identifier: NCT01548690 "Safety Study of Ornithine Phenylacetate to Treat Patients With Acute Liver Failure (STOP-ALF)," Clinicaltrials.gov, last updated Jan. 12, 2018, 13 pages.
ClincalTrials.gov Identifier: NCT01634230 "Emergency Use of OCR-002 in Acute Liver Failure," Clinicaltrials.gov, last updated Jun. 18, 2014, 4 pages.
ClincalTrials.gov Identifier: NCT01966419 "Phase 2B Efficacy/Safety of Ornithine Phenylacetate in Hospitalized Cirrhotic Patients With Hepatc Encephalopathy (STOP-HE) (STOP-HE)," Clinicaltrials.gov, last updated Aug. 21, 2018, 6 pages.
ClincalTrials.gov Identifier: NCT03159390 "Metabolism of Ornithine Phenylacetate (OCERA OP)," Clinicaltrials.gov, last updated May 23, 2017, 6 pages.
Cuthbertson et al., "Anabolic signaling deficits underlie amino acid resistance of wasting, aging muscle," The FASEB Journal (2005) vol. 19, pp. 422-424.

D'Antona et al., "A Peculiar Formula of Essential Amino Acids Prevents Rosuvastatin Myopathy in Mice," Antioxidants & Redox Signaling (2016) vol. 25, No. 11, pp. 595-608.
D'Antona et al., "Branched-Chain Amino Acid Supplementation Promotes Survival and Supports Cardiac and Skeletal Muscle Mitochondrial Biogenesis in Middle-Aged Mice," Cell Metabolism (2010) vol. 12, pp. 362-372.
Dam et al., "Branched-chain amino acids and muscle ammonia detoxification in cirrhosis," Metab Brain Dis (2013) vol. 28, pp. 217-220.
Dam et al., "Branched-chain amino acids increase arterial blood ammonia in spite of enhanced intrinsic muscle ammonia metabolism in patients with cirrhosis and healthy subjects," Am J Physiol Gastrointest Liver Physiol (2011) vol. 301, pp. G269-G277.
Dangin et al., "The digestion rate of protein is an independent regulating factor of postprandial protein retention," Am J Physiol Endocrinol Metab (2001) vol. 280, pp. E340-E348.
Dardevet et al., "Muscle Wasting and Resistance of Muscle Anabolism: The 'Anabolic Threshold Concept' for Adapted Nutritional Strategies during Sarcopenia" The Scientific World Journal (2012) vol. 93, article 269531.
Dashtabi, A. et al., "Oral L-Arginine Administration Improves Anthropometric and Biochemical Indices Associated With Cardiovascular Diseases in Obese Patients: A Randomized, Single Blind Placebo Controlled Clinical Trial," (2016) Res Cardiovasc Med, February; 5(1): e29419.
Davuluri et al., "Metabolic adaptation of skeletal muscle to hyperammonemia drives the beneficial effects of L-leucine in cirrhosis," J Hepatology (2016) vol. 65, pp. 929-937.
De Bandt et al., "A Randomized Controlled Trial of the Influence of the Mode of Enteral Onithine μ-Ketoglutarate Administration in Burn Patients," J Nutr (1998) vol. 128, pp. 563-569.
Deglaire et al., Hydrolyzed dietary casein as compared with the intact protein reduces postprandial peripheral, but not whole-body, uptake of nitrogen in humans, Am J Clin Nutr (2009) vol. 90, pp. 1011-1022.
Deldicque et al., "Antagonistic effects of leucine and glutamine on the mTOR pathway in myogenic C2C12 cells," Amino Acids (2008) vol. 35, No. 1, pp. 147-155, first published online Nov. 2007.
Deminice et al., "Creatine Supplementation Prevents the Accumulation of Fat in the Livers of Rats Fed a High-Fat Diet," J Nutr (2011) vol. 141, pp. 1799-1804.
Deutz et al., "Protein intake and exercise for optimal muscle function with again: Recoomndations from the ESPEN Expert Group," Clinical Nutrition (2014) vol. 33, pp. 929-936.
Diaz-Rua, E. et al., "Long-Term Intake of a High-Protein Diet Increases Liver Triacylglycerol Deposition Pathways and Hepatic Signs of Injury in Rats," Journal of Nutritional Biochemistry, 46 (2017) 39-48.
Diaz-Rua, E. et al., "Sustained Exposure to Diets with an Unbalanced Macronutrient Proportion Alters Key Genes Involved in Energy Homeostasis and Obesity-Related Metabolic Parameters in Rats," 2014 Food & Function, pp. 1-15.
Dickinson et al., "Aging differentially affects human skeletal muscle amino acid transporter expression when essential amino acids are ingested after exercise," Clin Nutr (2013) vol. 32, pp. 273-280.
Dickinson et al., "Mammalian Target of Rapamycin Complex 1 Activation Is Required for the Stimulation of Human Skeletal Muscle Protein Synthesis by Essential Amino Acids," J Nutr (2011) vol. 141, pp. 856-862.
Dilger et al., "Oral N-acetyl-L-cysteine is a safe and effective precursor of cysteine," J Anim Sci (2007) vol. 85, pp. 1712-1718.
Dillon, "Nutritionally essential amino acids and metabolic signaling in aging," Amino Acids (2012). doi:10.1007/s00726-012-1438-0, 11 pp.
Dirks et al., "Skeletal Muscle Disuse Atrophy Is Not Attenuated by Dietary Protein Supplementation in Healthy Older Men," J Nutr (2014) vol. 144, pp. 1196-1203.
Dohil, R., et al., "Enteric-Coated Cysteamine for the Treatment of Paediatric Non-Alcoholic Fatty Liver Disease," Alimentary Pharmacology & Therapeutics, 33.9 (2011): 1036-1044.

(56) References Cited

OTHER PUBLICATIONS

Doi et al., "Isoleucine, a Blood Glucose-Lowering Amino Acid, Increases Glucose Uptake in Rat Skeletal Muscle in the Absence of Increases in AMP-Activated Protein Kinase Activity," J Nutr (2005) vol. 135, pp. 2103-2108.
Doi, M. et al., "Hypoglycemic Effect of Isoleucine Involves Increased Muscle Glucose Uptake and Whole Body Glucose Oxidation and Decreased Hepatic Gluconeogenesis," Am. J. Physiol. Endocrinal Metab., 2007, pp. E1683-E1693, vol. 292.
Dou et al., "Ameliorative effects of glycine in an experimental nonalcoholic steatohepatitis and its correlation between TREM-1 and TREM-2," Am J Transl Res (2016) vol. 8, No. 2, pp. 284-297.
Dreyer et al., "Essential amino acid supplementation in patients following total knee arthroplasty," J Clin Invest (2013) vol. 123, No. 11, pp. 4654-4666.
Dreyer et al., "Leucine-enriched essential amino acid and carbohydrate ingestion following resistance exercise enhances mTOR signaling and protein synthesis in human muscle," Am J Physiol Endocrinol Metab (2008) vol. 294, E392-400.
Drummond et al. "Bed rest impairs skeletal muscle amino acid transporter expression, mTORC1 signaling, and protein synthesis in response to essential amino acids in older adults," Am J Physiol Endocrinol Metab (2012) vol. 302, pp. E1113-E1122.
Drummond et al., "Skeletal muscle protein anabolic response to resistance exercise and essential amino acids is delayed with aging," J Appl Physiol (2008) vol. 104, pp. 1452-1461.
Dröge et al., "Role of Cysteine and Glutathione in HIV infection and cancer cachexia: Therapeutic intervention with N-acetylcysteine," Advances in Phamacology (1997) vol. 38, pp. 581-600.
Du et al., "Effects of Histidine Supplementation on Global Serum and Urine 1H NMR-based Metabolomics and Serum Amino Acid Profiles in Obese Women from a Randomized Controlled Study," J Proteome Res (2017) vol. 16, pp. 2221-2230.
Egberts et al., "Branched Chain Amino Acids in the Treatment of Latent Portosystemic Encephalopathy," Gastroenterology (1985) vol. 88, pp. 887-895.
Ejima et al., "A novel diet-induced murine model of steatohepatitis with fibrosis for screening and evaluation of drug candidates for nonalcoholic steatohepatitis," Physiol Rep (2016) vol. 4, No. 21, Article e13016, 13 pp.

[No Author Listed] 2016 Nutricia Product Reference Guide, downloaded from nutricia-na.com/ pages/2016_Canada_PRG.pdf dated Nov. 20, 2019.
[No Author Listed] National Guideline Centre, Royal College of Physicians, "Cirrhosis in over 16s, Assessment and Management," NICE guideline NG50, Appendices A-H, Jul. 2016, 351 pages.
[No Author Listed] Nutricia Metabolics, "Practical Guide for the Use of Nutricia's TYR Products," downloaded from www.nutricialearningcenter.com/globalassets/pdfs/metabolics/tyr_gudelines on Nov. 20, 2019. Publicly available Jan. 11, 2013.
[No Author Listed] PubChem entry for L-Orinthine-L-aspartate, PubChem CID 10220941 (2019), 17 pages.
Addison et al., "Intermuscular Fat: A Review of the Consequences and Causes," International Journal of Endocrinology (2014) vol. 2014, Article 309570, 11 pages.
Holloway et al., "A Novel Amino Acid Composition Ameliorates Short-Term Muscle Disuse Atrophy in Healthy Young Men," Frontiers in Nutrition (2019) vol. 6, Article 105, 10 pages.
Hurt et al., "L-Arginine for the Treatment of Centrally Obese Subjects: A Pilot Study," Journal of Dietary Supplements :2014) vol. 11, No. 1, pp. 40-52.
International Search Report and Written Opinion issued in PCT/US2019/037932, dated Oct. 7, 2019.
International Search Report and Written Opinion issued in PCT/US2019/037936, dated Oct. 2, 2019.
Lee et al., "AXA1125, a novel defined amino acid composition (DAAC), improves NAFLD activity score (NAS) and reduces fibrosis in two rodent models of nonalcoholic steatohepatitis (NASH)," EASL Abstracts from the First NAFLD Summit (2017) Abstract P02-05, pp. 64-65.
Martina et al., "Long-Term N-Acetylcysteine and L-Arginine Administration Reduces Endothelial Activation and Systolic Blood Pressure in Hyptertensive Patients With Type 2 Diabetes," Diabetes Care (2008) vol. 31, No. 5, pp. 340-944.
Miyake et al., "Long-term Branched-chain Amino Acid Supplementation Improves Glucose Tolerance in Patients with Nonalcoholic Steatohepatitis-related Cirrhosis," Intern Med (2012) vol. 51, pp. 2151-2155.
Tsuda et al., "Combined Effect of Arginine, Valine, and Serine on Excercise-Induced Fatigue in Healthy Volunteers: A Randomized, Double-Blind, Placebo-Controlled Crossover Study," Nutrients (2019) vol. 11, Article 862, 12 pages.
U.S. Appl. No. 16/674,317, filed Nov. 5, 2019.
van Loon et al., "Amino Acid Ingestion Strongly Enhances Insulin Secretion in Patients With Long-Term Type 2 Diabetes," Diabetes Care (2003) vol. 26, No. 3, pp. 625-630.

Arrows depict fat infiltration

COMPOSITIONS AND METHODS FOR THE TREATMENT OF FAT INFILTRATION IN MUSCLE

RELATED APPLICATIONS

This application claims priority to U.S. Ser. No. 62/687,737, filed Jun. 20, 2018, the contents of which is incorporated herein by reference in its entirety.

BACKGROUND

There are many diseases and disorders associated with increased infiltration of fat in muscle, e.g., muscle atrophy. Muscle atrophy is associated with cancer, AIDS, renal failure, liver disease, spinal cord injury, and congestive heart failure. Furthermore, disuse of muscles through immobilization or aging also results in muscle atrophy with increased fat infusion in muscle.

The gold standard for treating muscle atrophy conditions is recovery of function. However, direct assessment of muscle functional muscle mass is challenging (Evans et al., 2019, Journal of Cachexia, Sarcopenia and Muscle, 10:14-21). Furthermore, the ability to reduce infiltration of fat in muscle is an important therapeutic target, with few if any pharmacological agents available.

Thus, there is a need to identify pharmacological methods of reducing fat infiltration in muscle, and to use such agents to reduce fat infiltration in muscle, particularly under conditions of muscle atrophy. Furthermore, there is a need to identify markers of functional muscle mass to develop additional metabolic rebalancing compositions for enhancing muscle mass and function (relative to not receiving any therapy), such as for treating muscle-related disease and disorders where fat infiltration in muscle occurs.

SUMMARY

The invention provides method for reducing fat infiltration in muscle comprising administering to a subject at risk of fat infiltration in muscle a composition comprising an Active Moiety. The Active Moiety comprises:

a) a leucine amino acid entity, an arginine amino acid entity, and a glutamine amino acid entity;

b) a N-acetylcysteine (NAC) entity; and c) an essential amino acid (EAA)-entity chosen from a histidine amino acid-entity, a lysine amino acid-entity, a phenylalanine amino acid-entity, and a threonine amino acid-entity or a combination of two, three, or four of the EAAs.

The method can be used to reduce fat infiltration in muscle of a subject at risk of fat infiltration in muscle who has a rotator cuff injury, and in particular administration of the composition precedes a surgery for the rotator cuff injury. The invention can include determining a level of fat infiltration in shoulder muscle affected by the rotator cuff injury, e.g., before surgery or after surgery. In a specific embodiment, the subject with a rotator cuff injury is an elderly subject.

Alternatively, the method can be used to reduce fat infiltration in muscle of a subject at risk of fat infiltration in muscle who has chronic back pain (fat infiltration in paraspinal muscles); HIV patients (fat infiltration in locomotor muscles); spinal cord injury; stroke; COPD; end-stage liver disease (ESLD), e.g., hepatic encephalopathy, variceal bleeding, portal hypertension, ascites, infection risk, sepsis, all-cause hospitalization, and all-cause and liver-related mortality; and muscle weakness associated with ageing. Furthermore, the administering the composition to the subject at risk of fat infiltration in muscle can improve a muscle function of sequestering glucose, e.g., when the subject at risk for fat infiltration in muscle has diabetes or metabolic disease.

In yet another alternative, the subject at risk of fat infiltration in muscle has cancer, e.g., colorectal cancer or periampullary cancer. Preferably the cancer is treated surgically in conjunction with the methods of the invention.

In still another alternative, the subject at risk for fat infiltration in muscle does not have significant increase in BMI, sarcopenia, or other overt conditions, or the subject at risk for fat infiltration in muscle suffers from cirrhosis without sarcopenia.

Very few reliable methods are available to measure intramuscular fat infiltration (IMF); magnetic resonance imaging (MRI) is one of them. Computer tomography (CT) can also be used, but it is not as efficient at MRI.

A significant advantage of the invention is the ability to finely regulate the amount and relative ratio of each amino acid in the composition, which is not possible with peptides of more than 20 amino acids in length, including proteins. Thus, in the methods of the invention, the composition preferably does not include a peptide of more than 20 amino acid residues in length. In another aspect, at least one of methionine (M), trytophan (W), valine (V), or cysteine (C) is absent, or if present, is present at less than 1 weight (wt.) % of dry weight, particularly dry weight of the Active Moiety. Furthermore, the composition can further comprise an isoleucine amino acid entity, a valine amino acid entity, or both an isoleucine amino acid entity and a valine amino acid entity.

While the methods envision compositions of amino acid entities, in specific embodiments exemplified in the application, at least one of the leucine amino acid entity, the arginine amino acid, the glutamine amino acid entity, or one, two, three, or all of the EAA amino acid entities is a free amino acid; all of them can be free amino acids. Thus, it is possible that at least 50 wt. % of the total dry wt. of the composition is one or more amino acid entities in free form. Alternatively, at least one of the leucine amino acid entity, the arginine amino acid entity, the glutamine amino acid entity, or one, two, three, or all of the EAA amino acid entities is in salt form; all of them can be in salt form. Thus, it is possible that at least 50 wt. % of the total dry wt. of the composition is one or more amino acid entities in salt form.

As demonstrated in the example, the method can be practiced with a composition comprising about 0.5 g to about 15 g of the leucine amino acid entity, about 0.25 g to about 10 g of the isoleucine amino acid entity, about 0.25 g to about 10 g of the valine amino acid entity, about 0.5 to about 25 g of the arginine amino acid entity, about 0.5 g to about 20 g of the glutamine amino acid entity, about 0.1 to about 5 g the NAC or a salt thereof, about 0.05 g to about 3 g of the L-histidine or a salt thereof, about 0.05 to about 6 g of the L-lysine or a salt thereof, about 0.04 to about 2 g of the L-phenylalanine or a salt thereof, and about 0.08 to about 4 g of the L-threonine or a salt thereof entity; e.g., about 1 g of the leucine amino acid entity, about 0.5 g of the isoleucine amino acid entity, about 0.5 g of the valine amino acid entity, about 1.5 g or about 1.81 of the arginine amino acid entity, about 1.33 g of the glutamine amino acid entity, about 0.15 g or about 0.3 g of the NAC or a salt thereof, about 0.08 g of the L-histidine or a salt thereof, about 0.35 g of the L-lysine or a salt thereof, about 0.08 g of the L-phenylalanine or a salt thereof, and about 0.17 g of the L-threonine or a salt thereof.

According to the invention, any method can be practices with a composition that is a pharmaceutical composition. Thus, the composition can further comprise a pharmaceutically acceptable excipient, such as an excipient that is suitable for oral administration.

More broadly, the invention includes a method for improving muscle function in reduced-mobility or immobilized muscle by reducing fat infiltration, wherein the method comprises administering to a subject in need thereof an effective amount of a composition comprising at least four amino acids, wherein the composition reduces fat infiltration in muscle, e.g., in the reduced-mobility or immobilized muscle. This method can be practiced with a composition that is a pharmaceutical composition. Thus, the composition can further comprise a pharmaceutically acceptable excipient, such as an excipient that is suitable for oral administration. The discovery that such compositions are capable of reducing infiltration of fat in muscle thus allows for determining a degree of fat infiltration in muscle under conditions of reduced-mobility or immobilized muscle. Any method for determining or evaluating the degree of fat infiltration in muscle can be used, e.g., MRI, DEXA, or CT.

In these foregoing method for improving muscle function in reduced-mobility or immobilized muscle by reducing fat infiltration, wherein the composition can comprise:

a) a leucine amino acid entity, an arginine amino acid entity, and a glutamine amino acid entity;

b) a N-acetylcysteine (NAC) entity, e.g., NAC; and c) an essential amino acid (EAA)-entity chosen from a histidine (H)-amino acid-entity, a lysine (K)-amino acid-entity, a phenylalanine (F)-amino acid-entity, and a threonine (T)-amino acid-entity or a combination of two, three, or four of the EAAs. Furthermore:

d) at least one amino acid entity is not provided as a peptide of more than 20 amino acid residues in length. In still another aspect:

(i) the amino acid entity of (a) is selected from Table 1; and (ii) one or both of the arginine amino acid entity and the glutamine amino acid entity are present at a higher amount (wt. %) than the leucine amino acid entity.

In these foregoing method for improving muscle function in reduced-mobility or immobilized muscle by reducing fat infiltration, the subject can have a disease or disorder selected from the group consisting of a rare muscle disease, muscle atrophy, sarcopenia, muscle deterioration, muscle decay, cachexia, drug-induced myopathy, muscular dystrophy, myopenia, muscle weakness, perceived muscle weakness, ICU-acquired myopathy, burns-related myopathy, a neuromuscular disorder, ventilator-induced diaphragmatic dystrophy, hyponatremia, hypokalemia, a calcium deficiency, hypercalcemia, amyotrophic lateral sclerosis, and a bone weakness disease. Alternatively, the subject can have or be identified as having decreased muscle function due to aging, injury, muscle atrophy, infection, disease, stroke, or a fracture or other trauma. The fracture or other trauma may be selected from rotator cuff surgery, knee surgery, hip surgery, joint replacement, injury repair surgery, or the subject has worn a cast. In the case of a fracture or trauma, the subject can receive the composition after the fracture or other trauma or before the fracture or other trauma, in the latter case, e.g., in conjunction with planned elective surgery. For example, the subject may have a rotator cuff injury, and further the subject may have rotator cuff surgery. The invention also provides for determining or evaluating fat infiltration in muscle in the subject to evaluate effectiveness of administration of the composition in treating the disease or disorder, decreased muscle function, or fracture or other trauma, e.g., prior to an elective procedure. According to the invention and exemplified below, determining or evaluating fat infiltration in muscle reveals that a fat fraction in muscle is unchanged from before the treatment, or even improved. As noted above, any method for determining or evaluating the degree of fat infiltration in muscle can be used, e.g., MRI, DEXA, or CT.

In yet another embodiment, the invention provides method for determining whether a composition comprising at least four amino acids is effective in treating a disease or disorder associated with muscle function. This method comprises administering to the subject a composition comprising at least four amino acids and determining whether there is a reduction in fat infiltration in muscle in the subject. Thus, fat infiltration in muscle can serve as a surrogate for muscle function in a study, e.g., a clinical trial, post-marketing trial, prognostic assay, etc. in conjunction with treatment with a composition comprising at least four amino acids. In particular, fat infiltration can be in muscle tissue affected by the disease or disorder associated with muscle function.

Thus, in the situation where the subject has a rotator cuff injury, the method can be used. For example, administration of the composition can precede a surgery for the rotator cuff injury. In this situation, the invention provides for determining a level of fat infiltration in shoulder muscle affected by the rotator cuff injury before surgery. In conjunction with evaluating progression and prognosis, it is also possible to determine a level of fat infiltration in shoulder muscle affected by the rotator cuff injury after surgery.

In the method for determining whether a composition comprising at least four amino acids is effective in treating a disease or disorder associated with muscle function, the subject at risk of fat infiltration in muscle has chronic back pain (fat infiltration in paraspinal muscles); HIV patients (fat infiltration in locomotor muscles); spinal cord injury; stroke; COPD; ESLD, e.g., hepatic encephalopathy, variceal bleeding, portal hypertension, ascites, infection risk, sepsis, all-cause hospitalization, and all-cause and liver-related mortality; and muscle weakness associated with ageing. Alternatively, the method improves a muscle function of sequestering glucose in a subject at risk of fat infiltration in muscle, e.g., if the subject has diabetes or metabolic disease. In yet another alternative, the subject at risk of fat infiltration in muscle has cancer, such as colorectal cancer or periampullary cancer. Moreover, the subject at risk for fat infiltration in muscle may not have significant increase in BMI, sarcopenia, or other overt conditions. Thus, the subject at risk for fat infiltration in muscle may suffer from cirrhosis without sarcopenia, or may have ESLD, e.g., hepatic encephalopathy, variceal bleeding, portal hypertension, ascites, infection risk, sepsis, all-cause hospitalization, and all-cause and liver-related mortality. As noted above, any method for determining or evaluating the degree of fat infiltration in muscle can be used, e.g., MRI, DEXA, or CT.

DETAILED DESCRIPTION

Figure 1:
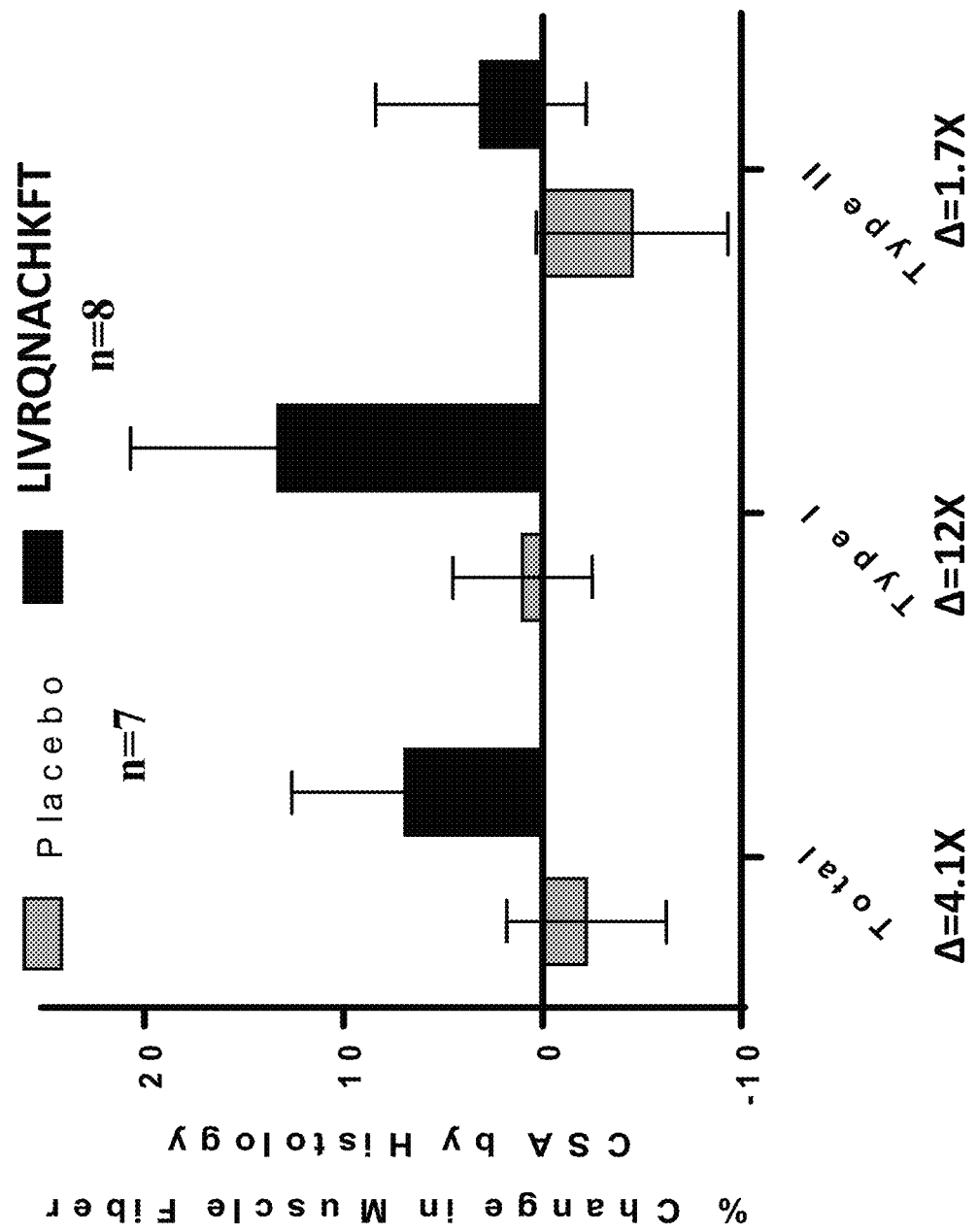
FIG. 1. Change in vastus lateralis cross-sectional area (CSA) and fiber types by histology during limb immobilization (Day 15 vs. Day 8).

The present invention is based on the unprecedented discovery that compositions comprising amino acid entities are capable of reducing fat infiltration in muscle. This discovery provides for treatment of a number of diseases and disorders involving fat infiltration in muscle. In some cases, fat infiltration in muscle results in increased morbidity, worsening of the disease or disorder, or predicts a worse outcome from an intervention such as surgery to repair a torn rotator cuff.

Thus the invention provides, at least in part, methods of reducing fat infiltration in muscle by administering an Active Moiety composition of the invention, which is a composition comprising at least four different amino acid entities. In some cases, the invention further comprises determining or evaluating the extent or degree of infiltration of fat in muscle, e.g., as a diagnostic, a prognostic indicator, to evaluate progress of the disease or disorder with or without treatment, or as a surrogate of muscle health, or any combination of the foregoing. Various techniques are available for determining the extent of infiltration of fat in muscle. The most rigorous techniques are computed tomograph (CT) and magnetic resonance imaging (MRI).

The methods of reducing fat infiltration in muscle may also provide a method of treating any or all of immobilization, malnutrition, fasting, aging, autophagy, reduced protein synthesis, anabolic resistance, junction integrity (e.g., neuromuscular junction integrity), insulin resistance, decreased mitochondrial biogenesis, an energy deficit, or anaplerosis in a subject that includes administering to a subject in need thereof an effective amount of a pharmaceutical composition including defined amino acid components. In some embodiments, the subject has a rare muscle disease. In some embodiments, the subject has sarcopenia, muscle deterioration, decay, atrophy, cachexia, drug-induced myopathy, muscular dystrophy, or myopenia. In some embodiments, the subject has a fracture or other trauma. In some embodiments, the subject has a drug-induced myopathy. In some embodiments, the subject has a statin-induced myopathy. In some embodiments, the subject has a steroid-induced myopathy. In some embodiments, the subject has an immunosuppressant-induced myopathy. In some embodiments, the subject has a chemotherapeutic-induced myopathy. In some embodiments, the subject has an alcohol-induced myopathy.

In addition to evaluating or determining the extent of fat infiltration in muscle, improvements in muscle function can be assessed by performing metrics selected from maximal isometric knee strength test (e.g., to determine changes in muscle strength), muscle biopsy (e.g., to determine muscle fiber quality), and electrical impedance myography (EIM) (e.g., to determine muscle health, such as resistive and capacitive properties of muscle tissue and sensitivity to disuse-related atrophy), or other standard clinical performance assessments such as the Short Performance Physical Battery (SPPB), Harris Hip Score and others.

In some embodiments, the composition is for use as a medicament in improving muscle function in a subject at risk of or experiencing fat infiltration in muscle. In some embodiments, the composition is for use as a medicament in treating a muscle disease or disorder involving fat infiltration in the muscle in a subject.

In some embodiments, the composition is for use in the manufacture of a medicament for improving muscle function in a subject. at risk of or experiencing fat infiltration in muscle. In some embodiments, the composition is for use in the manufacture of a medicament for treating a muscle disease or disorder involving fat infiltration in the muscle in a subject.

Additionally, the composition may be useful as a dietary supplement, e.g., a nutritional supplement, dietary formulation, functional food, medical food, food, or beverage comprising a composition described herein. Another embodiment provides a nutritional supplement, dietary formulation, functional food, medical food, food, or beverage comprising a composition described herein for use in the management of any of the diseases or disorders described herein.

One embodiment provides a method of maintaining or improving muscle health, muscle function, muscle functional performance, or muscle strength, comprising administering to a subject an effective amount of a composition described herein to reduce fat infiltration in muscle in the subject. Another embodiment provides a method of providing nutritional support or supplementation to a subject suffering from muscle atrophy comprising administering to the subject an effective amount of a composition described herein to reduce fat infiltration in muscle in the subject. Yet another embodiment provides a method of providing nutritional support or supplementation that aids in the management of muscle atrophy to a subject comprising administering to the subject in need thereof an effective amount of a composition described herein to reduce fat infiltration in muscle in the subject.

Definitions

Terms used in the claims and specification are defined as set forth below unless otherwise specified.

It must be noted that, as used in the specification and the appended claims, the singular forms "a," "an" and "the" include plural referents unless the context clearly dictates otherwise.

The term "fat infiltration in muscle" means an increase in the fat fraction of muscle below the muscle fascia, as distinguished from subcutaneous fat. For example, fat found in the deep fascia of the thigh is fat infiltration in muscle. Various publications use terms such as intramuscular fat fraction, intermuscular fat infiltration, intramuscular fat, intermuscular fat, intermuscular adipose tissue (IMAT), and myosteatosis or myostasis. All of these terms refer to fat (visible storage of lipids in adipocytes) located between muscle fibers and between muscle groups, or within myocytes themselves. Fat that has infiltrated in muscle appears to have some of the same characteristic as ectopic or visceral fat, e.g., fat in liver or other organs, or in the abdomen.

"Reduction of fat infiltration in muscle" means that the degree or extent of fat infiltration in a subject, e.g., to muscle that is immobilized, injured, or otherwise subject to muscle infiltration, is less than it would have been in the absence of an intervention, i.e., in the absence of administering an Active Moiety to the subject. Thus, the fat fraction in the muscle is lower than it would have otherwise been. In one example, administration of an Active Moiety reduces fat infiltration in muscle by 100%, i.e., it prevents it. However, the invention includes any reduction in fat infiltration that would occur in the absence of treatment with an Active Moiety. Preferably reduction of fat infiltration in muscle is detectable. More preferably it is significant, e.g., reaches statistical significance in a population of subjects in a controlled study.

The term "fat fraction" or "FF" refers to the fraction of fat or percentage of fat in a limb, part of a limb, or body (taking the entire volume of the limb, part of a limb, or body as the whole or 100%). Similarly, the muscle mass is the fraction of muscle or percentage of muscle in limb, part of a limb, or body.

In the Example described below, images depicting fat fraction (FF) show that in a subject administered placebo, the subject's non-immobilized leg had no change in FF, while the subject's immobilized leg had increased FF and decreased muscle mass. By contrast, in a subject administered an Active Moiety, the immobilized leg had lower fat fraction and a higher muscle content following immobilization compared to placebo. These FF changes were quantified across all subjects. Percent change in quadriceps muscle fat fraction increased more that 10% in subjects who received placebo, compared to about 0% in subjects who received Active Moiety.

The term "subject" refers to a human person, and can include, but is not limited to, a patient, i.e., a person who is under care of a healthcare provider (doctor, nurse practitioner, etc.). It can also mean a person in a clinical study, or a person who self-diagnoses and self-treats, or a subject who receives a dietary supplement (as broadly defined above).

As used herein, the term "Active Moiety" means a combination of four or more amino acid entities that, in aggregate, have a physiological effect. In some cases, the physiological effect can be a therapeutic effect involving reduction of fat infiltration into muscle, as defined below. For example, an Active Moiety can rebalance a metabolic dysfunction in a subject suffering from a disease or disorder. An Active Moiety of the invention can contain other biologically active ingredients. In some examples, the Active Moiety comprises a defined combination of four or more amino acid entities, as set out in detail below. The individual amino acid entities are present in the Active Moiety in various amounts or ratios, which can be presented as amount by weight (e.g., in grams), ratio by weight of amino acid moieties to each other, amount by mole, amount by dry weight percent of the Active Moiety, amount by mole percent of the Active Moiety, caloric content, percent caloric contribution to the Active Moiety, etc. Generally, this disclosure will provide grams of amino acid entity in a dosage form, weight percent of an amino acid moiety relative to the weight of the Active Moiety, i.e., the weight of all the amino acid moieties and any other biologically active ingredient present in the Active Moiety, or in ratios. The abbreviation "wt." means weight.

As used herein, the term "amino acid entity" refers to an amino acid in one or both of free form or salt form, an amino acid residue of a peptide (e.g., of a dipeptide, tripeptide, or polypeptide of 20 amino acids or less in length), a derivative of an amino acid, a precursor of an amino acid, or a metabolite of an amino acid (see, e.g., Table 1). Accordingly, the term "XXX amino acid entity" refers to an amino acid entity that if a free amino acid, comprises free XXX or XXX in salt form; if a peptide, refers to a peptide comprising an XXX residue; if a derivative, refers to a derivative of XXX; if a precursor, refers to a precursor of XXX; and if a metabolite, refers to a XXX metabolite. For example, where XXX is leucine, then leucine amino acid entity refers to free leucine or leucine in salt form, a peptide of less than 20 amino acids comprising a leucine residue, a leucine derivative, a leucine precursor, or a metabolite of leucine (where such derivative, precursor, or metabolite achieves the same physiological effect as leucine); where XXX is arginine, then arginine amino acid entity refers to free arginine or arginine in salt form, a peptide of less than 20 amino acids comprising an arginine residue, an arginine derivative, an arginine precursor, or a metabolite of arginine (where such derivative, precursor, or metabolite achieves the same physiological effect as arginine); where XXX is glutamine, then glutamine amino acid entity refers to free glutamine or glutamine in salt form, a peptide of less than 20 amino acids comprising a glutamine residue, a glutamine derivative, a glutamine precursor, or a metabolite of glutamine (where such derivative, precursor, or metabolite achieves the same physiological effect as glutamine); where XXX is N-acetylcysteine (NAC), then NAC-amino acid entity refers to free NAC or NAC in salt form, a peptide comprising a NAC residue, a NAC derivative, a NAC precursor, or a metabolite of NAC (where such derivative, precursor, or metabolite achieves the same physiological effect as NAC); where XXX is histidine (H), then histidine amino acid entity refers to free histidine or histidine in salt form, a peptide of less than 20 amino acids comprising a histidine residue, a histidine derivative, a histidine precursor, or a metabolite of histidine (where such derivative, precursor, or metabolite achieves the same physiological effect as histidine); where XXX is lysine, then lysine amino acid entity refers to free lysine or lysine in salt form, a peptide of less than 20 amino acids comprising a lysine residue, a lysine derivative, a lysine precursor, or a metabolite of lysine (where such derivative, precursor, or metabolite achieves the same physiological effect as lysine); where XXX is phenylalanine, then phenylalanine amino acid entity refers to free phenylalanine or phenylalanine in salt form, a peptide of less than 20 amino acids comprising a phenylalanine residue, a phenylalanine derivative, a phenylalanine precursor, or a metabolite of phenylalanine (where such derivative, precursor, or metabolite achieves the same physiological effect as phenylalanine); or where XXX is threonine, then threonine amino acid entity refers to free threonine or threonine in salt form, a peptide of less than 20 amino acids comprising a threonine residue, a threonine derivative, a threonine precursor, or a metabolite of threonine (where such derivative, precursor, or metabolite achieves the same physiological effect as threonine). Where the biological system provides for isomerization of a D-amino acid to the L-form, the D-amino acid can be an amino acid entity.

Salts of amino acids include any physiologically tolerable, e.g., ingestible, salt. For pharmaceutical compositions, the salt form of an amino acid present in the Active Moiety should be a pharmaceutically acceptable salt. In a specific example, the salt form is the hydrochloride (HCl) salt form of the amino acid.

In some embodiments, the derivative of an amino acid entity comprises an amino acid ester (e.g., an alkyl ester, e.g., an ethyl ester or a methyl ester of an amino acid entity) or a keto-acid.

TABLE 1

Amino acid entities include amino acids, precursors, metabolites, and derivatives of the compositions described herein.

| | Exemplary Amino Acid | Precursors | Metabolites | Derivatives |
|---|---|---|---|---|
| L | L-Leucine | Oxo-leucine | HMB (beta-hydroxy-beta-methybutyrate); Oxo-leucine; Isovaleryl-CoA | N-Acetyl-Leucine |
| I | L-Isoleucine | 2-Oxo-3-methyl-valerate; | 2-Oxo-3-methyl-valerate; Methylbutyrl-CoA | N-Acetyl-Isoleucine |
| V | L-Valine | 2-Oxo-valerate | Isobutryl-CoA | N-Acetyl-Valine |
| R | L-Arginine | Argininosuccinate; Aspartate; Glutamate | Agmatine; Creatine | N-Acetyl-Arginine; |
| Q | L-Glutamine | Glutamate | Carbamoyl-P; Glutamate | N-Acetyl-Glutamine; |
| NAC | N-Acetylcysteine | Acetylserine; Cystathionine; | Glutathione; Cystathionine; Homocysteine; Methionine | Cystine; Cysteamine |
| H | L-Histidine | Histidinol; Histidinal; Ribose-5-phosphate | Carnosine; Histamine; Urocanate | N-Acetyl-Histidine |
| K | L-Lysine | Diaminopimelate; Aspartate | Trimethyllysine; Saccharopine | N-Acetyl-Lysine |
| F | L-Phenylalanine | Phenylpyruvate | Tyrosine | N-Acetyl-Phenylalanine |
| T | L-Threonine | Homoserine; O-PhosphoHomoserine | Oxobutyrate | N-Acetyl-Threonine |

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

An "amino acid" refers to an organic compound having an amino group (—NH$_2$), a carboxylic acid group (—C(=O)OH), and a side chain bonded through a central carbon atom, and includes essential and non-amino acids, as well as natural and unnatural amino acids.

The proteogenic amino acids, shown below, are known by three- and one-letter abbreviations in addition to their full names. For a given amino acid, these abbreviations are used interchangeably herein. For example, Leu, L or leucine all refer to the amino acid leucine; Ile, I or isoleucine all refer to the amino acid isoleucine; Val, V or valine all refer to the amino acid valine; Arg, R or arginine all refer to the amino acid arginine; and Gln, Q or glutamine all refer to the amino acid glutamine. Likewise, the non-natural amino acid derivative N-acetylcysteine may be referred to interchangeably by "NAC" or "N-acetylcysteine." Amino acids may be present as L-isomers of amino acids to ensure physiological activity.

TABLE 2

Canonical (proteogenic) amino acid names and abbreviations

| Amino acid (L isomer) | Three-letter | One-letter |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

A "branched chain amino acid" is an amino acid selected from leucine, isoleucine, and valine.

The term "effective amount" as used herein means an amount of an Active Moiety, or pharmaceutical composition comprising an Active Moiety, which is sufficient enough to significantly and positively modify the symptoms and/or conditions to be treated (e.g., provide a positive clinical response). The effective amount of an active ingredient for use in a pharmaceutical composition will vary with the particular condition being treated, the severity of the condition, the duration of treatment, the nature of concurrent therapy, the particular active ingredient(s) being employed, the particular pharmaceutically-acceptable excipient(s) and/or carrier(s) utilized, and like factors with the knowledge and expertise of the attending physician.

A "pharmaceutical composition" described herein comprises at least one amino acid and a pharmaceutically acceptable carrier or excipient. In some embodiments, the pharmaceutical composition is used as a therapeutic, a nutraceutical, a medical food, or as a supplement.

The term "pharmaceutically acceptable" as used herein, refers to amino acids, materials, excipients, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "therapeutic effect" means a beneficial clinical effect. A beneficial clinical effect can be shown by lessening the progression of a disease and/or alleviating one or more symptoms of the disease. Preferably, the beneficial clinical effect is statistically significant.

A "health effect" in the context of a food supplement means that there is some benefit to the normal structure or function of a human or target organ in a human.

A "unit dose" or "unit dosage" as used herein means an amount or dose of medicine prepared in an individual packet or container for convenience, safety, or monitoring. A "unit dose" or "unit dosage" comprises the drug product or drug products in the form in which they are marketed for use, with a specific mixture of active ingredients and inactive components (excipients), in a particular configuration (such as a capsule shell, for example), and apportioned into a particular dose.

As used herein, the terms "treat," "treating," or "treatment" refer in one embodiment, to ameliorating a disease or disorder of fat infiltration in muscle (i.e., slowing or arresting or reducing the development of the disease or disorder or at least one of the clinical symptoms thereof). In another embodiment, "treat," "treating," or "treatment" refers to alleviating or ameliorating at least one physical parameter of fat infiltration in muscle, including those which may not be discernible by the patient. In yet another embodiment, "treat," "treating," or "treatment" refers to modulating a symptom of a disease or disorder of fat infiltration in muscle. In yet another embodiment, "treat," "treating," or "treatment" refers to preventing or delaying the onset or development or progression of a disease or disorder of fat infiltration in muscle.

Active Moieties: Compositions of Amino Acid Entities

US Patent Publication No. 2018/0207119, filed Dec. 19, 2017, entitled AMINO ACID COMPOSITIONS AND METHODS FOR THE TREATMENT OF MUSCLE DISEASES AND DISORDERS, and U.S. patent application Ser. No. 15/847,289, filed Dec. 19, 2017, entitled AMINO ACID COMPOSITIONS AND METHODS FOR THE TREATMENT OF LIVER DISEASES, each of which is specifically incorporated herein by reference in its entirety, disclose compositions of amino acid entities, i.e., Active Moieties, which may reduce fat infiltration in muscle, as can be shown by the methods herein described.

In some embodiments, the composition comprises a leucine amino acid entity, an arginine amino acid entity, a glutamine amino acid entity; and an antioxidant or reactive oxygen species (ROS) scavenger (e.g., a N-acetylcysteine (NAC) entity, e.g., NAC).

In some embodiments, the composition further comprises one or more essential amino acid (EAA)-entities. In some embodiments, the EAA-entities are chosen from one, two, three, or more (e.g., all) of a histidine (H)-amino acid-entity, a lysine (K)-amino acid-entity, a phenylalanine (F)-amino acid-entity, and a threonine (T)-amino acid-entity.

In some embodiments, the composition is capable of improving one or more physiological symptoms selected from immobilization, malnutrition, fasting, aging, autophagy, reduced protein synthesis, anabolic resistance, neuromuscular junction integrity, insulin resistance, decreased mitochondrial biogenesis, anaplerosis, myogenesis, or an energy deficit.

As already noted, the present disclosure provides compositions that can include a leucine amino acid entity, an arginine amino acid entity, a glutamine amino acid entity; and an antioxidant or reactive oxygen species (ROS) scavenger, e.g., a N-acetylcysteine (NAC) entity, e.g., NAC. In some embodiments, the total weight of the leucine amino acid entity, arginine amino acid entity, glutamine amino acid entity; and ROS scavenger, e.g., a N-NAC entity, e.g., NAC, can be greater than the total wt. of other amino acid entities in the composition (e.g., Active Moiety).

In certain embodiments, two, three, or more (e.g., all) of methionine (M), tryptophan (W), valine (V), or cysteine (C) may be absent from the composition (e.g., Active Moiety), or if present, are present at less than 1 weight (wt.) %, less than 0.5 wt. %, or less than 0.1 wt. %, each of the foregoing on a dry weight basis. In some embodiments, methionine, tryptophan, valine, or cysteine, if present, may be present in an oligopeptide, polypeptide, or protein, with the proviso that the protein is not whey, casein, lactalbumin, or any other protein used as a nutritional supplement, medical food, or similar product, whether present as intact protein or protein hydrolysate.

In some embodiments, one or both of the arginine amino acid entity and the glutamine amino acid entity are present at a higher amount (wt. %) than the leucine amino acid entity. The arginine amino acid entity can be present, e.g., at an amount of at least 2 wt. %, at least 3 wt. %, at least 4 wt. %, at least 5 wt. %, at least 6 wt. %, at least 7 wt. %, or at least 8 wt. % greater than the leucine amino acid entity. The glutamine amino acid entity can be present, e.g., at an amount of at least 2 wt. %, at least 3 wt. %, at least 4 wt. %, or at least 5 wt. % greater than the L-leucine amino acid entity.

The weight ratio of a particular amino acid or particular amino acids in a composition or mixture of amino acids, i.e., in an Active Moiety, is the ratio of the weight of the particular amino acid or amino acids in the composition or mixture compared to the total weight of amino acids present in the composition or mixture. This value is calculated by dividing the weight of the particular amino acid or of the particular amino acids in the composition or mixture by the weight of all amino acids present in the composition or mixture and multiplying times 100. Percent weight on a dry weight basis refers to the percent weight of solid materials, which is relevant because as exemplified herein the Active Moiety composition may be dissolved or suspended in a liquid, particularly water, which provides considerable additional weight to a final liquid formulation.

The Active Moiety may further comprise additional branched-chain amino acid (BCAA)-entities, e.g., one or both of an isoleucine amino acid-entity and a valine amino acid-entity; alternatively, both the isoleucine amino acid-entity and the valine amino acid-entity are present. The leucine amino acid entity can be present at a higher amount (% by weight) than one or both of the isoleucine amino acid-entity and the valine amino acid-entity (e.g., the leucine entity is present at an amount of at least 10 wt. %, at least 15 wt. %, at least 20 wt. %, at least 25 wt. %, at least 30 wt. %, at least 35 wt. %, at least 40 wt. %, at least 45 wt. %, or at least 50 wt. % greater than one or both of the isoleucine amino acid-entity and the valine amino acid-entity).

The composition can further comprise one or more essential amino acid (EAA)-entities. In certain embodiments the EAA-entities are chosen from one, two, three, or four of a histidine amino acid-entity, a lysine amino acid-entity, a phenylalanine amino acid-entity, and a threonine amino acid-entity.

If present, the histidine amino acid-entity can be present in an amount of at least 0.5 wt. %, at least 0.6 wt. %, at least 0.7 wt. %, at least 0.8 wt. %, at least 0.9 wt. %, at least 1.0 wt. %, at least 1.1 wt. %, at least 1.2 wt. %, at least 1.3 wt. % or at least 1.4 wt. % of the composition on a dry weight basis.

If present, the lysine amino acid-entity can be present in amount of at least 2 wt. %, at least 3 wt. %, at least 4 wt. %, at least 5 wt. %, or at least 6 wt. % of the composition on a dry weight basis.

If present, the phenylalanine amino acid-entity can be present in an amount of at least 0.5 wt. %, at least 0.6 wt. %, at least 0.7 wt. %, at least 0.8 wt. %, at least 0.9 wt. %, at least 1.0 wt. %, at least 1.1 wt. %, at least 1.2 wt. %, at least 1.3 wt. % or at least 1.4 wt. % of the composition on a dry weight basis.

If present, the threonine amino acid-entity can be present in amount of at least 0.5 wt. %, at least 1 wt. %, at least 1.5 wt. %, at least 2 wt. %, at least 2.5%, or at least 3 wt. % of the composition on a dry weight basis.

The histidine amino acid entity, lysine amino acid entity, phenylalanine amino acid entity, and threonine amino acid entity can all be present in the composition, including in the wt. % set forth in the preceeding four paragraphs.

The weight (wt.) ratio of the leucine amino acid entity, the arginine amino acid entity, the glutamine amino acid entity, and the NAC-amino acid entity in the Active Moiety can be about 1-3:2-4:2-4:0.1-2.5. In certain embodiments, the wt. ratio of the leucine amino acid entity, the arginine amino acid entity, the glutamine amino acid entity, and the NAC-amino acid entity is about 2:3:2.66:0.3. In certain embodiments, the wt. ratio of the leucine amino acid entity, the arginine amino acid entity, the glutamine amino acid entity, and the NAC-amino acid entity is about 2:3:2.66:0.6.

In some embodiments, the composition comprises a ratio of branched-chain amino acids to total amino acids of about 4:7 to about 1:2.

In some embodiments, the wt. ratio of the leucine amino acid entity, the isoleucine amino acid entity, the valine amino acid entity, the arginine amino acid entity, the glutamine amino acid entity, the NAC-amino acid entity, the histidine amino acid entity, the lysine amino acid entity, the phenylalanine amino acid entity, and the threonine amino acid entity is about 1-3:0.5-1.5:0.5-1.5:2-4:2-4:0.1-0.5:0.1-0.5:0.2-1.0:0.1-0.5:0.2-0.7. In certain embodiments, the wt. ratio of the leucine amino acid entity, the isoleucine amino acid entity, the valine amino acid entity, the arginine amino acid entity, the glutamine amino acid entity, the NAC-amino acid entity, the histidine amino acid entity, the lysine amino acid entity, the phenylalanine amino acid entity, and the threonine amino acid entity is about 2.0:1.0:1.0:3.0:2.66:0.3:0.16:0.7:0.16:0.34. In certain embodiments, the wt. ratio of the leucine amino acid entity, the isoleucine amino acid entity, the valine amino acid entity, the arginine amino acid entity, the glutamine amino acid entity, the NAC-amino acid entity, the histidine amino acid entity, the lysine amino acid entity, the phenylalanine amino acid entity, and the threonine amino acid entity is about 2.0:1.0:1.0:3.0:2.66:0.3:0.16:0.7:0.16:0.68.

In some embodiments, the total wt. of amino acids present in a unit dose of an Active Moiety is between about 4 g and about 80 g. In certain embodiments, the total wt. of amino acids present is about 6 g, about 18 g, about 24 g, about 48 g, about 68 g, or about 72 g in a unit dose of an active moiety. In an example, a unit dose of the Active Moiety comprises at least 1 g of the leucine amino acid entity, at least 0.5 g of the isoleucine amino acid entity, at least 0.5 g of the valine amino acid entity, at least 1.5 g of the arginine amino acid entity, at least 1.33 g of the glutamine amino acid entity, at least 0.15 g of the NAC-amino acid entity, at least 0.08 g of the histidine amino acid entity, at least 0.35 g of the lysine amino acid entity, at least 0.08 g of the phenylalanine amino acid entity, and at least 0.17 g of the threonine amino acid entity. In some embodiments, the composition comprises at least 1 g of the leucine amino acid entity, at least 0.5 g of the isoleucine amino acid entity, at least 0.5 g of the valine amino acid entity, at least 1.5 g of the arginine amino acid entity, at least 1.33 g of the glutamine amino acid entity, at least 0.3 g of the NAC-amino acid entity, at least 0.08 g of the histidine amino acid entity, at least 0.35 g of the lysine amino acid entity, at least 0.08 g of the phenylalanine amino acid entity, and at least 0.17 g of the threonine amino acid entity. Alternatively, the foregoing Active Moiety comprises 0.3 g of NAC instead of 0.15 g. Multiples of all these amounts in unit doses of the Active Moiety are also contemplated, e.g., 2-fold, 3-fold, 4-fold, 5-fold, 6-fold, etc.

Preferably, at least one amino acid entity is a free amino acid, e.g., one or more (e.g., all) amino acid entities are a free amino acid. In some embodiments, the leucine amino acid entity, the arginine amino acid entity, the glutamine amino acid entity, and the NAC-amino acid entity is a free amino acid entity. In certain embodiment, the leucine amino acid entity, the isoleucine amino acid entity, the valine amino acid entity, the arginine amino acid entity, the glutamine amino acid entity, and the NAC-amino acid entity a free amino acid. In certain embodiments, the leucine amino acid entity, the isoleucine amino acid entity, the valine amino acid entity, the arginine amino acid entity, the glutamine amino acid entity, the NAC-amino acid entity, the histidine amino acid entity, the lysine amino acid entity, the phenylalanine amino acid entity, and the threonine amino acid entity is a free amino acid.

Alternatively, at least one amino acid entity is in a salt form, e.g., one or more (e.g., all) of the amino acid entities is in a salt form. In some embodiments, wherein the leucine amino acid entity, the arginine amino acid entity, the glutamine amino acid entity, and the NAC-amino acid entity is in a salt form. In certain embodiments, the leucine amino acid entity, the isoleucine amino acid entity, the valine amino acid entity, the arginine amino acid entity, the glutamine amino acid entity, and the NAC-amino acid entity is in a salt form. In certain embodiments, the leucine amino acid entity, the isoleucine amino acid entity, the valine amino acid entity, the arginine amino acid entity, the glutamine amino acid entity, the NAC-amino acid entity, the histidine amino acid entity, the lysine amino acid entity, the phenylalanine amino acid entity, and the threonine amino acid entity is in a salt form.

In some embodiments, the Active Moiety comprises a combination of 4 to 20 different amino acid entities, e.g., 5 to 15 different amino acid entities. In other embodiments, the Active Moiety consists of 4 to 16 different amino acid entities; more particularly, 5 to 15 different amino acid entities. For example, the Active Moiety can further comprise one or more (e.g., all) or more of serine, glycine, glutamine, HMB, citrulline, glutamine, L-cysteine, cystine, or glutathione.

In some embodiments, the composition comprises arginine, glutamine, N-acetylcysteine; a BCAA chosen from one, two, or all of leucine, isoleucine, and valine; and an essential amino acid EAA chosen from one, two, or all of histidine, lysine, phenylalanine, and threonine.

An aspect of the present disclosure provides a composition comprising an Active Moiety comprised of free amino acids and one or more pharmaceutically acceptable excipients, such that the amino acids include leucine, isoleucine, valine, arginine, glutamine, N-acetylcysteine, histidine, lysine, phenylalanine, and threonine.

An aspect of the present disclosure provides a composition comprising an Active Moiety consisting of free amino acids and one or more pharmaceutically acceptable excipients, such that the amino acids consist of leucine, isoleucine, valine, arginine, glutamine, N-acetylcysteine, histidine, lysine, phenylalanine, and threonine.

An exemplary Active Moiety can include leucine, isoleucine, valine, arginine HCl, glutamine, N-acetylcysteine, histidine, lysine, phenylalanine, and threonine as its defined amino acid components in a wt. ratio of 2.0:1.0:1.0:3.62: 2.66:0.3:0.16:0.7:0.16:0.34 (Table 3). The Active Moiety can include leucine, isoleucine, valine, arginine, glutamine, N-acetylcysteine, histidine, lysine, phenylalanine, and threonine as its defined amino acid components in a wt. ratio of 2.0:1.0:1.0:3.0:2.66:0.3:0.16:0.7:0.16:0.34.

TABLE 3

Exemplary amino acid components of the composition.

| Amino acid | weight ratio | g/ packet | g/ dose 1 | Total g daily dose 1 | g/ dose 2 | Total g daily dose 2 |
|---|---|---|---|---|---|---|
| Leucine | 2.0 | 1.0 | 1.0 | 3 | 4 | 12 |
| Isoleucine | 1.0 | 0.5 | 0.5 | 1.5 | 2 | 6 |
| Valine | 1.0 | 0.5 | 0.5 | 1.5 | 2 | 6 |
| Arginine HCl | 3.62 | 1.81 | 1.81 | 5.43 | 7.24 | 21.72 |
| Glutamine | 2.66 | 1.33 | 1.33 | 3.99 | 5.32 | 15.96 |
| N-acetyl-cysteine | 0.3 | 0.15 | 0.15 | 0.45 | 0.6 | 1.8 |
| Histidine | 0.16 | 0.08 | 0.08 | 0.24 | 0.32 | 0.96 |
| Lysine | 0.7 | 0.35 | 0.35 | 1.05 | 1.4 | 4.2 |
| Phenylalanine | 0.16 | 0.08 | 0.08 | 0.24 | 0.32 | 0.96 |
| Threonine | 0.34 | 0.17 | 0.17 | 0.51 | 0.68 | 2.04 |
| Total amino acids | | ~6 g | ~6 g | ~18 g | ~24 g | ~72 g |

The composition can be administered in packets, e.g., packets containing about 6 g total amino acids as exemplified.

The composition can be administered three times daily at a dose of about 6 g of Active Moiety, i.e., total amino acids. In some embodiments, about 18 g, about 22, about 24 g, about 68 g or about 72 g total amino acids is administered per day. In an example, the composition is administered three times daily at a dose of about 24 g total amino acids for a total of about 72 g total amino acids is administered per day.

Methods of Treatment with an Active Moiety to Reduce Fat Infiltration in Muscle

The Active Moiety composition as described herein can be administered to reduce fat infiltration in muscle. Fat infiltration in muscle is an important predictor of muscle function and mobility, independent of as well as associated with other diseases and disorders of muscle atrophy (see, e.g., Addison et al., 2014, Int. J. Endocrinology, dx.doi.org/10.1155/2014/309570) and has been identified as a complication of cirrhosis independently of other co-morbidities, e.g., sarcopenia (see, e.g., Bhanji et al., 2018, Hep. Intl., doi.org/10.1007/s12072-018-9875-9). Fat infiltration has an impact on muscle quality, so identification of a therapeutic that can reduce fat infiltration in muscle is an important development. As shown in the Example, an exemplary Active Moiety, containing LIVRQNacHFKT (using the single amino acid code with Nac meaning NAC as described above), showed significant reduction or even avoidance of fat infiltration in muscle that was immobilized for just seven days. This unprecedented observation for this class of active combinations of amino acid entities now identified as Active Moieties opens important new avenues of therapy with an Active Moiety for subjects in need of therapy, as well as methods of monitoring the effect of administration of an Active Moiety.

Thus, a method of the invention includes administration of an Active Moiety to treat subjects at risk of or who have fat infiltration in muscle, such as but not limited to subjects with chronic back pain (fat infiltration in paraspinal muscles); HIV patients (fat infiltration in locomotor muscles); spinal cord injury; stroke; COPD; hepatic encephalopathy; and muscle weakness associated with ageing.

In addition, lowering muscle fat is a means of improving glucose handling. Given a strong association between insulin resistance and muscle fat, lowering muscle fat improves glucose sensitivity. Glucose disposal is a function of muscle and so lowering fat infiltration in muscle improve a muscle function of sequestering glucose.

Increased infiltration by inter- and intramuscular fat (myosteatosis), in conjunction with reduced muscle mass (myopenia), is recognized as a poor prognostic indicator in patients with cancer (Malietzis et al., Ann Surg. 2016 February; 263(2):320-5). Significantly shorter cancer-specific survival and overall survival times were identified for the myosteatosis versus the nonmyosteatosis group in a study of patients who underwent curative colorectal cancer surgery (Sueda et al., Dis Colon Rectum. 2018 March; 61(3):364-374). Myosteatosis, characterized by inter- and intramyocellular fat deposition, is strongly related to poor overall survival after surgery for periampullary cancer (https://doi.org/10.1016/j.hpb.2018.02.378). Thus, in another embodiment, reduction of fat infiltration in muscle by administration of an Active Moiety improves outcomes for treatment of cancer, such as surgery for colorectal cancer and for periampullary cancer.

Myosteatosis is independently associated with end-stage liver disease (ESLD), which is inclusive of, but not limited to, hepatic encephalopathy, variceal bleeding, portal hypertension, ascites, infection risk, sepsis, all-cause hospitalization, and all-cause and liver-related mortality.

Subjects who have increased levels of fat infiltration in muscle may not have significant increase in BMI, sarcopenia, or other overt conditions. Accordingly, the invention provides a method of treating a patient who suffers from cirrhosis without sarcopenia by administering an effective amount of an Active Moiety that reduces fat infiltration in muscle. In another aspect, the invention provides for treating a patient with hepatic encephalopathy by administering an effective amount of an Active Moiety that reduces fat infiltration in muscle.

Patients with rotator cuff injury particularly benefit from the methods of the invention of administering an Active Moiety. Fat infiltration in the shoulder muscles is associated with poor outcome from rotator cuff injury (Melis et al., 2009, Orthopaedics & Tramatology: Surgery & Research 95:319-324). Rotator cuff injury includes tendon lesion of the supraspinatus, infraspinatus, and subscapularis. Fat infiltration can occur in any of the affected muscles. Fat infiltration above stage 2 (intermediate) according to the Goutallier classification (see Melis et al.) carries the risk of irreversible functional loss, and a key objective of an intervention during intermediate stages of muscle fatty infiltration is to prevent such permanent loss. Thus, the present invention provides for treating subjects suffering from rotator cuff injury with an Active Moiety to prevent or delay onset of Goutallier Stage 2 fat infiltration, especially prior to surgery to repair the injury. Alternatively, the present invention provides for treating subjects suffering from rotator cuff injury who have Goutallier Stage 2 or greater fat infiltration to reduce the degree of fat infiltration, and thus the Goutallier Stage, prior to surgery. In yet another alternative, the invention provides for treating a subject suffering from a rotator cuff injury with an Active Moiety in addition to medical treatment; medical treatment of rotator cuff injury includes rest, adaptation of daily and occupational movements, rehabilitation, NSAIDS, antalgics, physical therapy, infiltrations, etc. Usually surgery for a rotator cuff injury is surgery to repair a torn tendon, and can be arthroscopic surgery or normal surgery.

The invention is especially useful for treating elderly subjects with a rotator cuff injury, who are at greater risk for more faster fat infiltration and progression to the intermediate Goutallier Stage 2 and beyond to more severe fat infiltration (Stages 3 and 4). Elderly subjects 50 years old or older benefit; subjects 55 years old or older can have even greater benefit; and subjects 60 years old or older even greater benefit than those who are 55 or older, since at each advanced age group susceptibility to fat infusion increases.

Each of the foregoing treatments of rotator cuff injury may include determining the degree of fat infiltration in muscle, e.g., to determine the Goutallier stage; to show changes in Goutallier stage with therapy by administering an Active Moiety of the invention; to obtain a prognosis of therapy, such as surgery; to establish an appropriate time for surgery; or to determine that surgery is unnecessary.

Treatment with an Active Moiety Accompanied by Evaluating Fat Infiltration in Muscle In other conditions, administering the Active Moiety to improve, e.g., enhance, muscle function, e.g., in a patient with a muscle disease or disorder, includes evaluating fat infiltration in muscle. The present disclosure also provides a method for treating one or more (e.g., all) physiological symptoms selected from immobilization, malnutrition, fasting, aging, autophagy, reduced protein synthesis, anabolic resistance, neuromuscular junction integrity, insulin resistance, decreased mitochondrial biogenesis, anaplerosis, or an energy deficit, in each case along with evaluating fat infiltration in muscle. The method includes administering to a subject in need thereof an effective amount of a composition as set forth hereinabove. Therapeutic treatment according to the invention can be achieved in a subject who has a muscle disease, for example, muscle atrophy, sarcopenia, muscle deterioration, muscle decay, cachexia, drug-induced myopathy, muscular dystrophy, or myopenia. The muscle disease or disorder can be a dystrophy, such as a myotonic dystrophy. For example, the muscle disease or disorder can be DM1.

Alternatively, the muscle disease or disorder can be a drug-induced myopathy, e.g., a statin-induced myopathy; a steroid-induced myopathy; an immunosuppressant-induced myopathy; a chemotherapeutic-induced myopathy; or an alcohol-induced myopathy. In each case, administration of an Active Moiety is accompanied by evaluating fat infiltration in muscle.

In addition, the subject can have a fracture or other trauma other than rotator cuff injury.

In some embodiments, the method includes administering to a subject in need thereof an effective amount of the composition to treat a food deficiency, e.g., malnutrition or fasting; aging; autophagy; reduced protein synthesis; anabolic resistance; junction integrity (e.g., neuromuscular junction integrity); decreased mitochondrial biogenesis; anaplerosis. In each such foregoing case, treatment is accompanied by evaluating fat infiltration in muscle.

In some embodiments, the subject has not received prior treatment with an Active Moiety (e.g., a naïve subject) accompanied by evaluating fat infiltration in muscle.

In some embodiments, the subject has muscle weakness, e.g., muscle weakness of one, two, or more (e.g., all) of skeletal muscle, cardiac muscle, or smooth muscle. In certain embodiments, the subject has muscle weakness in one, two, three, four, five, six, or more (e.g., all) of a neck muscle, a torso muscle, an arm muscle, a shoulder muscle, a hand muscle, a leg muscle, or a foot muscle. Fat infiltration in muscle can be evaluated daily, every 2-3 days, weekly, every two weeks, every three weeks, and every four weeks after treatment to determine or evaluate the degree of fat infiltration in muscle, particularly to determine that the degree of fat infiltration in muscle is reduced by treatment with an Active Moiety. In the case where administration of an Active Moiety precedes an elective procedure, such as orthopedic surgery, evaluating fat infiltration in muscle can be undertaken to determine that the fat fraction in muscle is unchanged from before the surgery, or even improved.

A subject who has had orthopedic surgery, e.g., knee surgery, or hip surgery, elbow surgery, or has worn a cast benefits from administration of an Active Moiety accompanied by evaluating fat infiltration in muscle. When surgery is elective, e.g., for knee or hip replacement (also called total knee arthroplasty and total hip arthroplasty, respectively) administration of the Active Moiety, evaluation of fat infiltration in muscle, or both can be done before surgery, e.g., one week before surgery or two weeks before surgery, or can be done after surgery, and preferably is done before and after surgery. In particularly, evaluation of fat infiltration in muscle, specifically muscle most impacted by the surgery or treated by the surgery, can be done daily, every 2-3 days, weekly, every two weeks, every three weeks, and every four weeks after surgery to determine or evaluate the degree of fat infiltration in muscle, particularly to determine that the degree of fat infiltration in muscle is reduced by treatment with an Active Moiety, and more particularly to determine that the fat fraction in muscle is unchanged from before the surgery, or even improved.

In some embodiments, the subject has a neuromuscular disorder, e.g., myasthenia gravis or Lambert-Eaton myasthenic syndrome.

In some embodiments, the subject has muscular dystrophy, e.g., Duchenne muscular dystrophy, Becker muscular dystrophy, facioscapulohumeral muscular dystrophy, or myotonic dystrophy. In some embodiments, the subject has an inflammatory myopathy, e.g., polymyositis or dermatomyositis.

In some embodiments, the subject has one, two, or more (e.g., all) of low sodium levels (e.g., hyponatremia), low potassium levels (e.g., hypokalemia), or a calcium deficiency or relatively high calcium levels (e.g., hypercalcemia).

In some embodiments, the subject has muscle weakness associated with nerve damage, e.g., neuralgia or peripheral neuropathy. In some embodiments, the subject has a bone weakness disease, e.g., osteomalacia, osteogenesis imperfecta, rickets, or Hypophosphatasia.

In some embodiments, the subject has experienced a stroke or a transient ischemic attack. In some embodiments, the subject has an autoimmune disease, e.g., Graves' disease.

In some embodiments, the subject has hypothyroidism. In some embodiments, the subject has amyotrophic lateral sclerosis (ALS).

In some embodiments, administering the composition results in activation of muscle protein synthesis in the subject. In some embodiments, the composition also reduces muscle protein wasting.

In some embodiments, the composition results in an improvement in the degree of fat infiltration in muscle associated with one or both of immobilization or muscle disuse following injury in a subject. In some embodiments, the subject has had a surgery, e.g., rotator cuff surgery, knee surgery, or hip surgery, or has worn a cast, prior to administration of the composition. In some embodiments, the subject has had a hip fracture-related myopenia. In some embodiments, the subject has had a joint replacement. In some embodiments, the subject has had an injury repair surgery.

In some embodiments, the subject has ventilator-induced diaphragmatic dystrophy or ventilator-induced diaphragmatic dysfunction. In some embodiments, the subject has had one or both of ICU-acquired or burns-related myopathies.

In some embodiments, the subject has disease-related cachexia, e.g., a disease-related cachexia selected from chronic obstructive pulmonary disease (COPD), congestive heart failure (CHF), chronic kidney disease (CKD), and cancer.

In some embodiments, method of the invention further includes administration of a second agent. Such a second agent may exclude proteins, whether intact or in hydrolyzed form, such as whey, casein, lactalbumin, etc.

The present disclosure also provides a method for reducing muscle atrophy comprising administering to a subject in need thereof an effective amount of a composition described herein. In each such case effectiveness of therapy includes reduction of fat infiltration in muscle, and may include determining the degree of fat infiltration in muscle.

The present disclosure also provides a composition described herein for use as a medicament for reducing fat infiltration in muscle.

The present disclosure provides a composition described herein for use as a medicament for reducing fat infiltration in muscle, which may be in conjunction with treating one or more symptoms selected from the group consisting of immobilization, injury, surgery, malnutrition, fasting, aging, autophagy, reduced protein synthesis, anabolic resistance, neuromuscular junction integrity, insulin resistance, decreased mitochondrial biogenesis, and anaplerosis.

Dosage Regimens

The composition can be administered to a human subject according to a dosage regimen described herein.

Doses can be administered, e.g., twice daily, three times daily, four times daily, five times daily, six times daily, seven times daily, or more. The composition can be administered for at least 2 days, 3 days, 4 days, 5 days, 6 days, 7 days, or 2 weeks. Depending on the condition being treated, the composition can be administered for at least 10 weeks, 11 weeks, 12 weeks, 13 weeks, 14 weeks, 15 weeks, 16 weeks, 17 weeks, 18 weeks, 19 weeks, 20 weeks, or longer. In some embodiments, the composition can be administered chronically, e.g., more than 30 days, e.g., 31 days, 40 days, 50 days, 60 days, 3 months, 6 months, 9 months, one year, two years, or three years). If the condition of fat infiltration in muscle is chronic and unremitting, the invention contemplates administering an Active Moiety indefinitely, e.g., for the life of the subject.

The Active Moiety can be administered at a dose of about 4 g and about 80 g total amino acids, e.g., once per day, twice per day, three times per day, four times per day, five times per day, or six times per day (e.g., three times per day). In some embodiments, the composition is administered at a dose of about 5 g to about 15 g, about 10 g to about 20 g, about 20 g to about 40 g, or about 30 g to about 50 g total amino acids, e.g., once per day, twice per day, three times per day, four times per day, five times per day, or six times per day (e.g., three times per day).

The composition can be administered every 2 hours, every 3 hours, every 4 hours, every 5 hours, every 6 hours, every 7 hours, every 8 hours, every 9 hours, or every 10 hours to enhance muscle function in a subject (e.g., the subject has or is identified as having decreased muscle function due to aging, injury, atrophy, infection, or disease).

In some embodiments, the composition is administered prior to a meal (e.g., one, two, or more (e.g., all) of breakfast, lunch, or dinner). In some embodiments, the composition is administered conccurrent with a meal (e.g., one, two, or more (e.g., all) of breakfast, lunch, or dinner). In some embodiments, the composition is administered following a meal (e.g., one, two, or more (e.g., all) of breakfast, lunch, or dinner).

Production of Active Moiety and Pharmaceutical Compositions

Amino acids used to make the compositions may be agglomerated, and/or instantized to aid in dispersal and/or solubilization.

The amino acid compositions of the present disclosure may be made using amino acids and amino acid derivatives from the following sources, or other sources may used: e.g., FUSI-BCAA™ Instantized Blend (L-Leucine, L-Isoleucine and L-Valine in 2:1:1 weight ratio), FUSIL™ Instantized L-Leucine, L-Arginine HCl, L-Glutamine and other amino acids may be obtained from Ajinomoto Co., Inc; N-acetylcysteine may be obtained from Spectrum Chemical.

To produce the amino acid compositions of the instant disclosure, the following general steps may be used: the starting materials (individual amino acids and excipients) may be blended in a blending unit, followed by verification of blend uniformity and amino acid content, and filling of the blended powder into stick packs or other unit dosage form. The content of stick packs or other unit dosage forms may be dispersed in water at time of use for oral administration.

Pharmaceutical compositions of the present disclosure may be in a form suitable for oral use (for example aqueous or oily suspensions, emulsions, dispersible powders or granules, syrups or elixirs), for parental administration (for example as a sterile aqueous or oily solution for intravenous, subcutaneous, intramuscular dosing or as a suppository for rectal dosing) or for enteral administration (for example via tube feeding). Generally, however, pharmaceutical compositions of the invention will be for oral administration.

Food supplement and medical nutrition compositions of the invention will be in a form suitable for oral administration.

When combining raw materials, e.g., pharmaceutical grade amino acid entities and/or excipients, into a composition, contaminants may be present in the composition. A composition meets a standard for level of contamination when the composition does not substantially comprise (e.g., comprises less than 10, 5, 1, 0.1, 0.01, or 0.001% (w/w on a dry weight basis)) a contaminant. In some embodiments, a composition described in a method herein does not comprise a contaminant. Contaminants include any substance that is not deliberately present in the composition (for example, pharmaceutical grade amino acid entities and excipients, e.g., oral administration components, may be deliberately present) or any substance that has a negative effect on a product quality parameter of the composition (e.g., side effects in a subject, decreased potency, decreased stability/shelf life, discoloration, odor, bad taste, bad texture/mouthfeel, or increased segregation of components of the composition). In some embodiments, contaminants include microbes, endotoxins, metals, or a combination thereof. In some embodiments, the level of contamination, e.g., by metals, lecithin, choline, endotoxin, microbes, or other contaminants (e.g., contaminants from raw materials) of each portion of a composition is below the level permitted in food.

Excipients

The amino acid compositions of the present disclosure may be compounded or formulated with one or more excipients. Non-limiting examples of suitable excipients include a tastant, a flavorant, a buffering agent, a preservative, a stabilizer, a binder, a compaction agent, a lubricant, a dispersion enhancer, a disintegration agent, a flavoring agent, a sweetener, and a coloring agent.

In some embodiments, the excipient comprises a buffering agent. Non-limiting examples of suitable buffering agents include citric acid, sodium citrate, magnesium carbonate, magnesium bicarbonate, calcium carbonate, and calcium bicarbonate.

In some embodiments, the excipient comprises a preservative. Non-limiting examples of suitable preservatives include antioxidants, such as alpha-tocopherol and ascorbate, and antimicrobials, such as parabens, chlorobutanol, and phenol.

In some embodiments, the composition comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, and combinations thereof.

In some embodiments, the composition comprises a lubricant as an excipient. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

In some embodiments, the composition comprises a dispersion enhancer as an excipient. Non-limiting examples of suitable dispersants include starch, alginic acid, polyvinylpyrrolidones, guar gum, kaolin, xanthan gum, bentonite, purified wood cellulose, sodium starch glycolate, isoamorphous silicate, and microcrystalline cellulose as high HLB emulsifier surfactants.

In some embodiments, the composition comprises a disintegrant as an excipient. In some embodiments, the disintegrant is a non-effervescent disintegrant. Non-limiting examples of suitable non-effervescent disintegrants include starches such as corn starch, potato starch, pregelatinized and modified starches thereof, sweeteners, clays, such as bentonite, microcrystalline cellulose, alginates, sodium starch glycolate, gums such as agar, guar, locust bean, karaya, pecitin, and tragacanth. In some embodiments, the disintegrant is an effervescent disintegrant. Non-limiting examples of suitable effervescent disintegrants include sodium bicarbonate in combination with citric acid, and sodium bicarbonate in combination with tartaric acid.

In some embodiments, the excipient comprises a flavoring agent. Flavoring agents can be chosen from synthetic flavor oils and flavoring aromatics; natural oils; extracts from plants, leaves, flowers, and fruits; and combinations thereof. In some embodiments, the flavoring agent is selected from cinnamon oils; oil of wintergreen; peppermint oils; clover oil; hay oil; anise oil; *eucalyptus*; vanilla; citrus oil such as lemon oil, orange oil, grape and grapefruit oil; and fruit essences including apple, peach, pear, strawberry, raspberry, cherry, plum, pineapple, and apricot.

In some embodiments, the excipient comprises a sweetener. Non-limiting examples of suitable sweeteners include glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *Stevia Rebaudiana* (Stevioside); chloro derivatives of sucrose such as sucralose; and sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof.

In some embodiments, the composition comprises a coloring agent. Non-limiting examples of suitable color agents include food, drug and cosmetic colors (FD&C), drug and cosmetic colors (D&C), and external drug and cosmetic colors (Ext. D&C). The coloring agents can be used as dyes or their corresponding lakes.

Particular excipients may include one or more of: citric acid, lecithin, (e.g. Alcolec F100), sweeteners (e.g. sucralose, sucralose micronized NF, acesulfame potassium (e.g. Ace-K)), a dispersion enhancer (e.g. xanthan gum (e.g. Ticaxan Rapid-3)), flavorings (e.g. vanilla custard #4306, Nat Orange WONF #1326, lime 865.0032U, and lemon 862.2169U), a bitterness masking agent (e.g. 936.2160U), and natural or artificial colorings (e.g. FD&C Yellow 6). Table 5 in the Example illustrates a formulation with such excipients.

Dietary Compositions

The Active Moiety including amino acid entities can be formulated and used as a dietary composition, e.g., chosen from a medical food, a functional food, or a supplement. In such an embodiment, the raw materials and final product should meet the standards of a food product. Such uses include improving health of a subject having or identified as suffering from infiltration of fat in muscle due to aging, injury, atrophy, infection, or disease. In some embodiments, the subject has or is identified as having muscle deterioration, muscle decay, muscle atrophy, cachexia, sarcopenia, steroid myopathy, or muscular dystrophy. In some embodiments, the subject has one or both of type 2 diabetes or a relatively high BMI.

In some embodiments, administration of the dietary composition results in an improvement in one or more metabolic symptoms in the subject, e.g., one or more metabolic symptoms is selected from the following: increased free fatty acid and lipid metabolism, improved mitochondrial function, white adipose tissue (WAT) browning, decreased reactive oxygen species (ROS), increased levels of glutathione (GSH), decreased hepatic inflammation, decreased hepatocyte ballooning, improved gut barrier function, increased insulin secretion, or glucose tolerance. In certain embodiments, administration of the composition results in an improvement in one or more metabolic symptoms after a treatment period of 24 hours.

Biomarkers

Any of the methods disclosed herein can include evaluating or monitoring the effectiveness of administering a composition described herein to a subject by determining the degree of infiltration of fat in muscle in the subject, e.g., with CT or MRI. The subject may be in need of muscle function enhancement (e.g., a subject having muscle deterioration, muscle decay, muscle atrophy, cachexia, sarcopenia, drug-induced myopathy, muscular dystrophy, or myopenia). The In some embodiments, administration of the composition to the subject results in a decrease in levels of one or more (e.g., all) of myoglobin, myostatin, GDF-11, cortisol-AM, C-reactive protein, insulin, or cytokines (e.g., one or more (e.g., all) of IL-1A RBM, IL-1RA, IL-1 RI, IL-1 RII, IL-12, IL-18, or MCP-1) in the subject (Table 4). In some embodiments, administration of the composition to the subject results in an increase in levels of one or more (e.g., all) of P3NP, IGF-1, IGFBP1, IGFBP3, FGF-21, DHEAS, or mTORC1 in the subject (Table 4).

TABLE 4

Additional biomarkers to determine effect of the composition on muscle biology.

| Biomarker | Category | Expected Change in Response to Composition | Additional information regarding biomarker change on muscle synthesis and/or breakdown |
|---|---|---|---|
| Myoglobin | Muscle biology | Down | Decrease suggests a reduction in muscle breakdown and autophagy |
| Myostatin, GDF-11 | Muscle biology | Down | Myostatin act to inhibit muscle synthesis - decrease in levels indicate increase anabolism<br>Change in GDF-11 levels to further inform changes to muscle biology |
| P3NP | Muscle biology | Up | P3NP is released during collagen synthesis in muscle<br>Increased circulating P3NP indicates muscle growth, muscle repair and fibrosis |
| Cortisol-AM | Endocrine | Down | Endocrine molecules involved in regulating protein synthesis as stimulators/potentiators or inhibitors |
| C-reactive protein | Endocrine | Down | |
| IGF-1, IGFBP1, IGFBP3, FGF21, DHEAS | Endocrine | Up | Increase in potentiator levels and decrease in inhibitor levels are supportive of net anabolism |
| Insulin | Endocrine (glucose tolerance) | Down | Decrease indicates moderation in insulin resistance, and increased glucose handling and anabolic sensitivity |
| IL1ARBM, IL1RA, IL1RI, IL1RII, IL-12, IL-18, MCP-1, cytokines | Inflammation | Down | Increased muscle wasting is associated with a strong inflammatory response<br>Reduced levels of these inflammation biomarkers indicate reduction in inflammation<br>Overall profile of these biomarker can further provide dynamic assessment on interleukin response to the composition | effectiveness to the composition in treating a subject can further comprise a measure of the levels of one or more (e.g., all) of the following:

a) myostatin;
b) myoglobin;
c) Cortisol-AM;
d) C-reactive protein;
e) insulin;
f) cytokines (e.g., one or more (e.g., all) of IL-1A RBM, IL-1RA, IL-1 RI, IL-1 RII, IL-12, IL-18, or MCP-1);
g) GDF-11;
h) P3NP;
i) IGF-1;
j) IGFBP1;
k) IGFBP3;
l) FGF21;
m) DHEAS;
n) mTORC1;
o) Gcn2; or
p) AMP-activated protein kinase (AMPK).

In some embodiments of any of the methods disclosed herein, the measure of one or more of a)-p) is obtained from a sample acquired from the subject.

In some embodiments, the subject is evaluated prior to receiving, during, or after receiving, the composition.

EXAMPLE

The Example below is set forth to aid in the understanding of the invention, but is not intended to, and should not be construed to, limit its scope in any way.

Example 1. Treatment of Immobilization in Subjects with an Amino Acid Composition not Only Reduces Loss of Muscle Mass and Function, but Surprisingly Reduces Fat Infiltration The study described herein features the administration of a composition including amino acids to healthy subjects undergoing unilateral knee immobilization. The goal of this study was to determine the impact of an amino acid composition on muscle atrophy after 7 days of single leg immobilization and 14 days of recovery post-immobilization. The composition included about 1 g of L-leucine, about 0.5 g of L-isoleucine, about 0.5 g of L-valine, about 1.5 g of L-arginine (or 1.81 g of L-arginine HCl), about 1.33 g of L-glutamine, about 0.15 g of N-acetylcysteine, about 0.08 g of L-histidine, about 0.35 g of L-lysine, about 0.08 g of L-phenylalanine, and about 0.17 g of L-threonine per stick packet for administration in four stick packs three times per day (e.g., a total of about 68 or 72 g per day, or about 23 g or 24 g three times per day). The composition also included excipients as shown in Table 5.

TABLE 5

Ingredient contents in each stick pack.

| INGREDIENT | GRADE | FUNCTION | GRAMS | SOURCE; COMMENT |
|---|---|---|---|---|
| Amino Acids | USP | Active Pharmaceutical Ingredient (API) | 6 | Various sources; Non-instantized form (MFG scale) |
| Citric Acid | USP | pH, Flavor | 0.67 | Spectrum Chems; f(volume) ≤ 1.0% w/v |
| Acesulfame K | NF | Sweetness (rapid onset) | 0.05 | Spectrum Chems; Target 1 Sweetener |
| Sucralose | NF | Sweetness (slow onset) | 0.03 | Spectrum Chems; WHO ADI ≤ 15 mg/kg |
| Lecithin (Alecolec F100) | FCC | Wetting Agent | 0.83 | American Lecithin Company |
| Xanthan Gum | FCC | Stabilizer/Thickener | 0.24 | TIC Gums; f(volume) ≤ 0.5% w/v |
| Vanilla Custard (Art) | GRAS | Taste/Aroma | 0.06 | David Michael; Mask sulfur |
| Orange (Natural and WONF) | GRAS | 1° flavor | 0.36 | David Michael; Citrus profile matches low pH |
| Lime (Natural and WONF) | GRAS | 2° flavor | 0.05 | FONA; Single flavor supplier |
| Lemon (Natural and artificial) | GRAS | 2° flavor | 0.05 | FONA; Single flavor supplier |
| Taste Modifier | GRAS | Bitterness masking | 0.12 | FONA; Useful at low volume |
| FD&C Yellow No. 6 | USP | Color | 0.009 | Sensient; Match flavor profile |

In the study, subjects received the amino acid composition three times daily for 28 days. Amino acids were provided in powder form to be dissolved in 8 oz. of water. Participants underwent single-leg immobilization for 7 days (days 8-15) during the 28-day study period. An immobilization device was used for 7 days of single-leg immobilization of the dominant knee (based on maximal isometric leg strength) with a knee brace worn in a fixed flexion position at 140° (e.g., a Breg brace).

Control subjects received placebo three times daily for 28 days. Placebo consisted of an amount of maltodextrin (NF grade) equivalent in caloric content to the amount of amino acids administered, with the same excipients, dissolved in 8 oz. of water.

The primary outcome measure of this study was safety and tolerability. In addition, muscle disuse atrophy, in particular, the impact of the amino acid formulation on muscle atrophy after 7 days of single leg immobilization was studied. The secondary outcome measures included muscle function based on knee strength, muscle cross-section area and volume, muscle fiber quality, and lean muscle mass. The percentage change in lean muscle mass in the subjects was determined using dual-energy x-ray absorptiometry (DEXA). The percentage change in maximum torque as measured using a BioDex machine (measured in Newton-meters) and percentage change in the time to maximum torque (measured in seconds) were also assessed. Muscle biopsies were performed to determine muscle fiber cross-sectional area (CSA). Muscle size was assessed via MRI. Muscle health was assessed by electrical impedance myography (EIM) measurements. Assessments were performed at baseline (day 1), pre-immobilization (day 8), post-immobilization (day 15), and recovery (day 28).

More specifically, MRIs were performed at Days 1, 8, 15, and 28. Axial (transverse) images were obtained from both thighs from the distal end of the femur to the greater trochanter using GE high fidelity 3T magnet. A fast-recovery, fast spin echo pulse sequence was used, along with IDEAL (iterative decomposition of water and fat with echo asymmetry and least-squares estimation) post-processing to obtain water-only, fat-only, in-phase and out-of-phase images of the thighs. The following parameters were used: TR=2000 msec, TE=30 msec, refocusing flip angle=111 degrees, echo train length=6, ASSET (parallel imaging factor)=2, field of view=42×21 cm, acquisition matrix=512× 256, 3-mm slice thickness, 0-mm slice gap. A total of approximately 160 slices were acquired, but varied depending on length of the thigh. The acquisition was done in two sections, a lower stage, and an upper stage. Total scan time for both stages was approximately 11 minutes. The scans were uploaded onto Analyze Pro software. The 50% region between the greater trochanter of the hip and lateral epicondyle of the knee were used for analysis. The segmentation features of the software were used to differentiate between the bone, fat, right muscle, right quadriceps, left muscle and left quadriceps. Then every third slice in the 50% region was manually traced for the quadriceps muscles of both legs. The highest number from these measurements was taken as the peak quadriceps cross-sectional area. The software was then able to take every third slice that was manually measured and extrapolate that data for every slice in the 50% region to get an estimate of quadriceps volume. CSA was expressed in mm2 and muscle volume in mm3. Protocol adapted from Reeder et al., 2005.

To obtain independent verification of the imaging data, DIXON sequences of the upper and lower thighs were securely transferred to the Image Analysis Group (IAG, London, UK) for whole muscle volume analysis and an additional analysis to measure intramuscular fat fraction. Given the water and fat images it is possible to generate a Fat Fraction (FF) image as:

$FF=F/(W+F)$, where $F$=fat, and $W$=water.

IAG calculated these images and added them to the individual DICOM studies. As the base images can give spurious regions of high fat fraction due to noise, a thresholding filter was used to reduce these small peripheral artefacts and minimize noise in regions where both the fat and water signals are small. Segmentations were carried out on the upper thigh FF images. The segmentation was from the middle of the thigh towards the pelvis for 20 slices. The segmentation was carried out manually from each sequence. Once segmented, the slice ROIs were grouped to form a volume ROI and the statistics automatically calculated.

Key criteria for selecting subjects included the following: 1) generally healthy, non-smoking; 2) willing and able to provide informed consent; 3) men age 20-45 years; and 4) BMI between 25 and 35 kg/m$^2$. Exclusion Criteria included the following: 1) smokers; 2) subject has any concurrent medical, orthopedic, or psychiatric condition that, in the opinion of the investigator, would compromise his/her ability to comply with the study requirements; 3) history of cancer within the last 5 years, except basal cell carcinoma, non-squamous skin carcinoma, prostate cancer, or carcinoma in situ with no significant progression over the past 2 years; 4) significant orthopedic, cardiovascular, pulmonary, renal, liver, infectious disease, immune disorder (requiring ongoing medical care), or metabolic/endocrine disorder (e.g., diabetes, high cholesterol, elevated fasting blood sugar) or other disease that would preclude oral protein supplement ingestion and/or assessment of safety and study objectives; 5) any cachexia-related condition (e.g., relating to cancer, tuberculosis, or human immunodeficiency virus infection and acquired immune deficiency syndrome) or any genetic muscle diseases or disorders; 6) current illnesses that could interfere with the study (e.g. prolonged severe diarrhea, regurgitation, or difficulty swallowing); 7) subject participated in a study of an investigational product less than 60 days or 5 half-lives of the investigational product, whichever is longer, before enrollment in this study; 8) hypersensitivity to any of the components of the test product; 9) excessive alcohol consumption (>21 units/week); 10) known sensitivity or allergy to amino acids or any ingredient in the test formulations; 11) prior gastrointestinal bypass surgery (e.g., lapband surgery), irritable bowel disease, or irritable bowel syndrome; 12) history of bleeding diathesis, platelet or coagulation disorders, or antiplatelet/anticoagulation therapy (up to 81 mg of baby aspirin per day taken as a prophylactic is permitted); 13) personal or family history of clotting disorder or deep vein thrombosis; 14) concomitant use of corticosteroids, testosterone replacement therapy (ingestion, injection, or transdermal), any anabolic steroid, creatine, whey protein supplements, casein, or branched-chain amino acids (BCAAs) within 45 days prior to screening; 15) contraindications to an MRI scan (e.g. subjects with non-removable ferromagnetic implants, pacemakers, aneurysm clips or other foreign bodies, or subjects with claustrophobic symptoms that would contraindicate an MRI scan); 16) hemoglobin less than 11.5 mg/dl at screening; or 17) platelets less than 150,000/uL (150×109/L) at screening.

The findings from this study suggest that the decline in lean leg mass as a result of unilateral limb immobilization (i.e. disuse atrophy), including reduction in fat infiltration into the muscle, was attenuated in those that received the LIVRQNACHKFT amino acid combination, as compared to those that received placebo. These results in subjects undergoing a unilateral limb immobilization suggest that the amino acid combination attenuated this decline in lean mass of the immobilized leg, while preserving muscle strength. The immobilized leg in the placebo administered groups did not recover their lean mass to the post-immobilized or the pre-immobilized state during the two week recovery period. By contrast, administration of the amino acid combination maintained and/or improved the lean leg mass within this two week recovery period to that of the post and pre-immobilization. The decline in muscle strength seen after a week of unilateral limb immobilization in the placebo group was also attenuated by the amino acid combination. The non-immobilized leg in either the Placebo or the LIVRQNACHKFT amino acid administered group did not appear to lose their lean leg mass nor their muscle strength to the same extent as the corresponding immobilized leg during the knee brace period, as expected of an appropriate control.

CSA of specific fibers within the vastus lateralis was preserved during immobilization with LIVRQNACHKFT vs. Pbo administration. One week of immobilization led to a 2.2% (±4.0) decrease in fiber CSA (FIG. 1). Consistent with the existing literature, in the Pbo group, muscle disuse tended to result in a preferential loss of Type II vs. Type I fibers (4.5±4.8% loss for Type II vs. no change for Type I). By contrast, LIVRQNACHKFT administration preserved the cross-sectional area of both fiber types during immobilization. Quantification of CSA is shown in FIG. 1, with the following changes observed between LIVRQNACHKFT and Pbo: increase of 4.1-fold for total fibers; 1.7-fold for Type II fibers; 12-fold for Type I fibers (P=0.08). Of note, LIVRQNACHKFT had a particularly pronounced effect on the slow twitch type I fibers, in not only preserving them, but tended to induce their growth (13.3±7.4% increase in Type I fiber CSA from Day 8 to Day 15).

Figure 2A:
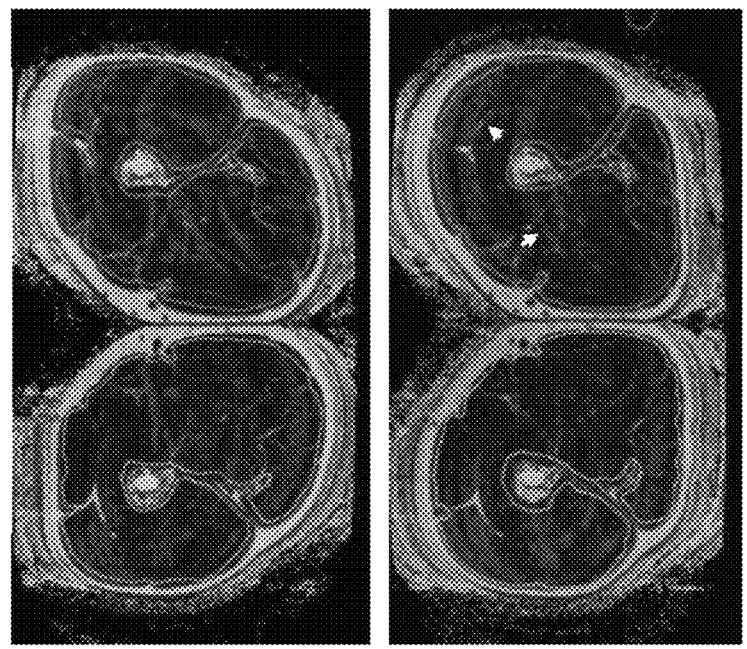
FIGS. 2A and 2B. Change in quadriceps fat fraction during immobilization (Day 15 vs. Day 8) in both immobilized and nonimmobilized legs. 2A. Representative images depicting fat fraction (FF) changes in the immobilized and non-immobilized thighs of a subject who received treatment and a subject who received placebo. Purple represents fat fraction; red represents muscle fraction. 2B. Plot of fat fraction changes quantified across all subjects.
Figure 2A:
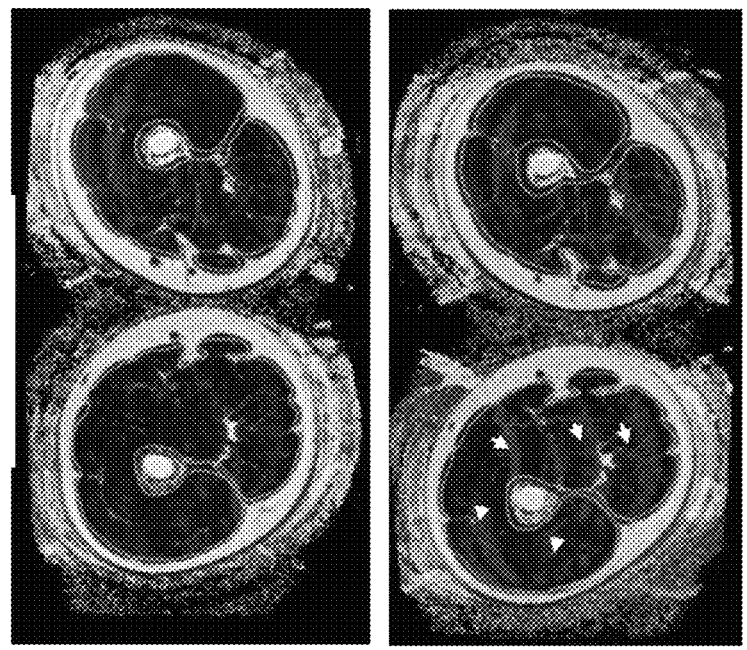
Figure 2B:
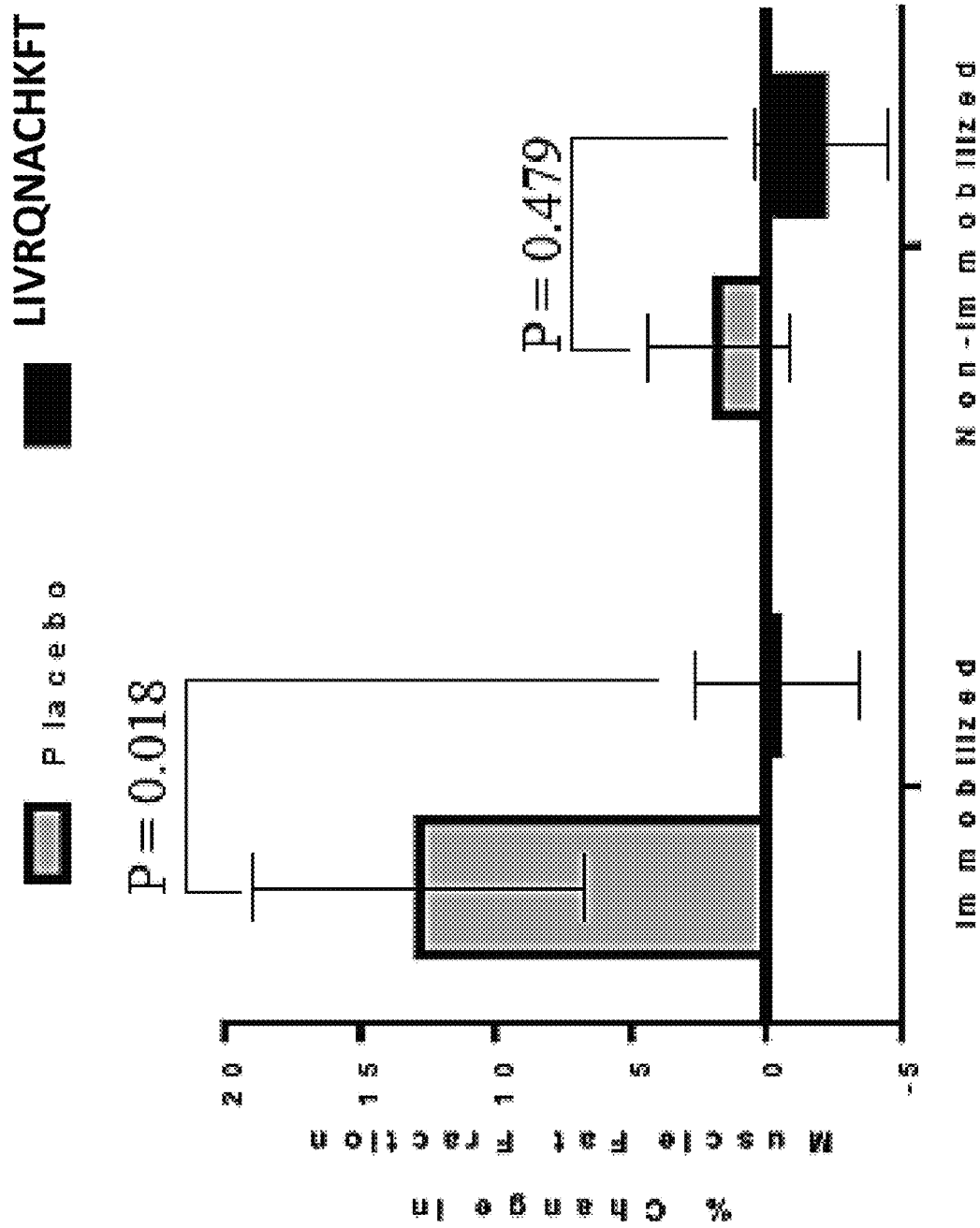

The unprecedented observation of LIVRQNACHKFT's effect on the oxidative, slow twitch Type I fibers could suggest an impact on insulin sensitization, and the latter has been closely associated with muscle fat infiltration (Albu et al. 2005). Consistent with this unprecented effect on Type I muscle fibers, LIVRQNACHKFT administration significantly attenuated muscle fat infiltration during limb immobilization (FIGS. 2A and 2B). Representative images depicting fat fraction (FF) changes show that in a subject administered Pbo (FIG. 2A), the non-immobilized leg had no change in FF, while the immobilized leg had increased FF and decreased muscle mass between Day 8 and 15. By contrast, in a subject administered LIVRQNACHKFT (FIG. 2A), the immobilized leg had lower fat fraction, and a higher muscle content following immobilization, illustrating LIVRQNACHKFT anti-atrophic effects. These FF changes were quantified across all subjects and results are plotted in FIG. 2B. Percent change in quadriceps muscle fat fraction on Day 15 vs. Day 8 was +12.8±6.1% in Pbo vs. −0.41±3.07% in LIVRQNACHKFT (P=0.018) in the immobilized leg. As expected, the non-immobilized leg had significantly less to no muscle fat infiltration: 1.76±2.6% (Pbo) vs. −2.05±2.4% (LIVRQNACHKFT), with no statistical difference between the groups (P=0.479, FIG. 2B).

Figure 3:
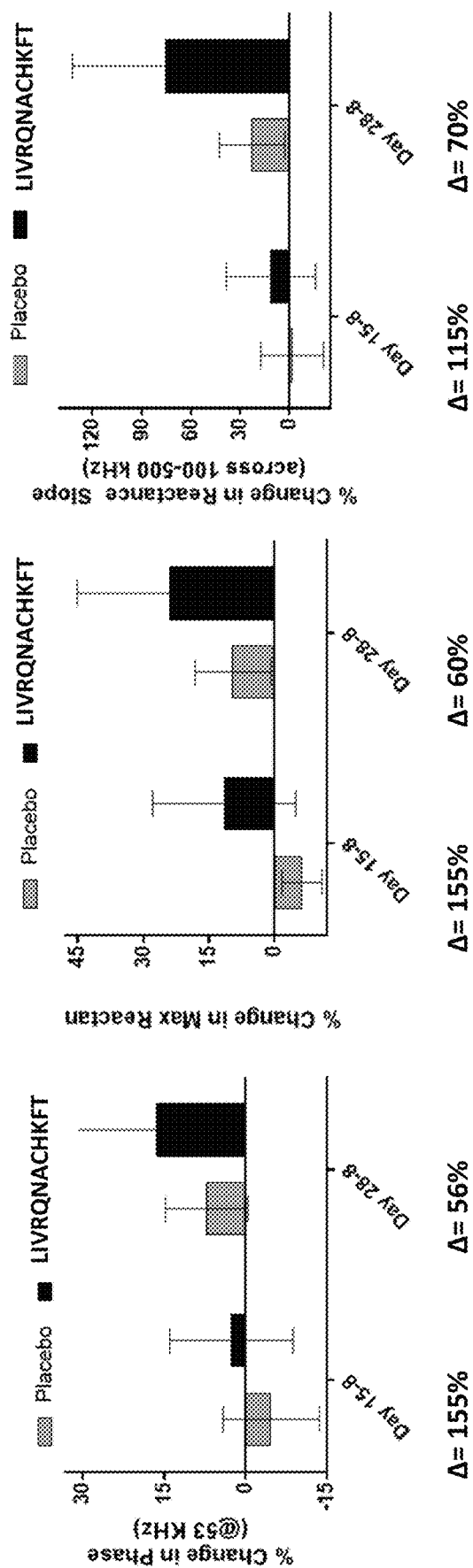
FIG. 3. Change in vastus lateralis electrical impedance measurement (EIM) parameters (phase, max reactance, and change in reactance slope) during immobilization & recovery. Data are mean±SEM from n=9 (Pbo) and n=10 (therapeutic).

Consistent with the literature (Tarulli et al. 2009), we observed decreases in phase, maximum reactance, and reactance slope (these parameters are considered to be reflective of muscle health, Rutkove 2009) during limb immobilization (i.e. from Day 8 to 15) in the Pbo group (FIG. 3).

By contrast, LIVRQNACHKFT administration resulted in the attenuation, if not a numerical increase in these parameters during immobilization (with relative differences versus Pbo ranging from 115% to 155%). During the recovery phase, these parameters returned to pre-immobilization levels in both groups (Day 28 vs. Day 8), but these parameters tended to be higher in the LIVRQNACHKFT group compared to Pbo, with relative differences of 56%, 60%, and 70% for phase, max reactance, and reactance slope, respectively.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

What is claimed is:

1. A method for reducing fat infiltration in muscle comprising administering to a subject at risk of fat infiltration in muscle a composition comprising:
   a) a leucine amino acid entity, an arginine amino acid entity, and a glutamine amino acid entity;
   b) a N-acetylcysteine (NAC) entity; and
   c) an essential amino acid (EAA)-entity chosen from a histidine amino acid-entity, a lysine amino acid-entity, a phenylalanine amino acid-entity, and a threonine amino acid-entity or a combination of two, three, or four of the EAAs.

2. The method of claim 1, wherein the subject at risk of fat infiltration in muscle has a rotator cuff injury.

3. The method of claim 2, wherein administration of the composition precedes a surgery for the rotator cuff injury.

4. The method of claim 2, further comprising determining a level of fat infiltration in shoulder muscle affected by the rotator cuff injury before surgery.

5. The method of claim 2, further comprising determining a level of fat infiltration in shoulder muscle affected by the rotator cuff injury after surgery.

6. The method of claim 2, wherein the subject is an elderly subject.

7. The method of claim 1, wherein the subject at risk of fat infiltration in muscle has chronic back pain (fat infiltration in paraspinal muscles); HIV (fat infiltration in locomotor muscles); spinal cord injury; stroke; COPD; end-stage liver disease (ESLD), hepatic encephalopathy, variceal bleeding, portal hypertension, ascites, infection risk, sepsis, all-cause hospitalization, all-cause and liver-related mortality; or muscle weakness associated with ageing.

8. The method of claim 1, wherein administering the composition to the subject at risk of fat infiltration in muscle improves a muscle function of sequestering glucose.

9. The method of claim 8, wherein the subject at risk for fat infiltration in muscle has diabetes or metabolic disease.

10. The method of claim 1, wherein the subject at risk of fat infiltration in muscle has cancer.

11. The method of claim 10, wherein the cancer is colorectal cancer or periampullary cancer.

12. The method of claim 1, wherein the subject at risk for fat infiltration in muscle does not have significant increase in BMI, sarcopenia, or other overt conditions.

13. The method of claim 1, wherein the subject at risk for fat infiltration in muscle suffers from cirrhosis without sarcopenia.

14. The method of claim 1, wherein the degree of fat infiltration in muscle is determined by magnetic resonance imaging (MRI).

15. The method of claim 1, wherein at least one of methionine (M), trytophan (W), valine (V), or cysteine (C) is absent, or if present, is present at less than 1 weight (wt.) %.

16. The composition of claim 1, wherein the total wt. % of (a)-(c) is greater than the total wt. % of any other amino acid entity in the composition.

17. The method of claim 1, wherein the composition further comprises an isoleucine amino acid entity, a valine amino acid entity, or both an isoleucine amino acid entity and a valine amino acid entity.

18. The method of claim 1, wherein at least one of the leucine amino acid entity, the arginine amino acid, the glutamine amino acid entity, or one, two, three, or all of the EAA amino acid entities is a free amino acid, and at least 50 wt. % of the total dry wt. of the composition is one or more amino acid entities in free form.

19. The method of claim 1, wherein at least one of the leucine amino acid entity, the arginine amino acid entity, the glutamine amino acid entity, or one, two, three, or all of the EAA amino acid entities is in salt form, and at least 50 wt.% of the total dry wt. of the composition is one or more amino acid entities in salt form.

20. The method of claim 17, wherein the composition comprises about 0.5 g to about 15 g of the leucine amino acid entity, about 0.25 g to about 10 g of the isoleucine amino acid entity, about 0.25 g to about 10 g of the valine amino acid entity, about 0.5 to about 25 g of the arginine amino acid entity, about 0.5 g to about 20 g of the glutamine amino acid entity, about 0.1 to about 5 g the NAC or a salt thereof, about 0.05 g to about 3 g of the L-histidine or a salt thereof, about 0.05 to about 6 g of the L-lysine or a salt thereof, about 0.04 to about 2 g of the L-phenylalanine or a salt thereof, and about 0.08 to about 4 g of the L-threonine or a salt thereof entity; e.g., about 1 g of the leucine amino acid entity, about 0.5 g of the isoleucine amino acid entity, about 0.5 g of the valine amino acid entity, about 1.5 g or about 1.81 of the arginine amino acid entity, about 1.33 g of the glutamine amino acid entity, about 0.15 g or about 0.3 g of the NAC or a salt thereof, about 0.08 g of the L-histidine or a salt thereof, about 0.35 g of the L-lysine or a salt thereof, about 0.08 g of the L-phenylalanine or a salt thereof, and about 0.17 g of the L-threonine or a salt thereof.

21. The method of claim 1, wherein the composition is a pharmaceutical composition and further comprises a pharmaceutically acceptable excipient.

* * * * *